US006642021B2

(12) United States Patent
Cunningham, Jr. et al.

(10) Patent No.: US 6,642,021 B2
(45) Date of Patent: Nov. 4, 2003

(54) METHODS OF PRODUCING CAROTENOIDS BY THE EXPRESSION OF PLANT ε-CYCLASE GENES

(75) Inventors: Francis X. Cunningham, Jr., Chevy Chase, MD (US); Zairen Sun, Hyattsville, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 09/323,998

(22) Filed: Jun. 2, 1999

(65) Prior Publication Data

US 2002/0102631 A1 Aug. 1, 2002

Related U.S. Application Data

(60) Continuation-in-part of application No. 09/088,724, filed on Jun. 2, 1998, now abandoned, and a continuation-in-part of application No. 09/088,725, filed on Jun. 2, 1998, now abandoned, and a continuation-in-part of application No. 08/937,155, filed on Sep. 25, 1997, which is a division of application No. 08/624,125, filed on Mar. 29, 1996, now Pat. No. 5,744,341.

(51) Int. Cl.[7] .............................................. C12P 23/00

(52) U.S. Cl. ........................................................ 435/67

(58) Field of Search .................................. 435/67, 69.1

(56) References Cited

U.S. PATENT DOCUMENTS

| | | |
|---|---|---|
| 5,429,939 A | 7/1995 | Misawa et al. |
| 5,539,093 A | 7/1996 | Fitzmaurice et al. |
| 5,589,581 A | 12/1996 | Misawa et al. |
| 5,744,341 A | 4/1998 | Cunningham et al. |
| 5,792,903 A | 8/1998 | Hirschberg et al. |
| 5,811,273 A | 9/1998 | Misawa et al. |
| 5,849,524 A | 12/1998 | Kondo et al. |

FOREIGN PATENT DOCUMENTS

| | | | |
|---|---|---|---|
| WO | 96/28545 | | 9/1996 |
| WO | WO 98/06862 | * | 2/1998 |

OTHER PUBLICATIONS

Ronen et al. Lycopersicon esculentum mRNA for lycopene epsilon–cyclase. GenBank Accession No. Y14387 publicly available on Mar. 31, 1998.*

Hugueney et al. Metabolism of cyclic carotenoids: a model for the alteration of this biosynthetic pathway in Capsicum annuum chromoplasts. The Plant Journal (1995) 8(3): 417–424.*

The Plant Journal (1999) 17(4), 341–351 "Regulation of carotenoid biosynthesis during tomato fruit development: expression of the gene for lycopene epsilon–cyclase is down–regulated during ripening and is elevated in the mutant Delta" Ronen, et al.

Current Opinion in Biotechnology, 1999, 10:186–191, "Production of high–value compounds: carotenoids and vitamin E" Hirschberg.

The Plant Cell, vol. 6, 1107–1121, Aug. 1994 "Molecular Structure and Enzymatic Function of Lycopene Cyclase from the Cyanobacterium Synechococcus sp Strain PCC7942" Cunningham, et al.

(List continued on next page.)

Primary Examiner—Ponnathapu Achutamurthy
Assistant Examiner—Kathleen Kerr
(74) Attorney, Agent, or Firm—Arent Fox Kintner Plotkin & Kahn

(57) ABSTRACT

Nucleic acid sequences encoding ∈-cyclase, isopentenyl pyrophosphate isomerase and β-carotene hydroxylase as well as vectors containing the same and hosts transformed with the vectors. Methods for controlling the ratio of various carotenoids in a host and for the production of novel carotenoid pigments. The present invention also provides a method for screening for eukaryotic genes encoding carotenoid biosynthesis, and for modifying the disclosed enzymes.

10 Claims, 35 Drawing Sheets

OTHER PUBLICATIONS

The Plant Cell, vol. 8, 1613–1626, Sep. 1996 "Functional Analysis of the β and ε Lycopene Cyclase Enzymes of Arabidopsis Reveals a Mechanism for Control of Cyclic Carotenoid Formation" Cunningham, et al.

Campbell et al., Plant Mol. Biol. 36:323–328 1997.

Blanc, et al., Plant Physiol. 111:652 Jun./1996.

Anderson et al., J. Biol. Chem. 264:19169–19175 Nov./1989.

Hahn et al., J. Biol. Chem. 270:11298–11303 May/1995.

Buckner et al. Meth. Enzymol. 214:311–323. 1993.

Goodwin, Meth. Enzymol. 214:331–340, 1993.

Archives of Biochemistry and Biophysics vol. 230, No.2, pp. 446–454, 1984, Sandra L. Spurgeon, et al., "Isopentenyl Pyrophosphate Isomerase and Prenyltransferase From Tomato Fruit Plastids".

FEBS Letters, vol. 328, No. 1–2, pp. 130–138, Aug. 1993, Francis X. Cunningham, Jr., et al. "Cloning and Functional Expression in *Escherichia coli* of a Cyanobacterial Gene for Lycopene Cyclase. The Enzyme That Catalyzes the Biosynthesis of β–Carotene".

The Journal of Biological Chemistry, vol. 271, No. 13, Mar. 29, 1996 pp. 7774–7780, Núria Cunillera, et al., "*Arabidopsis thaliana* Contains Two Differentially Expressed Farnesyl–Diphosphate Synthase Genes".

The Journal of Biological Chemistry, vol. 271, No. 40, pp. 24349–24352, Oct. 4, 1996, Zairen Sun, et al. "Cloning and Functional Analysis of the β–Carotene Hydroxylase of *Arabidopsis thaliana*".

Annual Review of Plant Physiology and Molecular Biology, vol. 45, pp 287–301, Glenn E. Bartley, et al., "Molecular Biology of Carotenoid Biosynthesis in Plants".

Chem. Abstract 125:294752 1996.

* cited by examiner

Fig.4

*Arabidopsis thaliana epsilon* cyclase:

SEQ ID No.1
SEQ ID No.2

```
                         acaaaaggaaataattag attcctctttctgcttgctataccttgata   48
       gaacaatataacaatggtgtaagtcttctc gctgtattcgaaattatttggaggaggaaa  108
       atggagtgtgttggggctaggaatttcgca gcaatggcggtttcaacatttccgtcatgg  168
     1  M  E  C  V  G  A  R  N  F  A  A  M  A  V  S  T  F  P  S  W
       agttgtcgaaggaaatttccagtggttaag agatacagctataggaatattcgtttcggt  228
    21  S  C  R  R  K  F  P  V  V  K  R  Y  S  Y  R  N  I  R  F  G
       ttgtgtagtgtcagagctagcggcggcgga agttccggtagtgagagttgtgtagcggtg  288
    41  L  C  S  V  R  A  S  G  G  G  S  S  G  S  K  S  C  V  A  V
       agagaagatttcgctgacgaagaagatttt gtgaaagctggtggttctgagattctattt  348
    61  R  E  D  F  A  D  E  E  D  F  V  K  A  G  G  S  K  I  L  F
       gttcaaatgcagcagaacaaagatatggat gaacagtctaagcttgttgataagttgcct  408
    81  V  Q  M  Q  Q  N  K  D  M  D  E  Q  S  K  L  V  D  K  L  P
       cctatatcaattggtgatggtgctttggat catgtggttattggttgtggtcctgctggt  468
   101  P  I  S  I  G  D  A  L  D  H  V  V  I  G  C  G  P  A  G
       ttagccttggctgcagaatcagctaagctt ggattaaaagttggactcattggtccagat  528
   121  L  A  L  A  A  E  S  A  K  L  G  L  K  V  G  L  I  G  P  D
       cttcctttttactaacaattacggtgtttgg gaagatgaattcaatgatcttgggctgcaa  588
   141  L  P  F  T  N  N  Y  G  V  W  E  D  E  F  N  D  L  G  L  Q
       aaatgtattgagcatgtttggagagagact attgtgtatctggatgatgacaagcctatt  648
   161  K  C  I  E  H  V  W  R  E  T  I  V  Y  L  D  D  D  K  P  I
       accattggccgtgcttatggaagagttagt cgacgtttgctccatgaggagcttttgagg  708
   181  T  I  G  R  A  Y  G  R  V  S  R  R  L  L  H  E  E  L  L  R
       aggtgtgtcgagtcaggtgtctcgtaccttt agctcgaaagttgacagcataacagaagct  768
   201  R  C  V  E  S  G  V  S  Y  L  S  S  K  V  D  S  I  T  E  A
       tctgatggccttagacttgttgcttgtgac gacaataacgtcattccctgcaggcttgcc  828
   221  S  D  G  L  R  L  V  A  C  D  D  N  N  V  I  P  C  R  L  A
       actgttgcttctggagcagcttcggggaag ctcttgcaatacgaagttggtggacctaga  888
   241  T  V  A  S  G  A  A  S  G  K  L  L  Q  Y  E  V  G  G  P  R
       gtctgtgtgcaaactgcatacggcgtggag gttgaggtggaaaatagtccatatgatcca  948
   261  V  C  V  Q  T  A  Y  G  V  E  V  E  V  E  N  S  P  Y  D  P
       gatcaaatggttttcatggattacagagat tatactaacgagaaagttcggagcttagaa 1008
   281  D  Q  M  V  F  M  D  Y  R  D  Y  T  N  E  K  V  R  S  L  E
       gctgagtatccaacgtttctgtacgccatg cctatgacaaagtcaagactcttcttcgag 1068
   301  A  E  Y  P  T  F  L  Y  A  M  P  M  T  K  S  R  L  F  F  E
       gagacatgtttggcctcaaaagatgtcatg ccctttgatttgctaaaaacgaagctcatg 1128
   321  E  T  C  L  A  S  K  D  V  M  P  F  D  L  L  K  T  K  L  M
       ttaagattagatacactcggaattcgaatt ctaaagacttacgaagaggagtggtcctat 1188
   341  L  R  L  D  T  L  G  I  R  I  L  K  T  Y  E  E  E  W  S  Y
       atcccagttggtggttccttgccaaacacc gaacaaaagaatctcgcctttggtgctgcc 1248
   361  I  P  V  G  G  S  L  P  N  T  E  Q  K  N  L  A  F  G  A  A
       gctagcatggtacatcccgcaacaggctat tcagttgtgagatcttttgtctgaagctcca 1308
   381  A  S  M  V  H  P  A  T  G  Y  S  V  V  R  S  L  S  E  A  P
       aaatatgcatcagtcatcgcagagatacta agagaagagactaccaaacagatcaacagt 1368
   401  K  Y  A  S  V  I  A  E  I  L  R  E  E  T  T  K  Q  I  N  S
       aatatttcaagacaagcttgggatactta tggccaccagaaaggaaaagacagagagca 1428
   421  N  I  S  R  Q  A  W  D  T  L  W  P  P  E  R  K  R  Q  R  A
       ttctttctctttggtcttgcactcatagtt caattcgataccgaaggcattagaagcttc 1488
   441  F  F  L  F  G  L  A  L  I  V  Q  F  D  T  E  G  I  R  S  F
       ttccgtactttcttccgccttccaaaatgg atgtggcaagggtttctaggatcaacatta 1548
   461  F  R  T  F  F  R  L  P  K  W  M  W  Q  G  F  L  G  S  T  L
       acatcaggagatctcgttctctttgcttta tacatgttcgtcatttcaccaaacaatttg 1608
   481  T  S  G  D  L  V  L  F  A  L  Y  M  F  V  I  S  P  N  N  L
       agaaaaggtctcatcaatcatctcatctct gatccaaccggagcaaccatgataaaaacc 1668
   501  R  K  G  L  I  N  H  L  I  S  D  P  T  G  A  T  M  I  K  T
       tatctcaaagtatgatttacttatcaactc ttaggtttgtgtatatatatgttgatttat 1728
   521  Y  L  K  V
       ctgaataatcgatcaaagaatggtatgtgg gttactaggaagttggaaacaaacatgtat 1788
       agaatctaaggagtgatcgaaatggagatg gaaacgaaaagaaaaaaatcagtctttgtt 1848
       ttgtggttagtg                                                    1860
```

Fig.5

(SEQ. ID No.3)

```
  1 gctctttctc ctcctcctct accgatttcc gactccgcct cccgaaatcc
 51 ttatccggat tctctccgtc tcttcgattt aaacgctttt ctgtctgtta
101 cgtcgtcgaa gaacggagac agaattctcc gattgagaac gatgagagac
151 cggagagcac gagctccaca aacgctatag acgctgagta tctggcgttg
201 cgtttggcgg agaaattgga gaggaagaaa tcggagaggt ccacttatct
251 aatcgctgct atgttgtcga gctttggtat cacttctatg gctgttatgg
301 ctgtttacta cagattctct tggcaaatgg agggaggtga gatctcaatg
351 ttggaaatgt ttggtacatt tgctctctct gttggtgctg ctgttggtat
401 ggaattctgg gcaagatggg ctcatagagc tctgtggcac gcttctctat
451 ggaatatgca tgagtcacat cacaaaccaa gagaaggacc gtttgagcta
501 aacgatgttt ttgctatagt gaacgctggt ccagcgattg gtctcctctc
551 ttatggattc ttcaataaag gactcgttcc tggtctctgc tttggcgccg
601 ggttaggcat aacggtgttt ggaatcgcct acatgtttgt ccacgatggt
651 ctcgtgcaca agcgtttccc tgtaggtccc atcgccgacg tcccttacct
701 ccgaaaggtc gccgccgctc accagctaca tcacacagac aagttcaatg
751 gtgtaccata tggactgttt cttggaccca aggaattgga agaagttgga
801 ggaaatgaag agttagataa ggagattagt cggagaatca aatcatacaa
851 aaaggcctcg ggctccgggt cgagttcgag ttcttgactt taaacaagtt
901 ttaaatccca aattcttttt ttgtcttctg tcattatgat catcttaaga
951 cggtct
```

Fig.6

|  |  |  |  |  |  |  |  | 64 |
|---|---|---|---|---|---|---|---|---|
| (SEQ ID No.4) A.thal. |  |  | SFSS | SSTDFRLRLP | KSLSGFSPSL | RFKRFSVCYV | VEERRQNSPI | ENDERPESTS STNAIDAEYL |

|  |  |  |  |  |  |  |  |  | 144 |
|---|---|---|---|---|---|---|---|---|---|
| (SEQ ID No.5) | A.thal. Alical. | ALRLAFKLER | KKSERSTYLI | AAMLSSFGIT | SMAVMAVYYR | FSWQMEGGEI | SMLEMFGTFA<br>........<br>........ | LSVGAAVGME<br>.MTQFL<br>.MTNFL | FWARWAHRAL<br>IVVATVLVME LTAYSVHRWI<br>IVVATVLVME LTAYSVHRWI |
| (SEQ ID No.8) | A.aurant. |  |  |  |  |  | ........ | ..ML.NSL | IVILSVIAME GIAAFTHRYI |
| (SEQ ID No.6) | E.herb. |  |  |  |  |  | ........ | ........ | IVFVTTVIGME VIAALAHKYI |
| (SEQ ID No.7) | E.ured. |  |  |  |  |  | ........ | .MLWIWNAL |  |
|  | Consensus | -------- | -------- | -------- | -------- | -------- | ---f---- | --v----ME | --A---Hr-- |
|  |  |  |  | Predicted TM helix |  |  |  |  |  |

|  |  |  |  |  |  |  |  |  | 224 |
|---|---|---|---|---|---|---|---|---|---|
| A.thal. | WHASL.WNMH | ESHHKPREGP | FELNDVFAIV | NAGPAIGLLS | YGFFNKGLVP | GLCFGAGLGI | TVFGIAYMFV | HDGLVHKRFP |
| Alical. | MHGPLGWGWH | KSHHEEHDHA | LEKNDLYGVV | FAVLATILFT | VGAYWMPVLM | WI....ALGW | TVYGLIYFIL | HDGLVHQRWP |
| A.aurant. | MHGPLGWGWH | KSHHEEHDHA | LEKNDLYGLV | FAVIATVLFT | VGWIWAPVLM | WI....ALGM | TVYGLIYFVL | HDGLVHQRWP |
| E.herb. | MHG.WGWRWH | ESHHTPRKGV | FELNDLFAVV | FAGVAIALIA | VGTAGVWPLQ | WI....GCGM | TVYGLLYFLV | HDGLVHQRWP |
| E.ured. | MHG.WGWGWH | LSHHEPRKGA | FEVNDLYAVV | FAALSILLIY | LGSTGMWPLQ | WI....GAGM | TAYGLLYFMV | HDGLVHQRWP |
| Consensus | -H-l-W---H | -SHH-pr-g- | fE-ND--a-- | -A--al-L-- | -------G-- | ------gl-G | -Tv-G--Y-- | -v HDGLVH-R-P |
|  |  |  |  |  | Predicted TM helix |  |  |  |

|  |  |  |  |  |  |  |  | 301 |
|---|---|---|---|---|---|---|---|---|
| A.thal. | VGPLADVPYL | RKVAAAHQLH | HT..DKFNGV | PYGLFLGPKE | LEEVGGNEEL | DKEISRRIKS | YKKASGSGSS SSS*... |
| Alical. | FRYIPRRGYF | RRLYQAHRLH | HAVEGRDHCV | SFGFIYAPP. | VDKLKQDLKR | SGVLRPQDER | PS*......... |
| A.aurant. | FRYIPRKGYA | RRLYQAHRLH | HAVEGRDHCV | SFGFIYAPP. | VDKLKQDLKM | SGVLRAEAQE | RT*......... |
| E.herb. | FHWIPRRGYL | KRLYVAHRLH | HAVRGREGCV | SFGFIYARK. | PADLQAILRE | RHGRPPKRDA | AKDRPDAASP SSSSPE* |
| E.ured. | FRYIPRKGYL | KRLYMAHRMH | HAVRGKEGCV | SFGFLYAPP. | LSKLQATLRE | RHG..ARAGA | ARDAQGGEDE PASGK*. |
| Consensus | ---I----Yl | r----AH-lH | H-------- | --V-----p- | -------G-- | ---------- | ---------- ---s--- |

Fig.7

(SEQ ID No.9)

```
  1 ccacgggtcc gcctccccgt ttttttccga tccgatctcc ggtgccgagg
 51 actcagctgt tgttcgcgc tttctcagcc gtcaccatga ccgattctaa
101 cgatgctgga atggatgctg ttcagagacg actcatgttt gaagacgaat
151 gcattctcgt tgatgaaaat aatcgtgtgg tgggacatga cactaagtat
201 aactgtcatc tgatggaaaa gattgaagct gagaatttac ttcacagagc
251 tttcagtgtg ttttattca actccaagta tgagttgctt ctccagcaac
301 ggtcaaaaac aaaggttact ttcccacttg tgtggacaaa cacttgttgc
351 agccatcctc tttaccgtga atccgagctt attgaagaga atgtgcttgg
401 tgtaagaaat gccgcacaaa ggaagctttt cgatgagctc ggtattgtag
451 cagaagatgt accagtcgat gagttcactc ccttgggacg catgctttac
501 aaggcacctt ctgatgggaa atggggagag cacgaagttg actatctact
551 cttcatcgtg cgggatgtga agcttcaacc aaacccagat gaagtggctg
601 agatcaagta cgtgagcagg gaagagctta aggagctggt gaagaaagca
651 gatgctggcg atgaagctgt gaaactatct ccatggttca gattggtggt
701 ggataatttc ttgatgaagt ggtgggatca tgttgagaaa ggaactatca
751 ctgaagctgc agacatgaaa accattcaca agctctgaac tttccataag
801 ttttggatct tccccttccc ataataaaat taagagatga gacttttatt
851 gattacagac aaaactggca acaaaatcta ttcctaggat ttttttttgc
901 tttttattta cttttgattc atctctagtt tagttttcat cttaaaaaaa
951 aaaa
```

Fig.8

(SEQ ID No.10)

```
  1  caccaatgtc tgtttcttct ttatttaatc tcccattgat tcgcctcaga
 51  tctctcgctc tttcgtcttc tttttcttct ttccGATTTG CCCATCGTCC
101  TCTGTCATCG ATTTCACCGA GAAAGTTACC GAATTTTCGT GCTTTCTCTG
151  GTACCGCTAT GACAGATACT AAAGATGCTG GTATGGATGC TGTTCAGAGA
201  CGTCTCATGT TTGAGGATGA ATGCATTCTT GTTGATGAAA CTGATCGTGT
251  TGTGGGGCAT GTCAGCAAGT ATAATTGTCA TCTGATGGAA AATATTGAAG
301  CCAAGAATTT GCTGCACAGG GCTTTTAGTG TATTTTTATT CAACTCGAAG
351  TATGAGTTGC TTCTCCAGCA AAGGTCAAAC ACAAAGGTTA CGTTCCCTCT
401  AGTGTGGACT AACACTTGTT GCAGCCATCC TCTTTACCGT GAATCAGAGC
451  TTATCCAGGA CAATGCACTA GGTGTGAGGA ATGCTGCACA AAGAAAGCTT
501  CTCGATGAGC TTGGTATTGT AGCTGAAGAT GTACCAGTCG ATGAGTTCAC
551  TCCCTTGGGA CGTATGCTGT ACAAGGCTCC TTCTGATGGC AAATGGGGAG
601  AGCATGAACT TGATTACTTG CTCTTCATCG TGCGAGACGT GAAGGTTCAA
651  CCAAACCCAG ATGAAGTAGC TGAGATCAAG TATGTGAGCC GGGAAGAGCT
701  GAAGGAGCTG GTGAAGAAAG CAGATGCAGG TGAGGAAGGT TTGAAACTGT
751  CACCATGGTT CAGATTGGTG GTGGACAATT TCTTGATGAA GTGGTGGGAT
801  CATGTTGAGA AAGGAACTTT GGTTGAAGCT ATAGACATGA AAACCATCCA
851  CAAACTCTGA ACATCTTTTT TTAAAGTTTT TAAATCAATC AACTTTCTCT
901  TCATCATTTT TATCTTTTCG ATGATAATAA TTTGGGATAT GTGAGACACT
951  TACAAAACTT CCAAGCACCT CAGGCAATAA TAAAGTTTGC GGCCGC
```

Fig.9

(SEQ ID No.11)

```
   1 CTCGGTAGCT GGCCACAATC GCTATTTGGA ACCTGGCCCG GCGCCACTCC
  51 GATGCCGCGA TGCTTCCTTC GTTGCTCAGA GGCCTCACGC ATATCCCCCG
 101 CGTGAACTCC GCCCAGCAGC CCAGCTGTGC ACACGCGCGA CTCCAGTTTA
 151 AGCTCAGGAG CATGCAGATG ACGCTCATGC AGCCCAGCAT CTCAGCCAAT
 201 CTGTCGCGCG CCGAGGACCG CACAGACCAC ATGAGGGGTG CAAGCACCTG
 251 GGCAGGCGGG CAGTCGCAGG ATGAGCTGAT GCTGAAGGAC GAGTGCATCT
 301 TGGTGSATGT TGAGGACAAC ATCACAGGCC ATGCCAGCAA GCTGGAGTGT
 351 CACAAGTTCC TACCACATCA SCCTGCAGGC CTGCTGCACC GGGCCTTCTC
 401 TGTGTTCCTG TTTGACGATC AGGGGCGACT GCTGCTGCAA CAGCGTGCAC
 451 GCTCAAAAAT CACCTTCCCA AGTGTGTGGA CGAACACCTG CTGCAGCCAC
 501 CCTTTACATG GGCAGACCCC AGATSAGGTG GACCAACTAA GCCAGGTGac
 551 CGACGSAACA GTACCTGGCG CAAAGGCTGC TGCCATCCGC AAGTTGGAGC
 601 ACGAGCTGGG GATACCAGCG CACCAGCTGC CGGCAAGCGC GTTTCSCTTC
 651 CTCACGCGTT TGCACTACTG TGCCGCGGAC GTGCAGCCAG CTGCGACACA
 701 ATCAGCGCTC TGGGGCGAGC ACGAAATGGA CTACATCTTG TTCATCCGGG
 751 CCAACGTCAC CTTGGCGCCC AACCCTGACG AGGTGGACGA AGTCAGGTAC
 801 GTGACGCAAG AGGAGCTGCG GCAGATGATG CAGCCGGACA ACGGGCTGCA
 851 ATGGTCGCCG TGGTTTCGCA TCATCGCCGC GCGCTTCCTT GAGCGTTGGT
 901 GGGCTGACCT GGACGCGGCC CTAAACACTG ACAAACACGA GGATTGGGGA
 951 ACGGTGCATC ACATCAACGA AGCGTGAAAG CACAACCTGC AGGATGTGAA
1001 GACACGTCAT GGGGTGGAAT TGCGTACTTG GCAGCTTCGT ATCTCCTTTT
1051 TCTGAGACTG AACCTGCAGT CAGGTCCCAC AAGGTCAGGT AAAATGGCTC
1101 GATAAAATGT ACCGTCACTT TTTGTCGCGT ATACTGAACT CCAAGAGGTC
1151 AAAAAAAAAA AAAAA
```

Fig.10

(SEQ ID No.12)

```
   1  CTCGGTAGCT  GGCCACAATC  GCTATTTGGA  ACCTGGCCCC  GCGCCAGTCC
  51  GATGCCGCGA  TGCTTCGTTC  GTTGCTCAGA  GGCCTCACGC  ATATCCCGCG
 101  CGTGAACTCC  GCCCAGCAGC  CCAGCTGTGC  ACACGCGCGA  CTCCAGTTTA
 151  AGCTCAGGAG  CATGCAGCTC  CTTTCCGAGG  ACCGCACAGA  CCACATGAGG
 201  GGTGCAAGCA  CCTGGGCAGG  CGGGCAGTCG  CAGGATGAGC  TGATGCTGAA
 251  GGACGAGTGC  ATCTTGGTAG  ATGTTGAGGA  CAACATCACA  GGCCATGCCA
 301  GCAAGCTGGA  GTGTCACAAG  TTCCTACCAC  ATCAGCCTGC  AGGCCTCCTG
 351  CACCGGGCCT  TCTCTGTGTT  CCTGTTTGAC  GATCAGGGGC  GACTGCTGCT
 401  GCAACAGCGT  GCACGCTCAA  AAATCACCTT  CCCAAGTCTG  TGGACGAACA
 451  CCTGCTGCAG  CCACCCTTTA  CATGCGCAGA  CCCCAGATGA  GGTGGACCAA
 501  CTAASCCAGG  TGGCCSACGG  AACAGTACCT  GGCGCAAAGG  CTGCTGCCAT
 551  CCGCAAGTTG  GAGCACSAGC  TGSGGATACC  AGCGCACCAS  CTCCCGGCAA
 601  GCGCGTTTCG  CTTCCTCACG  CGTTTGCACT  ACTGTGCCGC  GGACGTGCAG
 651  CCAGCTGCGA  CACAATCAGC  GCTCTGGSGC  GAGCACGAAA  TCGACTACAT
 701  CTTGTTCATC  CGGGCCAACG  TCACCTTGGC  GCCCAACCCT  GACGAGGTGG
 751  ACGAAGTCAG  GTACGTGACG  CAAGAGGAGC  TGCGGCAGAT  GATGCAGCCG
 801  GACAACGGGC  TTCAATGGTC  GCCGTGGTTT  CGCATCATCG  CCGCGCGCTT
 851  CCTTGAGCGT  TGGTGGGCTG  ACCTGGACGC  GGCCCTAAAC  ACTGACAAAC
 901  ACGAGGATTG  GGGAACGCTG  CATCACATCA  ACGAAGCGTG  AAGGCAGAAG
 951  CTGCAGGATG  TGAAGACACG  TCATGGGGTG  GAATTGCGTA  CTTGGCAGCT
1001  TCGTATCTCC  TTTTTCTGAG  ACTGAACCTG  CAGAGCTAGA  GTCAATGGTG
1051  CATCATATTC  ATCGTCTCTC  TTTTGTTTTA  GACTAATCTG  TAGCTAGAGT
1101  CACTGATGAA  TCCTTTACAA  CTTTCAAAAA  AAAAA
```

Fig.11

```
SEQ ID Nos.
             1                                                                    50
(14)   HPO4  MLRSLLRGLT HIPRVNSAQQ PSCAHARLQF KLRSMQMTLM QPSISANLSR
(15)   HPO5  MLRSLLRGLT HIPRVNSAQQ PSCAHARLQF KLRSMQLL.. ..........
(16)   ATDP7 MSVSSLFNLP .LIRLRSLA. LSSSFSSFRF AHRPLSSIS. PRKLPNFRAF
(17) C. brew MS-SSMLNFT .ASRIVSLPL LSSPPSRVHL PLCFFSPISL TQRFSAKLTF
(18)   ATDP5 .......... .TGPPPRFFP IRSPVPRTQL FVRAFSAV.. ..........
(19) S. cerev. ..MTADNNSM PHGAVSSYAK LVQNQTPEDI LEEFPEIIPL QQRPN...TR 51                                                                  100
             AEDRTDHMRG ASTWAGGQSQ DELMLKDECI LVDVEDNITG HASKLECHKF
             SEDRTDHMRG ASTWAGGQSQ DELMLKDECI LVDVEDNITG HASKLECHKF
             S..GTA.MTD TKDAGMDAVQ RRLMFEDECI LVDETDRVVG HVSKYNCHLM
             SSQATT.MGE VVDAGMDAVQ RRLMFEDECI LVDENDKVVG HESKYNCHLM
             .....T.MTD SNDAGMDAVQ RRLMFEDECI LVDENNRVVG HDTKYNCHLM
             SSETSNDESG ETCFSGHDEE QIKLMNENCI VLDWDDNAIG AGTKKVCHLM 101                                                                 150
             LPHQPAGLLH RAFSVFLFDD QGRLLLQQRA RSKITFPSVT TNTCCSHPLH
             LPHQPAGLLH RAFSVFLFDD QGRLLLQQRA RSKITFPSVW TNTCCSHPLH
             ENIEAKNLLH RAFSVFLFNS KYELLLQQRS NTKVTFPLVW TNTCCSHPLY
             EKIESENLLH RAFSVFLFNS KYELLLQQRS ATKVTFPLVW TNTCCSHPLY
             EKIEAENLLH RAFSVFLFNS KYELLLQQRS KTKVTFPLVW TNTCCSHPLY
             ENIE-KGLLH RAFSVFIFNE QGELLLQQRA TEKITFPDLW TNTCCSHPLC 151                                                                 200
             GQTPDEVDQL SQVADGTVPG AKAAAIRKLE HELGIPAHQL PA.SAFRFLT
             GQTPDEVDQL SQVADGTVPG AKAAAIRKLE HELGIPAHQL PA.SAFRFLT
             RE........ SELIQDNALG VRNAAQRKLL DELGIVAEDV PV.DEFTPLG
             RE........ SELIDENCLG VRNAAQRKLL DELGIPAEDL PV.DQFIPLS
             RE........ SELIEENVLG VRNAAQRKLF DELGIVAEDV PV.DEFTPLG
             ID...DELGL KGKLDDKIKG AITAAVRKLD HELGIPEDET KTRGKFHFLN 201                                                                 250
             RLHYCAADVQ PAATQSALWG EHEMDYILFI ....RANVTL APNPDEVDEV
             RLHYCAADVQ PAATQSALWG EHEMDYILFI ....RANVTL APNPDEVDEV
             RMLY...... .KAPSDGKWG EHELDYLLFI ....VRDVKV QPNPDEVAEI
             RILY...... .KAPSDGKWG EHELDYLLFI ....IRDVNL DPNPDEVAEV
             RMLY...... .KAPSDGKWG EHEVDYLLFI ....VRDVKL QPNPDEVAEI
             RIHY...... .MAPSNEPWG EHEIDYILFY KINAKENLTV NPNVNEVRDF 251                                                                 300
             RYVTQEELRQ MMQ....PDN GLQWSPWFRI IAARFLERWW ADLDAALNTD
             RYVTQEELRQ MMQ....PDN GLQWSPWFRI IAARFLERWW ADLDAALNTD
             KYVSREELKE LVKKADAGEE GLKLSPWFRL VVDNFLMKWW DHVEKGTLVE
             KYMNRDDLKE LLRKADAEEE GVKLSPWFRL VVDNFLFKWW DHVEKGSLKD
             KYVSREELKE LVKKADAGDE AVKLSPWFRL VVDNFLMKWW DHVEKGTITE
             KWVSPNDLKT MF.....ADP SYKFTPWFKI ICENYLFNWW EQLDDLSEVE 301
             KHEDWGTVHH INEA*
             KHEDWGTVHH INEA*
             A.IDMKTIHK L*
             A.ADMKTIHK L*
             A.ADMKTIHK L*
             NDRQ...IHR ML*
```

Fig.12

(SEQ ID No.13)

```
  1  ccaaaaacaa ctcaaatctc ctccgtcgct cttactccgc catgggtgac
 51  gactccggca tggatgctgt tcagcgacgt ctcatgtttg acgatgaatg
101  cattttggtg gatgagtgtg acaatgtggt gggacatgat accaaataca
151  attgtcactt gatggagaag attgaaacag gtaaaatgct gcacagagca
201  ttcagcgttt ttctattcaa ttcaaaatac gagttacttc ttcagcaacg
2S1  gtctgcaacc aaggtgacat ttcctttagt atggaccaac acctgttgca
301  gccatccact ctacagagaa tccgagcttg ttcccgaaac gcctgagaga
351  atgctgcaca gaggaxxxxx xxxxxxxxxx xxxxxxxxxx xxxxxxxxxx
401  xxxxxxxxxx xxxxxxxxxx xxxxxxxxxx xxxxxxxxxx xxxxxxxxxx
451  xxxxxxxxxx xxxxxxxxxx xxxxxxxxxx xxxxxxxxxx xxxxxxxxxx
501  xxxxxxxxxx xxxxxxxxxx xxxxxxxxxx xxxxxxxxxx xxxxxxxxxx
551  xxxxxxxxxx xxxxxxxxxx xxxxxxxxxx xxxxxxxxxx xxxxxxxxxx
601  xxxxxxxxxx xxxxxxxxxx xxxxxxxxxx xxxxxxxxxx xxxxxxxxxx
651  xxxxxxxxxx xxxxxxxxxx xxxxxxxxxx tcatgtgcaa aagggtacac
701  tcactgaatg caatttgata tgaaaaccat acacaagctg atatagaaac
751  acaccctcaa ccgaaaagca agcctaataa ttcgggttgg gtcgggtcta
801  ccatcaattg ttttttttctt ttaacaactt ttaatctcta tttgagcatg
851  ttgattcttg tcttttgtgt gtaagatttt gggtttcgtt tcagttgtaa
901  taatgaacca ttgatggttt gcaatttcaa gttcctatcg acatgtagtg
951  atctaaaaaa
```

Fig.13

```
     SEQ ID Nos.
          1                                                                                              70
  (20) Plant beta  ..........  ...MDTLLkT  PN-LeFl-p-  -HG.....F-  vk.-S-f-s-  k---fG--K-  Ce--g---vc
  (21)A.t. epsilon MECVGARNFA  AMAVSTFPSW  SCRRKFPVVK  RYSYRNIRFG  LCSVRASGGG  SSGSESCVAV  REDFADEEDF
        Consensus ----------  -----T----  -----F----  --------F-  ----------  ----------  -E--------

Cyanobacterial enzyme begins ────┐
         71                                          ▼                                               140
      Plant beta  vk--SsALLe  LVPETKKENL  DFELPmYDp.  ...S.Kg-VV  DLAvVGGGPA  GLAVAQQVSE  AGLSVcSIDP
     A.t. epsilon VKAGGSEIL.  FVQMQQNKDM  DEQSKLVDKL  PPISIGDGAL  DHVVIGCGPA  GLALAAESAK  LGLKVGLIGP
        Consensus VK---S--L-  -V--------  D------D--  ---S------  D--V-G-GPA  GLA-A-----  -GL-V--I-P
              Possible subunit interaction domain       ↑Dinucleotide-binding signature↑

141                                                                                        210
      Plant beta  .-PKLIWPNN  YGVWVDEFEA  MDLLDCLDaT  WSGa-VYiDd  -t-KDL-RPY  GRVNRKQLKS  KMmQKCI-NG
     A.t. epsilon DLP...FTNN  YGVWEDEFND  LGLQKCIEHV  WRETIVYLDD  DKPITIGRAY  GRVSRRLLHE  ELLRRCVESG
        Consensus --P-----NN  YGVW-DEF--  --L--C----  W----VY-DD  -------R-Y  GRV-R--L--  -----C---G
                                              Conserved region #1

211                                                                                        280
      Plant beta  VKFHqaKViK  ViHE.E-kSm  liCnDG-tIQ  AtVVLDATGF  SR-.LVQYDK  PYnPGY.QVA  YGIlAEVeeH
     A.t. epsilon VSYLSSKVDS  ITEASDGLRL  VACDDNNVIP  CRLATVASGA  ASGKLLQYEV  GGPRVCVQTA  YGVEVEVENS
        Consensus V-----KV--  ----------  --C-D---I-  ------A-G-  ----L-QY--  -------Q-A  YG---EV---

281                                                                                        350
      Plant beta  PFD--KMVfM  DWRDsHL-nn  -eLKERNs-i  PTFLYAMPFS  SNrIFLEETS  LVARPGLrmd  DIQERMvARL
     A.t. epsilon PYDPDQMVFM  DYRDY..TNE  .KVRSLEAEY  PTFLYAMPMT  KSRLFFEETC  LASKDVMPFD  LLKTKLMLRL
        Consensus P-D---MVFM  D-RD----N-  ----------  PTFLYAMP--  --R-F-EET-  L--------D  --------RL
                        ↑ Conserved region #2          ↑ Conserved region #3          ↑

351                                                                                        420
      Plant beta  -HLGIkVKsI  EEDEhCvIPM  GGpLPVlPQR  VVGiGGTAGm  VHPSTGYMVA  RTLAAAPvVA  NAIi-YLgSe
     A.t. epsilon DTLGIRILKT  YEEEWSYIPV  GGSLPNTEQK  NLAFGAAASM  VHPATGYSVV  RSLSEAPKYA  SVIAEILREE
        Consensus --LGI-----  -E-E---IP-  GG-LP---Q-  ----G--A-M  VHP-TGY-V-  R-L--AP--A  --I---L--E
                                                ↑ Conserved region #4      Predicted TM helix 421                                                                                        480
      Plant beta  -s-s..G-eL  SaeVWkDLWP  IERRRQREFF  CFGMDILLKL  DLpATRRFFD  AFFDLePrYW
     A.t. epsilon TTKQINSN.I  SRQAWDTLWP  PERKRQRAFF  LFGLALIVQF  DTEGIRSFFR  TFFRLPKWMW
        Consensus ----------  S---W--LWP  -ER-RQR-FF  -FG-------  D----R-FF-  -FF-L----W
                               ↑ Conserved region #5                                      ↑

481                                           533
      Plant beta  HGFLSSRLfL  PELivFGLSL  FShASNTSR-  EIMTK.GT-P  Lv-MINNLlQ  D-e
     A.t. epsilon QGFLGSTLTS  GDLVLFALYM  FVISPNNLRK  GLINHLISDP  TGATMIKTYL  KV.
        Consensus -GFL-S-L--  --L--F-L--  F----N--R-  ----------  ----------  ---
                                          Predicted TM helix
```

FIG.14

Adonis palaestina ε-cyclase cDNA #5   Length: 1898

SEQ ID No.22

```
   1  aaaggagtgt tctattaatg ttactgtcgc attcttgcaa cacttatatt
  51  caaactccat tttcttcttt tctcttcaaa acaacaaact aatgtgagca
 101  gagtatctgg ctatggaact acttggtgtt cgcaacctca tctcttcttg
 151  ccctgtgtgg acttttggaa caagaaacct tagtagttca aaactagctt
 201  ataacataca tcgatatggt tcttcttgta gagtagattt caagtgaga
 251  gctgatggtg aagcgggag tagaagttct gttgcttata aagagggttt
 301  tgtggatgaa gaggatttta tcaaagctgg tggttctgag cttttgtttg
 351  tccaaatgca gcaaacaaag tctatggaga aacaggccaa gctcgccgat
 401  aagttgccac caataccttt tggagaatcc gtgatggact tggttgtaat
 451  aggttgtgga cctgctggtc tttcactggc tgcagaagct gctaagctag
 501  ggttgaaagt tggcctatt ggtcctgatc ttccttttac aaataattat
 551  ggtgtgtggg aagacgagtt caaagatctt ggacttgaac gttgtatcga
 601  gcatgcttgg aaggacacca tcgtatatct tgataatgat gctcctgtcc
 651  ttattggtcg tgcatatgga cgagttagtc gacatttgct acatgaggag
 701  ttgctgaaaa ggtgtgtgga gtcaggtgta tcatatctgg attctaaagt
 751  ggaaaggatc actgaagctg gtgatggcca tagccttgta gtttgtgaaa
 801  atgagatctt tatcccttgc aggcttgcta ctgttgcatc tggagcagct
 851  tcagggaaac ttttggagta tgaagtaggt ggccctcgtg tttgtgtcca
 901  aaccgcttat ggggtggagg ttgaggtgga gaacaatcca tacgatccca
 951  acttaatggt attcatggac tacagagact atatgcaaca gaaattacag
1001  tgctcggaag aagaatatcc aacatttctC tatgtcatgc ccatgtcgcc
1051  aacaagactt ttttttgagg aaacctgttt ggcctcaaaa gatgccatgc
1101  cattcgatct actgaagaga aaactgatgt cacgattgaa gactctgggt
1151  atccaagtta caaaagttta tgaagaggaa tggtcatata ttcctgttgg
1201  tggttcttta ccaaacacag agcaaagaa cctagcattt ggtgctgcag
1251  caagcatggt gcatccagca acaggctatt cggttgtacg gtcactgtca
1301  gaagctccaa aatatgcttc tgtaattgca aagattttga agcaagataa
1351  ctctgcgtat gtggtttctg gacaaagtag tgcagtaaac attttcaatgc
1401  aagcatggag cagtctttgg ccaaaggagc gaaaacgtca aagagcatTc
1451  tttctttttTg gattagagct tattgtgcag ctagatattg aagcaaccag
1501  aacattcttt agaaccttct tccgcttgcc aacttggatg tggtggggtt
1551  tccttgggtc ttcactatca tctttcgatc tcgtcttgtt ttccatgtac
1601  atgtttgttt tggcgccaaa cagcatgagg atgtcacttg tgagacattt
1651  gcttcagat cctctggtg cagttatggt aagagcttac ctcgaaaggt
1701  agtctcatct attattaaac tctagtgttt caccaaataa atgaggatcc
1751  ttcgaatgtg tatatgatca tctctatgta tatcctgtac tctaatctca
1801  taaagtaaat gccgggtttg atattgttgt gtcaaaccgg ccaatgatat
1851  aaagtaaatt tattgataca aaagtagttt ttttccttaa aaaaaaaa
```

Adonis palaestina ε-cyclase #5 predicted polypeptide
TRANSLATE  from: 113 to: 1702  Length: 529 amino acids SEQ ID No.23

```
   1  MELLGVRNLI SSCPVWTFGT RNLSSSKLAY NIHRYGSSCR VDFQVRADGG
  51  SGSRSSVAYK EGFVDEEDFI KAGGSELLFV QMQQTKSMEK QAKLADKLPP
 101  IPFGESVMDL VVIGCGPAGL SLAAEAAKLG LKVGLIGPDL PFTNNYGVWE
 151  DEFKDLGLER CIEHAWKDTI VYLDNDAPVL IGRAYGRVSR HLLHEELLKR
 201  CVESGVSYLD SKVERITEAG DGHSLVVCEN EIFIPCRLAT VASGAASGKL
 251  LEYEVGGPRV CVQTAYGVEV EVENNPYDPN LMVFMDYRDY MQQKLQCSEE
 301  EYPTFLYVMP MSPTRLFFEE TCLASKDAMP FDLLKRKLMS RLKTLGIQVT
 351  KVYEEEWSYI PVGGSLPNTE QKNLAFGAAA SMVHPATGYS VVRSLSEAPK
 401  YASVIAKILK QDNSAYVVSG QSSAVNISMQ AWSSLWPKER KRQRAFFLFG
 451  LELIVQLDIE ATRTFFRTFF RLPTWMWWGF LGSSLSSFDL VLFSMYMFVL
 501  APNSMRMSLV RHLLSDPSGA VMVRAYLER*
```

Fig.15A

DNA sequence of potato cDNA (GenBank R27545) obtained from Nicholas
J.Provart potato.seq  Length: 1378  August 2, 1996 13:06  Type: N
Check: 605..

SEQ ID No.24

```
   1 tagcggnnnn naggatgagt tcaaagatct tggtcttcaa gcctgcattg
  51 aacatgtttg gcgggatacc attgtatatc ttgatgatga tgatcctatt
 101 cttattggcc gtgcctatgg aagagttagt cgccatttac tgcacgagga
 151 gttactcaaa aggtgtgtgg aggcaggtgt tttgtatcta aactcgaaag
 201 tggataggat tgttgaggcc acaaatggcc acagtcttgt agagtgcgag
 251 ggtgatgttg tgattccctg caggtttgtg actgttgcat cgggagcagc
 301 ctcggggaaa ttcttgcagt atgagttggg aggtcctaga gtttctgttc
 351 aaacagctta tggagtggaa gttgaggtcg ataacaatcc atttgacccg
 401 agcctgatgg ttttcatgga ttatagagac tatgtcagac acgacgctca
 451 atctttagaa gctaaatatc caacatttct ctatgccatg cccatgtctc
 501 caacacgagt cttttttcgag gaaacttgtt tggcttcaaa agatgcaatg
 551 ccattcgatc tgttaaagaa aaaattgatg ttacgattga cacccctcgg
 601 tgtaagaatt aaagaaattt atgaggagga atggtcttac ataccagttg
 651 gaggatcttt gccaaataca gaacaaaaaa cacttgcatt tggtgctgct
 701 gctagcatgg ttcatccagc cacaggttat tcagtcgtca gatcactgtc
 751 tgaagctcca aaatgcgcct tcgtgcttgc aaatatatta cgacaaaatc
 801 atagcaagaa tatgcttact agttcaagta ccccgagtat ttcaactcaa
 851 gcttggaaca ctctttggcc acaagaacga aaacgacaaa gatcgttttt
 901 cctatttgga ctggctctga tattgcagct ggatattgag gggataaggt
 951 cattttccg cgcgttcttc cgtgtgccaa aatggatgtg gcagggattt
1001 cttggttcaa gtctttcttn agcagacctc atgttatttg ccttctacat
1051 gtttattatt gcaccaaatg acatgagaag aggcttaatc agacatcttt
1101 tatctgatcc tactggtgca acattgataa gaacttatct tacattttag
1151 agtaaattcc tcctacaata gttgttgaan nagaggcctc attacttcag
1201 attcataaca gaaatcgcgg tctctcgagg ccttgtatat aacattttca
1251 ctaggttaat attgcttgaa taagttgcac agtttcagtt tttgtatctg
1301 cttctttttt gtccaagatc atgtattgan ccaatttata tacattgcca
1351 gtatatataa attttataaa aaaaaaaa
``` poteps.pep  Length: 378  TRANSLATE from: 14 to: 1147

SEQ ID No. 25

```
  1 DEFKDLGLQA CIEHVWRDTI VYLDDDDPIL IGRAYGRVSR HLLHEELLKR
 51 CVEAGVLYLN SKVDRIVEAT NGHSLVECEG DVVIPCRFVT VASGAASGKF
101 LQYELGGPRV SVQTAYGVEV EVDNNPFDPS LMVFMDYRDY VRHDAQSLEA
151 KYPTFLYAMP MSPTRVFFEE TCLASKDAMP FDLLKKKLML RLNTLGVRIK
201 EIYEEEWSYI PVGGSLPNTE QKTLAFGAAA SMVHPATGYS VVRSLSEAPK
251 CAFVLANILR QNHSKNMLTS SSTPSISTQA WNTLWPQERK RQRSFFLFGL
301 ALILQLDIEG IRSFFRAFFR VPKWMWQGFL GSSLSXADLM LFAFYMFIIA
351 PNDMRRGLIR HLLSDPTGAT LIRTYLTF*
```

Fig.15B

Chimeric lettuce/potato lycopene ε-cyclase: converts lycopene to δ-carotene, the lettuce cDNA converts lycopene to ε-carotene and the potato cDNA does not produce an active enzyme
(amino acids in lower case are from lettuce and those in uppercase are from the potato cDNA; an AvaII site in common to the two cDNAs was used to construct the chimera)

SEQ ID No.26
```
  1  mecfgarnmt atmavftcpr ftdcnirhkf sllkqrrftn lsassslrqi
 51  kcsaksdrcv vdkqgisvad eedyvkaggs elffvqmqrt ksmesqskls
101  eklaqipign cildlvvigc gpaglalaae saklglnvgl igpdlpftnn
151  ygvwqdefig lglegciehs wkdtlvyldd adpirigray grvhrdllhe
201  ellrrcvesg vsylsskver iteapngysl iecegnitip crlatvasga
251  asgkfleyel gGPRVSVQTA YGVEVEVDNN PFDPSLMVFM DYRDYVRHDA
301  QSLEAKYPTF LYAMPMSPTR VFFEETCLAS KDAMPFDLLK KKLMLRLNTL
351  GVRIKEIYEE EWSYIPVGGS LPNTEQKTLA FGAAASMVHP ATGYSVVRSL
401  SEAPKCAFVL ANILRQNHSK NMLTSSSTPS ISTQAWNTLW PQERKRQRSF
451  FLFGLALILQ LDIEGIRSFF RAFFRVPKWM WQGFLGSSLS XADLMLFAFY
501  MFIIAPNDMR RGLIRHLLSD PTGATLIRTY LTF*
```

Fig.16

```
GAP comparison of Arabidopsis ε-cyclase (SEQ ID No.27) x potato
ε-cyclase (SEQ ID No.25) (partial)
blosum62.cmp    Gap Weight:      12      Average Match:    2.912
Length Weight:   4   Average Mismatch: -2.003
       Quality:  1485              Length:       529
         Ratio:  3.929               Gaps:         1
Percent Similarity: 79.893   Percent Identity: 76.139
Match display thresholds for the alignment(s):  | = IDENTITY   : = 2   . = 1

151 EDEFNDLGLQKCIEHVWRETIVYLDDDKPITIGRAYGRVSRRLLHEELLR 200 → SEQ ID No.27
     ||| ||||| |||||||:|||||||| || |||||||||| |||||||:
   1 .DEFKDLGLQACIEHVWRDTIVYLDDDDPILIGRAYGRVSRHLLHEELLK  49 → SEQ ID No.25

201 RCVESGVSYLSSKVDSITEASDGLRLVACDDNNVIPCRLATVASGAASGK 250
     ||||.|| ||.|||| | ||..| || |: . ||||| |||||||||||
  50 RCVEAGVLYLNSKVDRIVEATNGHSLVECEGDVVIPCRFVTVASGAASGK  99

251 LLQYEVGGPRVCVQTAYGVEVEVENSPYDPDQMVFMDYRDYTNEKVRSLE 300
     ||||.||||| |||||||||||||:|.|:|| |||||||| .|||
 100 FLQYELGGPRVSVQTAYGVEVEVDNNPFDPSLMVFMDYRDYVRHDAQSLE 149

301 AEYPTFLYAMPMTKSRLFFEETCLASKDVMPFDLLKTKLMLRLDTLGIRI 350
     |.|||||||||. .|.|||||||||| |||||| ||||||.|||:||
 150 AKYPTFLYAMPMSPTRVFFEETCLASKDAMPFDLLKKKLMLRLNTLGVRI 199

351 LKTYEEEWSYIPVGGSLPNTEQKNLAFGAAASMVHPATGYSVVRSLSEAP 400
     . ||||||||||||||||||||| |||||||||||||||||||||||||
 200 KEIYEEEWSYIPVGGSLPNTEQKTLAFGAAASMVHPATGYSVVRSLSEAP 249

401 KYASVIAEILREETTKQI.....NSNISRQAWDTLWPPERKRQRAFFLFG 445
     | | |:| |||: .| .    .|| |||.|||| ||||||.|||||
 250 KCAFVLANILRQNHSKNMLTSSSTPSISTQAWNTLWPQERKRQRSFFLFG 299

446 LALIVQFDTEGIRSFFRTFFRLPKWMWQGFLGSTLTSGDLVLFALYMFVI 495
     ||||.| | ||||||||| |||.|||||||||.|.  ||.||| |||:|
 300 LALILQLDIEGIRSFFRAFFRVPKWMWQGFLGSSLSXADLMLFAFYMFII 349

496 SPNNLRKGLINHLISDPTGATMIKTYLKV 524
     .||.:|:||| ||:|||||||:|||:|||
 350 APNDMRRGLIRHLLSDPTGATLIRTYLTF 378
```

Fig.17A

*Adonis palaestina Ipi1*

SEQ ID No.28
```
   1  attcatcttc agcagcgctg tcgtactctt tctatatctt cttccatcac
  51  taacagtagt cgccgacggt tgaatcggct attcgcctca acgtcaacta
 101  tgggtgaagt cactgatgct ggaatggatg ctgttcagaa gcggctcatg
 151  ttcgacgacg aatgtatttt ggtggatgag aatgacaagg tcgtcgggca
 201  tgattccaaa tacaactgtc atttgatgga aaagatagag cagaaaatt
 251  tgcttcacag agccttcagt gttttcttgt tcaactcaaa atatgaattg
 301  cttcttcagc aacgatccgc cacaaaggta acattcccgc tcgtatggac
 351  aaacacatgt tgcagtcatc ctctctttcg tgattccgag ctcatagaag
 401  aaaattatct cggtgtacga aacgctgcac aaagaaagct tttagacgag
 451  ctaggcattc cagctgaaga tgtcccagtt gatgaattta ctcctcttgg
 501  tcgcattctt tacaaagctc catctgacgg caaatgggga gagcacgaat
 551  tggactatct cctatttatt gtccgagatg tgaaatacga tccaaaccca
 601  gatgaagttg ctgatgctaa gtatgttaat cgcgaggagt tgagagagat
 651  actgagaaaa gctgatgctg gtgaagaggg actcaagttg tctccttggt
 701  ttagattggt tgttgataac ttttttgttca agtggtggga tcatgtagag
 751  cagggtacga ttaaggaagt tgctgacatg aaaactatcc acaagttgac
 801  ttaagaggac ttctctcctc tgttctacta tttgtttttt gctacaataa
 851  gtgggtggtg ataagcagtt tttctgtttt ctttaattta tggcttttga
 901  atttgcctcg atgttgaact tgtaacatat ttagacaaat atgagacctt
 951  gtaagttgaa tttgaggctg aatttatatt tttgggaaca taataatgtt
1001  aa
```

Fig.17B

Adonis palaestina Ipi2

SEQ ID No.29

```
   1  ttttaaagct ctttcgctcc accaccatca aagccagcca aatttctctg
  51  tacaaaagtt aaaaacaccg ctttgggctt tggcccctcc atatcggaat
 101  ccttgtttac gatacgcatc taaaccagta attctcggtt ttaatttgtt
 151  tcctaaatta ggcccctttc cggaatcccg agaattatgt cgtcgatcag
 201  gattaatcct ttatatagta tcttctccac caccactaaa acattatcag
 251  cttcgtgttc ttctcccgct gttcatcttc agcagcgttg tcgtactctt
 301  tctatttctt cttccatcac taacagtcct cgccgagggt tgaatcggct
 351  gttcgcctca acgtcgacta tgggtgaagt cgctgatgct ggtatggatg
 401  ccgtccagaa gcggcttatg ttcgacgatg aatgtatttt ggtggatgag
 451  aatgacaagg tcgtcggaca tgattccaaa tacaactgtc atttgatgga
 501  aaagatagag gcagaaaact tgcttcacag agccttcagt gttttcttat
 551  tcaactcaaa atacgagttg cttcttcagc aacgatctgc aacgaaggta
 601  acattcccgc tcgtatggac aaacacctgt tgcagccatc ccctcttccg
 651  tgattccgaa ctcatagaag aaaattttct cggggtacga aacgctgcac
 701  aaaggaagct tttagacgag ctaggcattc cagctgaaga cgtaccagtt
 751  gatgaattca ctcctcttgg tcgcattctt tacaaagctc catctgacgg
 801  aaaatgggga gagcacgaac tggactatct tctgtttatt gtccgagatg
 851  tgaaatacga tccaaaccca gatgaagttg ctgacgctaa gtacgttaat
 901  cgcgaggagt tgaaagagat actgagaaaa gctgatgcag gtgaagaggg
 951  aataaagttg tctccttggt ttagattggt tgtggataac ttttgttca
1001  agtggtggga tcatgtagag gaggggaaga ttaaggacgt cgccgacatg
1051  aaaactatcc acaagttgac ttaagagaaa gtctcttaag ttctactatt
1101  tggtttttgc ttcaataagt ggatggtgat gagcagtttt tatgcttcct
1151  ttaattttgg cttttcaatt tgctttatgt gttgaacttg taacatattt
1201  agtcaaatat gagaccttgt gagttgaatt tgaggttata tttatagttt
1251  tgggaacata aaaaaaaaaa
```

Fig.18A

*Haematococcus pluvialis Ipi1*

SEQ ID No.11

```
   1  ctcggtagct ggccacaatc gctatttgga acctggcccg gcggcagtcc
  51  gatgccgcga tgcttcgttc gttgctcaga ggcctcacgc atatcccccg
 101  cgtgaactcc gcccagcagc ccagctgtgc acacgcgcga ctccagttta
 151  agctcaggag catgcagatg acgctcatgc agcccagcat ctcagccaat
 201  ctgtcgcgcg ccgaggaccg cacagaccac atgaggggtg caagcacctg
 251  ggcaggcggg cagtcgcagg atgagctgat gctgaaggac gagtgcatct
 301  tggtggatgt tgaggacaac atcacaggcc atgccagcaa gctggagtgt
 351  cacaagttcc taccacatca gcctgcaggc ctgctgcacc gggccttctc
 401  tgtgttcctg tttgacgatc aggggcgact gctgctgcaa cagcgtgcac
 451  gctcaaaaat caccttccca agtgtgtgga cgaacacctg ctgcagccac
 501  cctttacatg ggcagacccc agatgaggtg gaccaactaa gccaggtggc
 551  cgacggaaca gtacctggcg caaaggctgc tgccatccgc aagttggagc
 601  acgagctggg gataccagcg caccagctgc cggcaagcgc gtttcgcttc
 651  ctcacgcgtt tgcactactg tgccgcggac gtgcagccag ctgcgacaca
 701  atcagcgctc tggggcgagc acgaaatgga ctacatcttg ttcatccggg
 751  ccaacgtcac cttggcgccc aaccctgacg aggtggacga agtcaggtac
 801  gtgacgcaag aggagctgcg gcagatgatg cagccggaca acgggctgca
 851  atggtcgccg tggtttcgca tcatcgccgc gcgcttcctt gagcgttggt
 901  gggctgacct ggacgcggcc ctaaacactg acaaacacga ggattgggga
 951  acggtgcatc acatcaacga agcgtgaaag cagaagctgc aggatgtgaa
1001  gacacgtcat ggggtggaat tgcgtacttg gcagcttcgt atctcctttt
1051  tctgagactg aacctgcagt caggtcccac aaggtcaggt aaaatggctc
1101  gataaaatgt accgtcactt tttgtcgcgt atactgaact ccaagaggtc
1151  aaaaaaaaaa aaaaa
```

Fig.18B

*Haematococcus pluvialis* Ipi2

SEQ ID No.30

```
   1  tggaacctgg cccggcggca gtccgatgcc gcgatgcttc gttcgttgct
  51  cagaggcctc acgcatatcc cgcgcgtgaa ctccgcccag cagcccagct
 101  gtgcacacgc gcgactccag tttaagctca ggagcatgca gctgcttgcc
 151  gaggaccgca cagaccacat gagggtgcaa agcacctggg caggcgggca
 201  gtcgcaggat gagctgatgc tgaaggacga gtgcatctta gtggatgctg
 251  acgacaacat cacaggccat gccagcaagc tggagtgcca caaattccta
 301  ccacatcagc ctgcaggcct gctgcaccgg gccttctctg tgttcctgtt
 351  tgacgaccag gggcgactgc tgctgcaaca gcgtgcacgc tcaaaaatca
 401  ccttcccaag tgtgtggacg aacacctgct gcagccaccc tctacatggg
 451  cagaccccag atgaggtgga ccaactaagc caggtggccg acggcacagt
 501  acctggcgca aaagctgctg ccatccgcaa gttggagcac gagctgggga
 551  taccagcgca ccagctgccg gcaagcgcgt ttcgcttcct cacgcgtttg
 601  cactactgtg ccgcggacgt gcagccggct gcgacacaat cagcgctctg
 651  gggcgagcac gagatggact acatcttatt catccgggcc aacgtcacct
 701  tggcgcccaa ccctgacgag gtggacgaag tcaggtacgt gacgcaagag
 751  gagctgcggc agatgatgca gccggacaac gggttgcaat ggtcgccgtg
 801  gtttcgcatc atcgccgcgc gcttccttga gcgttggtgg gctgacctgg
 851  acgcggccct aaacactgac aaacacgagg attggggaac ggtgcatcac
 901  atcaacgaag cgtgaaggca gaagctgcag gatgtgaaga cacgtcatgg
 951  ggtggaattg cgtacttggc agcttcgtat ctccttttc tgagactgaa
1001  cctgcagagc tagagtcaat ggtgcatcat attcatcgtc tctcttttgt
1051  tttagactaa tctgtagcta gagtcactga tgaatccttt acaactttca
1101  aaaaaaaaa
```

Fig.19A

*Lactuca sativa* Ipi1

SEQ ID No.31
```
  1 tgccaaaatg ttgaaatttc cccttttaa aaccattgct accatgatct
 51 cttctccata ttcttccttc ttgctgcctc ggaaatcttc tttccctcca
101 atgccgtctc tcgcagccgc tagtgttttc ctccaccctc tttcgtctgc
151 cgctatgggc gattccagca tggatgctgt ccagcgacgt ctcatgttcg
201 atgacgaatg cattttggtg gatgagaatg acaaagtggt tggccatgat
251 actaaataca attgtcattt gatggagaag attgaaaagg gaaatatgct
301 acacagagca ttcagtgtgt tcttgttcaa ctcgaaatat gaattactcc
351 ttcagcaacg ttctgcaacc aaggtgactt tcccttggt atggacaaac
401 acgtgttgca gccatccact atacagggag agtgagctta ttgacgaaaa
451 cgcccttggg gtgaggaatg ctgcacagag gaagctcctg gatgaactcg
501 gcatccctgg agcagatgtt ccggttgatg agttcactcc attgggtcgc
551 attctataca aggccgcatc ggatggaaag tggggagaac atgaacttga
601 ttacctgctg tttatggtac gtgatgttgg tttggatccg aacccagatg
651 aagtgaaaga tgtaaaatat gtgaaccggg aagagctgaa ggaattggta
701 aggaaggcgg atgctggtga agagggtgtg aagctgtccc cgtggttcaa
751 attgattgtc gataatttct tgtttcagtg gtgggatcga ctccataagg
801 gaaccctaac cgaagctatt gatatgaaaa caatccacaa actcacataa
851 aaacactaca ctagtaggag agaggattat atgagatatt tgttatatgt
901 gaaattgaaa ttcagatgaa tgcttgtatt tatttctatt tggacaaact
951 tcaacttctt tttgctacct tatcagaaaa aaaaa
```

Fig.19B

Lactuca sativa Ipi2

SEQ ID No.32
```
   1  tattcgcttc aaaatctctt ccattaactg ctcaaatctc caccttcgcc
  51  ggtcttaatc tccgccggcg cactttcacc accataaccg ccgccatggg
 101  tgacgattcc ggcatggacg ctgtccagag acgtctcatg tttgatgatg
 151  aatgcatttt ggttgatgaa aatgacaatg ttcttgggca tgataccaaa
 201  tacaattgtc acttgatgga gaagattgag aaagataatt tgcttcatag
 251  agcattcagt gtatttttat tcaattcaaa atacgaatta ctccttcagc
 301  aaaggtcaga accaaggtg acatttcctt tggtatggac aaacacctgt
 351  tgcagccatc cactatacag agaatcggag ttaattcccg aaaatgccct
 401  tggggtcaga aatgctgcac agaggaagct tctagatgaa ctcggtatcc
 451  ctgctgaaga tgttccagtt gatgagttca caactttagg tcgcatgttg
 501  tacaaggctc catctgatgg aaaatggggt gaacatgaag ttgattacct
 551  actcttcctc gtgcgtgacg ttgccgtgaa cccaaaccct gatgaggtgg
 601  cggacattag atacgtgaac caagaagagt taaaagagtt actaaggaag
 651  gcggatgcgg gtgaggaggg tttgaaattg tccccatggt ttaggctagt
 701  ggtggacaac ttcttgttca aatggtggga tcatgtccaa aaggggacac
 751  tcaatgaagc aattgacatg aaaaccattc ataagttgat atgaaaaatg
 801  gttaatattt atggtggtgg tttggagcta ataatttgtg tgttcaagtc
 851  tcggtccttc ttttttaac gttttttttt tttcttttat tgggagtgtt
 901  tattgtgtac ttgtaacgta ggccctttgg ttacgcttta agagtttaat
 951  aaagaaccac cgttaattta aaaaaaaaa aaaaaaa
```

Fig.20

*Chlamydomonas reinhardtii Ipi1* (Note: the isomerase cDNA probably ends at *ca.* base 1103; the second half of the cDNA is similar to extensin and other hydroxyproline-rich structural proteins)

SEQ ID No.33

```
   1 ggcacgagct cgagtttgtt ttaccatgac atcgggaatt tggaagcttg
  51 aactacctca attactcaag taactcgcgg caacacattt cgcgcgccat
 101 cgctgttttc tctgctccag ctaccgagca gcattgcttt agatcgcttt
 151 gatgtcataa actcccactt atatgagatc cagtttcatc gagcccaagc
 201 ccagagcgca acctgtctta agccgcggca gggcgtccat gcgcctcgcg
 251 caaagccgtg ctctcgttgc gcgtgtcagc tccgccctgt ggcgggagc
 301 aggactttca caggctcaaa gcgttgcggt gcgaatggcg agttcgtcaa
 351 cctgggaagg cacgggcctg agccaggatg acttcatgca gcgggacgag
 401 tgcttggtgg tggacgagca ggaccggctg ctaggcaccg ccaacaagta
 451 cgactgccac cgcttcgagg cggccaaggg ccagccctgc ggccgcctgc
 501 accgcgcctt ctccgtgttc ctgttcagcc ccgacggccg actgctgctg
 551 cagcagcgcg cagccagcaa ggtgacgttc ccgggtgtgt ggaccaacac
 601 ctgctgctcg cacccgctgg cgggccaggc gccggacgag gtggacctgc
 651 cggcggcggt agcctcgggc caggtgccgg gcatcaaggc ggcggcggtg
 701 cgcaagctgc agcacgagct ggggataccg ccggagcagg ttcccgcctc
 751 ctccttctcc ttcctcacgc gtctgcacta ctgcgccgcc gacaccgcca
 801 cgcacggccc ggcggcggag tggggcgagc acgaggtgga ctacgtgctg
 851 ttcgtgcggc cgcagcagcc cgtcagcctg cagcccaacc cagacgaggt
 901 ggacgccacg cgctacgtga cgctgccgga gcttcagtcc atgatggcgg
 951 accccggcct cagctggagc cctggttcc gcatcctggc cacacagccc
1001 gccttcctgc ccgcctggtg gggcgacctg aagcggcgct ggcgcccggg
1051 cggcagccga ctgtcggact ggggcaccat ccaccgcgtc atgtgaagaa
1101 aaaggggaag caggggcggg agcggggggat gaatgggaat gtgaatgcga
1151 ttgtgatgcg gcgtgggatg aggtctgaag acagggggaa aatcgggggg
1201 cgggcgtgag cgtgtgtgta cgtgagcgac aaagccggga ggcggaccgc
1251 gcgatgggta catgtgtgtg cggagggtcg gtgggtcggt cggttgcgcg
1301 gcatagcgtg ttgtgtgtgt gcggctgcgc gggtatgtgg gcacccgggc
1351 acggaggaga aggcacacgc aggtggcgcg gaggtgtgtc aggggccatg
1401 ggcgggcctc actcctggtc gtgcccagtg gtctcgtggg cagagtggca
1451 ggggctgcac ccatatgagc ggcgcactgc cgcgctgggc taagtcctta
1501 tcacttggtg aggtggggcg aggtggctgt gggcggcggg cgcagtggca
1551 gaaggacacg gtgtgtgagc ggtggagctc tggccgtgcc ggccgtgagg
1601 ggcggatagc gatatgacgt tgtgcttggc cgctgtaatg cgggagaatg
1651 tgcaggccgc gagaagcggg cggtggcagg aggccgcagg ctgcagcacc
1701 cgttggggag gtgccgcctg caggcgcggc gccggcggg cctgagtaat
1751 gggcgcctga gtagtggcgg ccacaggagg cgcaggaggc agcagcagga
1801 ggacgagctg gagggacccg ttggcaaccc aaggttgcgc gtgtaacata
1851 gtggccatac aaaaaaaaaa aaaa
```

Fig.21A

*Tagetes erecta Ipi1*

SEQ ID No.34

```
  1  ccaaaaacaa ctcaaatctc ctccgtcgct cttactccgc catgggtgac
 51  gactccggca tggatgctgt tcagcgacgt ctcatgtttg acgatgaatg
101  cattttggtg gatgagtgtg acaatgtggt gggacatgat accaaataca
151  attgtcactt gatggagaag attgaaacag gtaaaatgct gcacagagca
201  ttcagcgttt ttctattcaa ttcaaaatac gagttacttc ttcagcaacg
251  gtctgcaacc aaggtgacat ttcctttagt atggaccaac acctgttgca
301  gccatccact ctacagagaa tccgagcttg ttcccgaaaa cgcccttgga
351  gtaagaaatg ctgcacagag gaagctgttg gatgaactcg gtatccctgc
401  tgaagatgtt cccgttgatc agtttactcc tttaggtcgc atgctctaca
451  aggctccatc tgatggaaag tggggagaac atgaacttga ctacctactt
501  ttcatagtga gagacgttgc tgtaaacccg aacccagatg aagtggcgga
551  tatcaaatat gtganccang aagagttaaa ggagctgcta aggaaagcag
601  atgcggggga ggagggtttg aagctgtctc catggttcag gttagtggtt
651  gataacttct tgttcaagtg gtgggatcat gtgcaaaagg gtacactcac
701  tgaagcaatt gatatgaaaa ccatacacaa gctgatatag aaacacaccc
751  tcaaccgaaa agttcaagcc taataattcg ggttgggtcg ggtctaccat
801  caattgtttt tttcttttaa gaagttttaa tctctatttg agcatgttga
851  ttcttgtctt ttgtgtgtaa gattttgggt ttcgtttcag ttgtaataat
901  gaaccattga tggtttgcaa tttcaagttc ctatcgacat gtagtgatct
951  aaaaaa
```

Fig.21B

*Oryza sativa Ipi1*

SEQ ID No.35
```
   1  cctccctttg cctcgcgcag aggcggccgc gccttctccg ccgcgaggat
  51  ggccggcgcc gccgccgccg tggaggacgc cgggatggac gaggtccaga
 101  agcggctcat gttcgacgac gaatgcattt tggtggatga acaagacaat
 151  gttgttggcc atgaatcaaa atataactgc catctgatgg aaaaaatcga
 201  atctgaaaat ctacttcata gggctttcag tgtattcctg ttcaactcaa
 251  aatatgaact cctactccag caacgatctg caacaaaggt tacatttcct
 301  ctagtttgga ccaacacttg ctgcagccat cctctgtacc gtgagtctga
 351  gcttatacag gaaaactacc ttggtgttag aaatgctgct cagaggaagc
 401  tcttggatga gctgggcatc ccagctgaag atgtgccagt tgaccaattc
 451  acccctcttg gtcggatgct ttacaaggcc ccatctgatg aaaatgggg
 501  tgaacacgag cttgactacc tgctgttcat cgtccgcgac gtgaaggtag
 551  tcccgaaccc ggacgaagtg gccgatgtga atacgtgag ccgtgagcag
 601  ctgaaggagc tcatccgcaa agcggacgcc ggagaggaag gcctgaagct
 651  gtctccctgg ttccggctgg ttgttgacaa cttcctcatg ggctggtggg
 701  atcacgtcga gaaaggcacc ctcaacgagg ccgtggacat ggagaccatc
 751  cacaagctga agtaaggact gcgatgttgt ggctggaaag aatgatcctg
 801  aagactctgt tcttgtgctg ctgcatatta ctcttaccag ggaagttgca
 851  gaagtcagaa gaagcttttg tatgtttctg ggtttggagc ttggaagtgt
 901  tgggctctgc tgactgagag attcccttat agagtgtcta tgttaattta
 951  gcaaacttct atattataca tgattagtta attgttcggt gtctgaataa
1001  agaacaatag catgttccat gtttatttgc t
```

Fig.22

ClustalW 1.7 Multiple Sequence Alignment of Plant and Green Algal Isopentenyl Pyrophosphate Isomerases (IPI)
These amino acid sequences were predicted by cDNAs that were isolated and identified by color complementation in E.coli

Fig.23A

Comparison using GAP program of the Genetics Computer Group
Gap Weight: 50        Average Match: 10.000
Length Weight: 3      Average Mismatch: 0.000
Quality: 17392        Length: 1904
Ratio: 9.411          Gaps: 3
Percent Similarity: 95.331   Percent Identity: 95.331
Match display thresholds for the alignment(s):  | = IDENTITY   : = 5   . = 1

*Adonis palaestina* -cyclase #3 (SEQ ID No.46) x *Adonis palaestina* -cyclase #5 (SEQ ID No.62)

```
  1 gagagaaaaagagtgttatattaatgttactgtcgcattcttgcaacac.  49   SEQ ID No.46
     |||  ||||||||  |||||||||||||||||||||||||||||||||
  1 ......aaaggagtgttctattaatgttactgtcgcattcttgcaacact  44   SEQ ID No.62

50 .atattcagactccatttttcttgttttctcttcaaaacaacaaactaatg  98
     |||||||  ||||||||||||| ||||||||||||||||||||||||||
 45 tatattcaaactccatttttcttcttttctcttcaaaacaacaaactaatg  94

99 tga.cggagtatctagctatggaactacttggtgttcgcaacctcatctc 147
     ||| |  |||||||| |||||||||||||||||||||||||||||||||
 95 tgagcagagtatctggctatggaactacttggtgttcgcaacctcatctc 144

148 ttcttgccctgtctggacttttggaacaagaaaccttagtagttcaaaac 197
    ||||||||||||| |||||||||||||||||||||||||||||||||||
145 ttcttgccctgtgtggacttttggaacaagaaaccttagtagttcaaaac 194

198 tagcttataacatacatcgatatggttcttcttgtagagtagattttcaa 247
    ||||||||||||||||||||||||||||||||||||||||||||||||
195 tagcttataacatacatcgatatggttcttcttgtagagtagattttcaa 244

248 gtgagggctgatggtggaagcgggagtagaacttctgttgcttataaaga 297
    |||||  ||||||||||||||||||||||||  ||||||||||||||||
245 gtgagagctgatggtggaagcgggagtagaagttctgttgcttataaaga 294

298 gggttttgtggacgaggaggatttttatcaaagctggtggttctgagcttt 347
    |||||||||| ||  |||||||||||||||||||||||||||||||||
295 gggttttgtggatgaagaggatttttatcaaagctggtggttctgagcttt 344

348 tgtttgtccaaatgcagcaaacaaagtctatggagaaacaggccaagctc 397
    ||||||||||||||||||||||||||||||||||||||||||||||||
345 tgtttgtccaaatgcagcaaacaaagtctatggagaaacaggccaagctc 394

398 gccgataagttgccaccaatacctttcggagaatctgtgatggacttggt 447
    |||||||||||||||||||||||||| |||||| ||| |||||||||||
395 gccgataagttgccaccaataccttttggagaatccgtgatggacttggt 444

448 tgtaataggttgtggacctgctggtctttcactggctgcagaagctgcta 497
    ||||||||||||||||||||||||||||||||||||||||||||||||
445 tgtaataggttgtggacctgctggtctttcactggctgcagaagctgcta 494

498 agctaggcttgaaagttggccttattggtcctgatcttccttttacaaat 547
    |||||||  |||||||||||||||||||||||||||| ||||||||||
495 agctagggttgaaagttggccttattggtcctgatcttcctttttacaaat 544

548 aattatggtgtgtgggaagacgagttcaaagatcttggacttgaacgttg 597
    |||||||||||||||||||||||||||||||||||||||||||||||||
545 aattatggtgtgtgggaagacgagttcaaagatcttggacttgaacgttg 594

598 tatcgagcatgcttggaaggacaccatcgtatatcttgacaatgatgctc 647
    |||||||||||||||||||||||||||||||||||||||  ||||||||
595 tatcgagcatgcttggaaggacaccatcgtatatcttgataatgatgctc 644

648 ctgtccttattggtcgtgcatatggacgagttagccggcatttgctgcat 697
    |||||||||||||||||||||||||||||||||| ||  |||||||  |
645 ctgtccttattggtcgtgcatatggacgagttagtcgacatttgctacat 694

698 gaagagttgctgaaaaggtgtgcgagtcaggtgtatcatatctgaattc 747
    || ||||||||||||||||||| ||||||||||||||||||||| ||
695 gaggagttgctgaaaaggtgtgtggagtcaggtgtatcatatctggattc 744

748 taaagtggaaaggatcactgaagctggtgatggccatagtcttgtagttt 797
    |||||||||||||||||||||||||||||||||||||| |||||||||
745 taaagtggaaaggatcactgaagctggtgatggccatagccttgtagttt 794

798 gtgaaaacgacatctttatcccttgcaggcttgctactgttgcatctgga 847
    ||||||  || |||||||||||||||||||||||||||||||||||||
795 gtgaaaatgagatctttatcccttgcaggcttgctactgttgcatctgga 844
```

Fig.23B

```
 848 gcagcttcagggaaacttttggagtatgaagtaggtggccctcgtgtttg  897
     ||||||||||||||||||||||||||||||||||||||||||||||||||
 845 gcagcttcagggaaacttttggagtatgaagtaggtggccctcgtgtttg  894

898 tgtccaaactgcttatggtgtggaggttgaggtggagaacaatccatacg  947
     ||||||||| |||||||||| ||||||||||||||||||||||||||||| 
 895 tgtccaaaccgcttatggggtggaggttgaggtggagaacaatccatacg  944

948 atcccaacttaatggtatttatggactacagagactatatgcaacagaaa  997
     |||||||||||||||||||| |||||||||||||||||||||||||||||
 945 atcccaacttaatggtattcatggactacagagactatatgcaacagaaa  994

998 ttacagtgctcggaagaagaatatccaacatttctctatgtcatgccat  1047
     ||||||||||||||||||||||||||||||||||||||||||||||||||
 995 ttacagtgctcggaagaagaatatccaacatttctctatgtcatgccat  1044

1048 gtcgccaacaagactttttttgaggaaacctgtttggcctcaaaagatg  1097
     ||||||||||||||||||||||||||||||||||||||||||||||||||
1045 gtcgccaacaagactttttttgaggaaacctgtttggcctcaaaagatg  1094

1098 ccatgcctttcgatctactgaagagaaaactaatgtcacgattgaagact  1147
     ||||||| |||||||||||||||||||||| |||||||||||||||||||
1095 ccatgccattcgatctactgaagagaaaactgatgtcacgattgaagact  1144

1148 ctgggtatccaagttacaaaaatttatgaagaggaatggtcttatattcc  1197
     |||||||||||||||||||| |||||||||||||||||||| ||||||||
1145 ctgggtatccaagttacaaaagtttatgaagaggaatggtcatatattcc  1194

1198 tgttgggggttctttaccaaacacagagcaaaagaacctagcatttggtg  1247
     ||||||| |||||||||||||||||||||||||||||||||||||||||| 
1195 tgttggtggttctttaccaaacacagagcaaaagaacctagcatttggtg  1244

1248 ctgcagcaagcatggtgcatccagcaacaggctattcggttgtacgatca  1297
     ||||||||||||||||||||||||||||||||||||||||||||||| ||
1245 ctgcagcaagcatggtgcatccagcaacaggctattcggttgtacggtca  1294

1298 ctatcagaagctccaaaatatgcttctgtaattgcaaagattttgaagca  1347
     || |||||||||||||||||||||||||| ||||||||||||||||||||
1295 ctgtcagaagctccaaaatatgcttctgtaattgcaaagattttgaagca  1344

1348 agataactctgcatatgtggtttctggacaaagcagtgcagtaaacattt  1397
     |||||||||||| |||||||||||||||||||| |||||||||||||||| 
1345 agataactctgcgtatgtggtttctggacaaagtagtgcagtaaacattt  1394

1398 caatgcaagcatggagcagtctttggccaaaggagcgaaaacgtcaaaga  1447
     ||||||||||||||||||||||||||||||||||||||||||||||||||
1395 caatgcaagcatggagcagtctttggccaaaggagcgaaaacgtcaaaga  1444

1448 gcattctttcttttcgggttagagcttattgtgcagctagatattgaagc  1497
     ||||||||||||| || |||||||||||||||||||||||||||||||||
1445 gcattctttcttttggattagagcttattgtgcagctagatattgaagc  1494

1498 aaccagaacgttctttagaaccttcttccgcttgccaacttggatgtggt  1547
     |||||||||| ||||||||||||||||||||||||||||||||||||||| 
1495 aaccagaacattctttagaaccttcttccgcttgccaacttggatgtggt  1544

1548 ggggtttccttgggtcttcactatcatctttcgatcttgtattgttttcc  1597
     |||||||||||||||||||||||||||||||||||| ||||||||||||| 
1545 ggggtttccttgggtcttcactatcatctttcgatctcgtcttgttttcc  1594

1598 atgtacatgtttgttttggccccgaacagcatgaggatgtcacttgtgag  1647
     ||||||||||||||||||||| ||||||||||||||||| ||||||||||
1595 atgtacatgtttgttttggcgccaaacagcatgaggatgtcacttgtgag  1644

1648 acatttgctttcagatccttctggtgcagttatggttaaagcttacctcg  1697
     ||||||||||||||||||||||||||||||||||||||| ||||||||||
1645 acatttgctttcagatccttctggtgcagttatggtaagagcttacctcg  1694

1698 aaagtaatc...tgttttatgaaactatagtgtctcattaaataaatga  1744
     ||||||| |   | ||| |||||||||| |||||||| ||||||||||||
1695 aaaggtagtctcatctattattaaactctagtgttttcaccaaataaatga  1744

1745 ggatccttcgtatatgtatatgatcatctctatgtatatcctatattcta  1794
     |||||||||| | ||||||||||||||||||||||||||| || || |||
1745 ggatccttcgaatgtgtatatgatcatctctatgtatatcctgtactcta  1794

1795 atctcataaagtaatcgaaaattcattgatagaaaaaaaaaaaaaaaaa  1844
     ||||||||||| |||| || || ||||| ||  ||| || 
1795 atctcataaagtaaatgccgggtttgatattgttgtgtcaaaccggcca  1844

1845 aaaa.............................................  1848

1845 tgatatataaagtaaatttattgatacaaaagtagttttttttccttaaaaaa  1894
```

Fig.24

```
GAP program of Genetics Computer Group
blosum62.cmp
       Gap Weight:      12       Average Match:     2.912
    Length Weight:       4    Average Mismatch:    -2.003
          Quality:    2728              Length:       530
            Ratio:   5.147                Gaps:         0
Percent Similarity: 99.623    Percent Identity:    99.057
 Match display thresholds for the alignment(s):  | = IDENTITY   : = 2   . = 1
```

*Adonis palaestina* ε-cyclase #3 (SEQ ID No.47) x *Adonis palaestina*
ε-cyclase #5 (SEQ ID No.23)

```
  1 MELLGVRNLISSCPVWTFGTRNLSSSKLAYNIHRYGSSCRVDFQVRADGG  50 ← SEQ ID No.47
    ||||||||||||||||||||||||||||||||||||||||||||||||||
  1 MELLGVRNLISSCPVWTFGTRNLSSSKLAYNIHRYGSSCRVDFQVRADGG  50 ← SEQ ID No.23

51 SGSRTSVAYKEGFVDEEDFIKAGGSELLFVQMQQTKSMEKQAKLADKLPP 100
    ||||.|||||||||||||||||||||||||||||||||||||||||||||
 51 SGSRSSVAYKEGFVDEEDFIKAGGSELLFVQMQQTKSMEKQAKLADKLPP 100

101 IPFGESVMDLVVIGCPGAGLSLAAEAAKLGLKVGLIGPDLPFTNNYGVWE 150
    ||||||||||||||||||||||||||||||||||||||||||||||||||
101 IPFGESVMDLVVIGCPGAGLSLAAEAAKLGLKVGLIGPDLPFTNNYGVWE 150

151 DEFKDLGLERCIEHAWKDTIVYLDNDAPVLIGRAYGRVSRHLLHEELLKR 200
    ||||||||||||||||||||||||||||||||||||||||||||||||||
151 DEFKDLGLERCIEHAWKDTIVYLDNDAPVLIGRAYGRVSRHLLHEELLKR 200

201 CVESGVSYLNSKVERITEAGDGHSLVVCENDIFIPCRLATVASGAASGKL 250
    |||||||||.||||||||||||||||||||:|||||||||||||||||||
201 CVESGVSYLDSKVERITEAGDGHSLVVCENEIFIPCRLATVASGAASGKL 250

251 LEYEVGGPRVCVQTAYGVEVEVENNPYDPNLMVFMDYRDYMQQKLQCSEE 300
    ||||||||||||||||||||||||||||||||||||||||||||||||||
251 LEYEVGGPRVCVQTAYGVEVEVENNPYDPNLMVFMDYRDYMQQKLQCSEE 300

301 EYPTFLYVMPMSPTRLFFEETCLASKDAMPFDLLKRKLMSRLKTLGIQVT 350
    ||||||||||||||||||||||||||||||||||||||||||||||||||
301 EYPTFLYVMPMSPTRLFFEETCLASKDAMPFDLLKRKLMSRLKTLGIQVT 350

351 KIYEEEWSYIPVGGSLPNTEQKNLAFGAAASMVHPATGYSVVRSLSEAPK 400
    |:||||||||||||||||||||||||||||||||||||||||||||||||
351 KVYEEEWSYIPVGGSLPNTEQKNLAFGAAASMVHPATGYSVVRSLSEAPK 400

401 YASVIAKILKQDNSAYVVSGQSSAVNISMQAWSSLWPKERKRQRAFFLFG 450
    ||||||||||||||||||||||||||||||||||||||||||||||||||
401 YASVIAKILKQDNSAYVVSGQSSAVNISMQAWSSLWPKERKRQRAFFLFG 450

451 LELIVQLDIEATRTFFRTFFRLPTWMWWGFLGSSLSSFDLVLFSMYMFVL 500
    ||||||||||||||||||||||||||||||||||||||||||||||||||
451 LELIVQLDIEATRTFFRTFFRLPTWMWWGFLGSSLSSFDLVLFSMYMFVL 500

501 APNSMRMSLVRHLLSDPSGAVMVKAYLER* 530
    |||||||||||||||||||||||:||||||
501 APNSMRMSLVRHLLSDPSGAVMVRAYLER* 530
```

```
GAP of: Arabidopsis epsilon cyclase to lettuce epsilon cyclase
    Gap Weight:       12      Average Match:     2.778
 Length Weight:        4      Average Mismatch: -2.248
       Quality:     1839              Length:     534
         Ratio:    3.503                Gaps:       3
Percent Similarity: 76.381    Percent Identity: 69.905
Atepscyc.pair (22%)
Percent Similarity: 76.381    Percent Identity: 69.905
       Match display thresholds for the alignment(s):
                   | = IDENTITY
                   : = 2
                   . = 1
```

Arabidopsis (SEQ ID No.49) x Lettuce (SEQ ID No.52)

```
  1 MECVGARNF.AAMAVSTFPSW...SCRRKFPVVKRYSYRNIRFGLCSVRA  46←SEQ ID No.49
    ||| ||||  | ||| | |.   . | || ..|.   : |:
  1 MECFGARNMTATMAVFTCPRFTDCNIRHKFSLLKQRRFTNLSASSSLRQI  50←SEQ ID No.52

47 SGGGSSGSESCVAVREDFADEEDFVKAGGSEILFVQMQQNKDMDEQSKLV  96
    |            |||||:|||||||: |||||.  | |: ||||
 51 KCSAKSDRCVVDKQGISVADEEDYVKAGGSELFFVQMQRTKSMESQSKLS 100

97 DKLPPISIGDGALDHVVIGCPAGLALAAESAKLGLKVGLIGPDLPFTNN 146
    :||  | ||.  || ||||||||||||||||||||| |||||||||||
101 EKLAQIPIGNCILDLVVIGCPAGLALAAESAKLGLNVGLIGPDLPFTNN 150

147 YGVWEDEFNDLGLQKCIEHVWRETIVYLDDDKPITIGRAYGRVSRRLLHE 196
    ||||:|||   |||: ||||  |::|:|||||  ||  |||||||| ||||| | |||
151 YGVWQDEFIGLGLEGCIEHSWKDTLVYLDDADPIRIGRAYGRVHRDLLHE 200

197 ELLRRCVESGVSYLSSKVDSITEASDGLRLVACDDNNVIPCRLATVASGA 246
    |||||||||||||||||||:  ||||  .|   |:  |:   |    |||||||||||
201 ELLRRCVESGVSYLSSKVERITEAPNGYSLIECEGNITIPCRLATVASGA 250

247 ASGKLLQYEVGGPRVCVQTAYGVEVEVENSPYDPDQMVFMDYRDYTNEKV 296
    ||||  |:||.|||||||||||||:||||||.||||| |||||||||:.  |
251 ASGKFLEYELGGPRVCVQTAYGIEVEVENNPYDPDLMVFMDYRDFSKHKP 300

297 RSLEAEYPTFLYAMPMTKSRLFFEETCLASKDVMPFDLLKTKLMLRLDTL 346
    ||||.||||||  | |.   .::||||||::  |||.|||.||| ||   :
301 ESLEAKYPTFLYVMAMSPTKIFFEETCLASREAMPFNLLKSKLMSRLKAM 350

347 GIRILKTYEEEWSYIPVGGSLPNTEQKNLAFGAAASMVHPATGYSVVRSL 396
    ||||  :|||||||||||||||||||||||||||||||||||||||||||||
351 GIRITRTYEEEWSYIPVGGSLPNTEQKNLAFGAAASMVHPATGYSVVRSL 400

397 SEAPKYASVIAEILREETTKQINS.....NISRQAWDTLWPPERKRQRAF 441
    ||||  ||.|||.|||::  .|:.  |    |||:|||:||||  ||||||||
401 SEAPNYAAVIAKILRQDQSKEMISLGKYTNISKQAWETLWPLERKRQRAF 450

442 FLFGLALIVQFDTEGIRSFFRTFFRLPKWMWQGFLGSTLTSGDLVLFALY  49
    |||||. ||   | ||  |.|||||||||||| |||||.|.|  ||::|||| 
451 FLFGLSHIVLMDLEGTRTFFRTFFRLPKWMWWGFLGSSLSSTDLIIFALY 500

492 MFVISPNNLRKGLINHLISDPTGATMIKTYLKV* 525
    ||||.|..||  |:  ||:||||||||:|| ||  :|
501 MFVIAPHSLRMELVRHLLSDPTGATMVKAYLTI* 534
```

```
                          SEQUENCE LISTING

<160> NUMBER OF SEQ ID NOS: 61

<210> SEQ ID NO 1
<211> LENGTH: 1860
<212> TYPE: DNA
<213> ORGANISM: Arabidopsis thaliana
<220> FEATURE:
<221> NAME/KEY: CDS
<222> LOCATION: (109)..(1680)

<400> SEQUENCE: 1 acaaaggaa ataattagat tcctctttct gcttgctata ccttgataga acaatataac      60
aatggtgtaa gtcttctcgc tgtattcgaa attatttgga ggaggaaa atg gag tgt    117
                                                    Met Glu Cys
                                                      1 gtt ggg gct agg aat ttc gca gca atg gcg gtt tca aca ttt ccg tca    165
Val Gly Ala Arg Asn Phe Ala Ala Met Ala Val Ser Thr Phe Pro Ser
      5                  10                  15 tgg agt tgt cga agg aaa ttt cca gtg gtt aag aga tac agc tat agg    213
Trp Ser Cys Arg Arg Lys Phe Pro Val Val Lys Arg Tyr Ser Tyr Arg
 20                  25                  30                  35 aat att cgt ttc ggt ttg tgt agt gtc aga gct agc ggc ggc gga agt    261
Asn Ile Arg Phe Gly Leu Cys Ser Val Arg Ala Ser Gly Gly Gly Ser
                 40                  45                  50 tcc ggt agt gag agt tgt gta gcg gtg aga gaa gat ttc gct gac gaa    309
Ser Gly Ser Glu Ser Cys Val Ala Val Arg Glu Asp Phe Ala Asp Glu
             55                  60                  65 gaa gat ttt gtg aaa gct ggt ggt tct gag att cta ttt gtt caa atg    357
Glu Asp Phe Val Lys Ala Gly Gly Ser Glu Ile Leu Phe Val Gln Met
         70                  75                  80 cag cag aac aaa gat atg gat gaa cag tct aag ctt gtt gat aag ttg    405
Gln Gln Asn Lys Asp Met Asp Glu Gln Ser Lys Leu Val Asp Lys Leu
     85                  90                  95
```

-continued

```
cct cct ata tca att ggt gat ggt gct ttg gat cat gtg gtt att ggt         453
Pro Pro Ile Ser Ile Gly Asp Gly Ala Leu Asp His Val Val Ile Gly
100             105                 110                 115 tgt ggt cct gct ggt tta gcc ttg gct gca gaa tca gct aag ctt gga         501
Cys Gly Pro Ala Gly Leu Ala Leu Ala Ala Glu Ser Ala Lys Leu Gly
                120                 125                 130 tta aaa gtt gga ctc att ggt cca gat ctt cct ttt act aac aat tac        549
Leu Lys Val Gly Leu Ile Gly Pro Asp Leu Pro Phe Thr Asn Asn Tyr
            135                 140                 145 ggt gtt tgg gaa gat gaa ttc aat gat ctt ggg ctg caa aaa tgt att       597
Gly Val Trp Glu Asp Glu Phe Asn Asp Leu Gly Leu Gln Lys Cys Ile
        150                 155                 160 gag cat gtt tgg aga gag act att gtg tat ctg gat gat gac aag cct       645
Glu His Val Trp Arg Glu Thr Ile Val Tyr Leu Asp Asp Asp Lys Pro
    165                 170                 175 att acc att ggc cgt gct tat gga aga gtt agt cga cgt ttg ctc cat       693
Ile Thr Ile Gly Arg Ala Tyr Gly Arg Val Ser Arg Arg Leu Leu His
180             185                 190                 195 gag gag ctt ttg agg agg tgt gtc gag tca ggt gtc tcg tac ctt agc       741
Glu Glu Leu Leu Arg Arg Cys Val Glu Ser Gly Val Ser Tyr Leu Ser
                200                 205                 210 tcg aaa gtt gac agc ata aca gaa gct tct gat ggc ctt aga ctt gtt       789
Ser Lys Val Asp Ser Ile Thr Glu Ala Ser Asp Gly Leu Arg Leu Val
            215                 220                 225 gct tgt gac gac aat aac gtc att ccc tgc agg ctt gcc act gtt gct       837
Ala Cys Asp Asp Asn Asn Val Ile Pro Cys Arg Leu Ala Thr Val Ala
        230                 235                 240 tct gga gca gct tcg gga aag ctc ttg caa tac gaa gtt ggt gga cct       885
Ser Gly Ala Ala Ser Gly Lys Leu Leu Gln Tyr Glu Val Gly Gly Pro
    245                 250                 255 aga gtc tgt gtg caa act gca tac ggc gtg gag gtt gag gtg gaa aat       933
Arg Val Cys Val Gln Thr Ala Tyr Gly Val Glu Val Glu Val Glu Asn
260             265                 270                 275 agt cca tat gat cca gat caa atg gtt ttc atg gat tac aga gat tat       981
Ser Pro Tyr Asp Pro Asp Gln Met Val Phe Met Asp Tyr Arg Asp Tyr
                280                 285                 290 act aac gag aaa gtt cgg agc tta gaa gct gag tat cca acg ttt ctg      1029
Thr Asn Glu Lys Val Arg Ser Leu Glu Ala Glu Tyr Pro Thr Phe Leu
            295                 300                 305 tac gcc atg cct atg aca aag tca aga ctc ttc ttc gag gag aca tgt      1077
Tyr Ala Met Pro Met Thr Lys Ser Arg Leu Phe Phe Glu Glu Thr Cys
        310                 315                 320 ttg gcc tca aaa gat gtc atg ccc ttt gat ttg cta aaa acg aag ctc      1125
Leu Ala Ser Lys Asp Val Met Pro Phe Asp Leu Leu Lys Thr Lys Leu
    325                 330                 335 atg tta aga tta gat aca ctc gga att cga att cta aag act tac gaa      1173
Met Leu Arg Leu Asp Thr Leu Gly Ile Arg Ile Leu Lys Thr Tyr Glu
340             345                 350                 355
```

-continued

```
gag gag tgg tcc tat atc cca gtt ggt ggt tcc ttg cca aac acc gaa    1221
Glu Glu Trp Ser Tyr Ile Pro Val Gly Gly Ser Leu Pro Asn Thr Glu
            360                 365                 370 caa aag aat ctc gcc ttt ggt gct gcc gct agc atg gta cat ccc gca    1269
Gln Lys Asn Leu Ala Phe Gly Ala Ala Ala Ser Met Val His Pro Ala
        375                 380                 385 aca ggc tat tca gtt gtg aga tct ttg tct gaa gct cca aaa tat gca    1317
Thr Gly Tyr Ser Val Val Arg Ser Leu Ser Glu Ala Pro Lys Tyr Ala
    390                 395                 400 tca gtc atc gca gag ata cta aga gaa gag act acc aaa cag atc aac    1365
Ser Val Ile Ala Glu Ile Leu Arg Glu Glu Thr Thr Lys Gln Ile Asn
405                 410                 415 agt aat att tca aga caa gct tgg gat act tta tgg cca cca gaa agg    1413
Ser Asn Ile Ser Arg Gln Ala Trp Asp Thr Leu Trp Pro Pro Glu Arg
420                 425                 430                 435 aaa aga cag aga gca ttc ttt ctc ttt ggt ctt gca ctc ata gtt caa    1461
Lys Arg Gln Arg Ala Phe Phe Leu Phe Gly Leu Ala Leu Ile Val Gln
            440                 445                 450 ttc gat acc gaa ggc att aga agc ttc ttc cgt act ttc ttc cgc ctt    1509
Phe Asp Thr Glu Gly Ile Arg Ser Phe Phe Arg Thr Phe Phe Arg Leu
        455                 460                 465 cca aaa tgg atg tgg caa ggg ttt cta gga tca aca tta aca tca gga    1557
Pro Lys Trp Met Trp Gln Gly Phe Leu Gly Ser Thr Leu Thr Ser Gly
    470                 475                 480 gat ctc gtt ctc ttt gct tta tac atg ttc gtc att tca cca aac aat    1605
Asp Leu Val Leu Phe Ala Leu Tyr Met Phe Val Ile Ser Pro Asn Asn
            485                 490                 495 ttg aga aaa ggt ctc atc aat cat ctc atc tct gat cca acc gga gca    1653
Leu Arg Lys Gly Leu Ile Asn His Leu Ile Ser Asp Pro Thr Gly Ala
500                 505                 510                 515 acc atg ata aaa acc tat ctc aaa gta tgatttactt atcaactctt          1700
Thr Met Ile Lys Thr Tyr Leu Lys Val
                520 aggtttgtgt atatatatgt tgatttatct gaataatcga tcaaagaatg gtatgtgggt  1760 tactaggaag ttggaaacaa acatgtatag aatctaagga gtgatcgaaa tggagatgga  1820 aacgaaaaga aaaaaatcag tctttgtttt gtggttagtg                        1860

<210> SEQ ID NO 2
<211> LENGTH: 524
<212> TYPE: PRT
<213> ORGANISM: Arabidopsis thaliana

<400> SEQUENCE: 2

Met Glu Cys Val Gly Ala Arg Asn Phe Ala Ala Met Ala Val Ser Thr
1               5                   10                  15

Phe Pro Ser Trp Ser Cys Arg Arg Lys Phe Pro Val Val Lys Arg Tyr
            20                  25                  30

Ser Tyr Arg Asn Ile Arg Phe Gly Leu Cys Ser Val Arg Ala Ser Gly
        35                  40                  45
```

-continued

```
Gly Gly Ser Ser Gly Ser Glu Ser Cys Val Ala Val Arg Glu Asp Phe
         50                  55                  60

Ala Asp Glu Glu Asp Phe Val Lys Ala Gly Gly Ser Glu Ile Leu Phe
 65                  70                  75                  80

Val Gln Met Gln Gln Asn Lys Asp Met Asp Glu Gln Ser Lys Leu Val
                 85                  90                  95

Asp Lys Leu Pro Pro Ile Ser Ile Gly Asp Gly Ala Leu Asp His Val
                100                 105                 110

Val Ile Gly Cys Gly Pro Ala Gly Leu Ala Leu Ala Ala Glu Ser Ala
            115                 120                 125

Lys Leu Gly Leu Lys Val Gly Leu Ile Gly Pro Asp Leu Pro Phe Thr
130                 135                 140

Asn Asn Tyr Gly Val Trp Glu Asp Glu Phe Asn Asp Leu Gly Leu Gln
145                 150                 155                 160

Lys Cys Ile Glu His Val Trp Arg Glu Thr Ile Val Tyr Leu Asp Asp
                165                 170                 175

Asp Lys Pro Ile Thr Ile Gly Arg Ala Tyr Gly Arg Val Ser Arg Arg
                180                 185                 190

Leu Leu His Glu Glu Leu Leu Arg Arg Cys Val Glu Ser Gly Val Ser
            195                 200                 205

Tyr Leu Ser Ser Lys Val Asp Ser Ile Thr Glu Ala Ser Asp Gly Leu
210                 215                 220

Arg Leu Val Ala Cys Asp Asp Asn Val Ile Pro Cys Arg Leu Ala
225                 230                 235                 240

Thr Val Ala Ser Gly Ala Ala Ser Gly Lys Leu Leu Gln Tyr Glu Val
                245                 250                 255

Gly Gly Pro Arg Val Cys Val Gln Thr Ala Tyr Gly Val Glu Val Glu
                260                 265                 270

Val Glu Asn Ser Pro Tyr Asp Pro Asp Gln Met Val Phe Met Asp Tyr
            275                 280                 285

Arg Asp Tyr Thr Asn Glu Lys Val Arg Ser Leu Glu Ala Glu Tyr Pro
290                 295                 300

Thr Phe Leu Tyr Ala Met Pro Met Thr Lys Ser Arg Leu Phe Phe Glu
305                 310                 315                 320

Glu Thr Cys Leu Ala Ser Lys Asp Val Met Pro Phe Asp Leu Leu Lys
                325                 330                 335

Thr Lys Leu Met Leu Arg Leu Asp Thr Leu Gly Ile Arg Ile Leu Lys
                340                 345                 350

Thr Tyr Glu Glu Glu Trp Ser Tyr Ile Pro Val Gly Gly Ser Leu Pro
            355                 360                 365

Asn Thr Glu Gln Lys Asn Leu Ala Phe Gly Ala Ala Ala Ser Met Val
370                 375                 380

His Pro Ala Thr Gly Tyr Ser Val Arg Ser Leu Ser Glu Ala Pro
385                 390                 395                 400

Lys Tyr Ala Ser Val Ile Ala Glu Ile Leu Arg Glu Glu Thr Thr Lys
                405                 410                 415

Gln Ile Asn Ser Asn Ile Ser Arg Gln Ala Trp Asp Thr Leu Trp Pro
                420                 425                 430

Pro Glu Arg Lys Arg Gln Arg Ala Phe Phe Leu Phe Gly Leu Ala Leu
            435                 440                 445

Ile Val Gln Phe Asp Thr Glu Gly Ile Arg Ser Phe Phe Arg Thr Phe
450                 455                 460

Phe Arg Leu Pro Lys Trp Met Trp Gln Gly Phe Leu Gly Ser Thr Leu
```

```
465                 470                 475                 480
Thr Ser Gly Asp Leu Val Leu Phe Ala Leu Tyr Met Phe Val Ile Ser
            485                 490                 495
Pro Asn Asn Leu Arg Lys Gly Leu Ile Asn His Leu Ile Ser Asp Pro
        500                 505                 510
Thr Gly Ala Thr Met Ile Lys Thr Tyr Leu Lys Val
        515                 520

<210> SEQ ID NO 3
<211> LENGTH: 956
<212> TYPE: DNA
<213> ORGANISM: Arabidopsis thaliana

<400> SEQUENCE: 3
gctctttctc ctcctcctct accgatttcc gactccgcct cccgaaatcc ttatccggat     60
tctctccgtc tcttcgattt aaacgctttt ctgtctgtta cgtcgtcgaa gaacggagac    120
agaattctcc gattgagaac gatgagagac cggagagcac gagctccaca acgctatag    180 acgctgagta tctggcgttg cgtttggcgg agaaattgga gaggaagaaa tcggagaggt    240
ccacttatct aatcgctgct atgttgtcga gctttggtat cacttctatg ctgttatgg    300 ctgtttacta cagattctct tggcaaatgg agggaggtga gatctcaatg ttggaaatgt    360
ttggtacatt tgctctctct gttggtgctg ctgttggtat ggaattctgg caagatggg    420 ctcatagagc tctgtggcac gcttctctat ggaatatgca tgagtcacat acaaaaccaa    480
gagaaggacc gtttgagcta acgatgtttt tgctatagt gaacgctggt ccagcgattg    540
gtctcctctc ttatggattc ttcaataaag gactcgttcc tggtctctgc tttggcgccg    600
ggttaggcat aacggtgttt ggaatcgcct acatgtttgt ccacgatggt ctcgtgcaca    660
agcgtttccc tgtaggtccc atcgccgacg tcccttacct ccgaaaggtc gccgccgctc    720
accagctaca tcacacagac aagttcaatg gtgtaccata tggactgttt cttggaccca    780
aggaattgga agaagttgga ggaaatgaag agttagataa ggagattagt cggagaatca    840
aatcatacaa aaaggcctcg ggctccgggt cgagttcgag ttcttgactt taaacaagtt    900
ttaaatccca aattcttttt ttgtcttctg tcattatgat catcttaaga cggtct        956

<210> SEQ ID NO 4
<211> LENGTH: 294
<212> TYPE: PRT
<213> ORGANISM: Arabidopsis thaliana

<400> SEQUENCE: 4

Ser Phe Ser Ser Ser Thr Asp Phe Arg Leu Arg Leu Pro Lys Ser
  1               5                  10                  15

Leu Ser Gly Phe Ser Pro Ser Leu Arg Phe Lys Arg Phe Ser Val Cys
            20                  25                  30

Tyr Val Val Glu Glu Arg Arg Gln Asn Ser Pro Ile Glu Asn Asp Glu
        35                  40                  45

Arg Pro Glu Ser Thr Ser Ser Thr Asn Ala Ile Asp Ala Glu Tyr Leu
    50                  55                  60

Ala Leu Arg Leu Ala Glu Lys Leu Glu Arg Lys Lys Ser Glu Arg Ser
65                  70                  75                  80

Thr Tyr Leu Ile Ala Ala Met Leu Ser Ser Phe Gly Ile Thr Ser Met
                85                  90                  95

Ala Val Met Ala Val Tyr Tyr Arg Phe Ser Trp Gln Met Glu Gly Gly
            100                 105                 110
```

```
Glu Ile Ser Met Leu Glu Met Phe Gly Thr Phe Ala Leu Ser Val Gly
            115                 120                 125

Ala Ala Val Gly Met Glu Phe Trp Ala Arg Trp Ala His Arg Ala Leu
        130                 135                 140

Trp His Ala Ser Leu Trp Met Asn His Glu Ser His His Lys Pro Arg
145                 150                 155                 160

Glu Gly Pro Phe Glu Leu Asn Asp Val Phe Ala Ile Val Asn Ala Gly
                165                 170                 175

Pro Ala Ile Gly Leu Leu Ser Tyr Gly Phe Phe Asn Lys Gly Leu Val
            180                 185                 190

Pro Gly Leu Cys Phe Gly Ala Gly Leu Gly Ile Thr Val Phe Gly Ile
        195                 200                 205

Ala Tyr Met Phe Val His Asp Gly Leu Val His Lys Arg Phe Pro Val
    210                 215                 220

Gly Pro Ile Ala Asp Val Pro Tyr Leu Arg Lys Val Ala Ala Ala His
225                 230                 235                 240

Gln Leu His His Thr Asp Lys Phe Asn Gly Val Pro Tyr Gly Leu Phe
                245                 250                 255

Leu Gly Pro Lys Glu Leu Glu Glu Val Gly Gly Asn Glu Glu Leu Asp
            260                 265                 270

Lys Glu Ile Ser Arg Arg Ile Lys Ser Tyr Lys Lys Ala Ser Gly Ser
        275                 280                 285

Gly Ser Ser Ser Ser Ser
            290

<210> SEQ ID NO 5
<211> LENGTH: 162
<212> TYPE: PRT
<213> ORGANISM: Alicalgenes sp.

<400> SEQUENCE: 5

Met Thr Gln Phe Leu Ile Val Val Ala Thr Val Leu Val Met Glu Leu
1               5                   10                  15

Thr Ala Tyr Ser Val His Arg Trp Ile Met His Gly Pro Leu Gly Trp
            20                  25                  30

Gly Trp His Lys Ser His His Glu Glu His Asp His Ala Leu Glu Lys
        35                  40                  45

Asn Asp Leu Tyr Gly Val Val Phe Ala Val Leu Ala Thr Ile Leu Phe
    50                  55                  60

Thr Val Gly Ala Tyr Trp Trp Pro Val Leu Trp Trp Ile Ala Leu Gly
65                  70                  75                  80

Met Thr Val Tyr Gly Leu Ile Tyr Phe Ile Leu His Asp Gly Leu Val
                85                  90                  95

His Gln Arg Trp Pro Phe Arg Tyr Ile Pro Arg Arg Gly Tyr Phe Arg
            100                 105                 110

Arg Leu Tyr Gln Ala His Arg Leu His His Ala Val Glu Gly Arg Asp
        115                 120                 125

His Cys Val Ser Phe Gly Phe Ile Tyr Ala Pro Pro Val Asp Lys Leu
    130                 135                 140

Lys Gln Asp Leu Lys Arg Ser Gly Val Leu Arg Pro Gln Asp Glu Arg
145                 150                 155                 160

Pro Ser

<210> SEQ ID NO 6
```

```
<211> LENGTH: 175
<212> TYPE: PRT
<213> ORGANISM: Erwinia herbicola

<400> SEQUENCE: 6

Met Leu Asn Ser Leu Ile Val Ile Leu Ser Val Ile Ala Met Glu Gly
 1               5                  10                  15

Ile Ala Ala Phe Thr His Arg Tyr Ile Met His Gly Trp Gly Trp Arg
                20                  25                  30

Trp His Glu Ser His His Thr Pro Arg Lys Gly Val Phe Glu Leu Asn
            35                  40                  45

Asp Leu Phe Ala Val Val Phe Ala Gly Val Ala Ile Ala Leu Ile Ala
        50                  55                  60

Val Gly Thr Ala Gly Val Trp Pro Leu Gln Trp Ile Gly Cys Gly Met
65                  70                  75                  80

Thr Val Tyr Gly Leu Leu Tyr Phe Leu Val His Asp Gly Leu Val His
                85                  90                  95

Gln Arg Trp Pro Phe His Trp Ile Pro Arg Arg Gly Tyr Leu Lys Arg
               100                 105                 110

Leu Tyr Val Ala His Arg Leu His His Ala Val Arg Gly Arg Glu Gly
           115                 120                 125

Cys Val Ser Phe Gly Phe Ile Tyr Ala Arg Lys Pro Ala Asp Leu Gln
130                 135                 140

Ala Ile Leu Arg Glu Arg His Gly Arg Pro Lys Arg Asp Ala Ala
145                 150                 155                 160

Lys Asp Arg Pro Asp Ala Ala Ser Pro Ser Ser Ser Pro Glu
                165                 170                 175

<210> SEQ ID NO 7
<211> LENGTH: 175
<212> TYPE: PRT
<213> ORGANISM: Erwinia uredovora

<400> SEQUENCE: 7

Met Leu Trp Ile Trp Asn Ala Leu Ile Val Phe Val Thr Val Ile Gly
 1               5                  10                  15

Met Glu Val Ile Ala Ala Leu Ala His Lys Tyr Ile Met His Gly Trp
                20                  25                  30

Gly Trp Gly Trp His Leu Ser His His Glu Pro Arg Lys Gly Ala Phe
            35                  40                  45

Glu Val Asn Asp Leu Tyr Ala Val Val Phe Ala Ala Leu Ser Ile Leu
        50                  55                  60

Leu Ile Tyr Leu Gly Ser Thr Gly Met Trp Pro Leu Gln Trp Ile Gly
65                  70                  75                  80

Ala Gly Met Thr Ala Tyr Gly Leu Leu Tyr Phe Met Val His Asp Gly
                85                  90                  95

Leu Val His Gln Arg Trp Pro Phe Arg Tyr Ile Pro Arg Lys Gly Tyr
               100                 105                 110

Leu Lys Arg Leu Tyr Met Ala His Arg Met His His Ala Val Arg Gly
           115                 120                 125

Lys Glu Gly Cys Val Ser Phe Gly Phe Leu Tyr Ala Pro Pro Leu Ser
130                 135                 140

Lys Leu Gln Ala Thr Leu Arg Glu Arg His Gly Ala Arg Ala Gly Ala
145                 150                 155                 160

Ala Arg Asp Ala Gln Gly Gly Glu Asp Glu Pro Ala Ser Gly Lys
                165                 170                 175
```

<210> SEQ ID NO 8
<211> LENGTH: 162
<212> TYPE: PRT
<213> ORGANISM: Agrobacterium aurianticum

<400> SEQUENCE: 8

```
Met Thr Asn Phe Leu Ile Val Val Ala Thr Val Leu Val Met Glu Leu
  1               5                  10                  15

Thr Ala Tyr Ser Val His Arg Trp Ile Met His Gly Pro Leu Gly Trp
             20                  25                  30

Gly Trp His Lys Ser His His Glu Glu His Asp His Ala Leu Glu Lys
         35                  40                  45

Asn Asp Leu Tyr Gly Leu Val Phe Ala Val Ile Ala Thr Val Leu Phe
     50                  55                  60

Thr Val Gly Trp Ile Trp Ala Pro Val Leu Trp Trp Ile Ala Leu Gly
 65                  70                  75                  80

Met Thr Val Tyr Gly Leu Ile Tyr Phe Val Leu His Asp Gly Leu Val
                 85                  90                  95

His Trp Arg Trp Pro Phe Arg Tyr Ile Pro Arg Lys Gly Tyr Ala Arg
            100                 105                 110

Arg Leu Tyr Gln Ala His Arg Leu His His Ala Val Glu Gly Arg Asp
        115                 120                 125

His Cys Val Ser Phe Gly Phe Ile Tyr Ala Pro Pro Val Asp Lys Leu
    130                 135                 140

Lys Gln Asp Leu Lys Met Ser Gly Val Leu Arg Ala Glu Ala Gln Glu
145                 150                 155                 160

Arg Thr
```

<210> SEQ ID NO 9
<211> LENGTH: 954
<212> TYPE: DNA
<213> ORGANISM: Arabidopsis thaliana

<400> SEQUENCE: 9

```
ccacgggtcc gcctccccgt ttttttccga tccgatctcc ggtgccgagg actcagctgt    60
ttgttcgcgc tttctcagcc gtcaccatga ccgattctaa cgatgctgga atggatgctg   120
ttcagagacg actcatgttt gaagacgaat gcattctcgt tgatgaaaat aatcgtgtgg   180
tgggacatga cactaagtat aactgtcatc tgatggaaaa gattgaagct gagaaattac   240
ttcacagagc tttcagtgtg tttttattca actccaagta tgagttgctt ctccagcaac   300
ggtcaaaaac aaaggttact ttcccacttg tgtggacaaa cacttgttgc agccatcctc   360
tttaccgtga atccgagctt attgaagaga atgtgcttgg tgtaagaaat gccgcacaaa   420
ggaagctttt cgatgagctc ggtattgtag cagaagatgt accagtcgat gagttcactc   480
ccttgggacg catgctttac aaggcaccct ctgatgggaa atggggagag cacgaagttg   540
actatctact cttcatcgtg cgggatgtga agcttcaacc aaacccagat gaagtggctg   600
agatcaagta cgtgagcagg gaagagctta aggagctggt gaagaaagca gatgctggcg   660
atgaagctgt gaaactatct ccatggttca gattggtggt ggataatttc ttgatgaagt   720
ggtgggatca tgttgagaaa ggaactatca ctgaagctgc agacatgaaa accattcaca   780
agctctgaac tttccataag ttttggatct tccccttccc ataataaaat taagagatga   840
gactttatt gattacagac aaaactggca acaaaatcta ttcctaggat ttttttttgc   900
```

```
ttttttattta cttttgattc atctctagtt tagttttcat cttaaaaaaa aaaa              954
```

<210> SEQ ID NO 10
<211> LENGTH: 996
<212> TYPE: DNA
<213> ORGANISM: Arabidopsis thaliana

<400> SEQUENCE: 10

```
caccaatgtc tgtttcttct ttatttaatc tcccattgat tcgcctcaga tctctcgctc        60
tttcgtcttc ttttcttct ttccgatttg cccatcgtcc tctgtcatcg atttcaccga       120
gaaagttacc gaattttcgt gctttctctg gtaccgctat gacagatact aaagatgctg      180
gtatggatgc tgttcagaga cgtctcatgt ttgaggatga atgcattctt gttgatgaaa      240
ctgatcgtgt tgtggggcat gtcagcaagt ataattgtca tctgatggaa aatattgaag      300
ccaagaattt gctgcacagg gcttttagtg tatttttatt caactcgaag tatgagttgc      360
ttctccagca aaggtcaaac acaaaggtta cgttccctct agtgtggact aacacttgtt      420
gcagccatcc tctttaccgt gaatcagagc ttatccagga caatgcacta ggtgtgagga      480
atgctgcaca aagaaagctt ctcgatgagc ttggtattgt agctgaagat gtaccagtcg      540
atgagttcac tcccttggga cgtatgctgt acaaggctcc ttctgatggc aaatggggag      600
agcatgaact tgattacttg ctcttcatcg tgcgagacgt gaaggttcaa ccaaacccag      660
atgaagtagc tgagatcaag tatgtgagcc gggaagagct gaaggagctg gtgaagaaag      720
cagatgcagg tgaggaaggt ttgaaactgt caccatggtt cagattggtg gtggacaatt      780
tcttgatgaa gtggtgggat catgttgaga aggaactttt ggttgaagct atagacatga      840
aaaccatcca caaactctga acatcttttt ttaaagtttt taaatcaatc aactttctct      900
tcatcatttt tatcttttcg atgataataa tttgggatat gtgagacact tacaaaactt      960
ccaagcacct caggcaataa taaagtttgc ggccgc                                 996
```

<210> SEQ ID NO 11
<211> LENGTH: 1165
<212> TYPE: DNA
<213> ORGANISM: Haematococcus pluvialis

<400> SEQUENCE: 11

```
ctcggtagct ggccacaatc gctatttgga acctggcccg gcggcagtcc gatgccgcga        60
tgcttcgttc gttgctcaga ggcctcacgc atatccccg cgtgaactcc gcccagcagc       120
ccagctgtgc acacgcgcga ctccagttta agctcaggag catgcagatg acgctcatgc      180
agcccagcat ctcagccaat ctgtcgcgcg ccgaggaccg cacagaccac atgagggtg      240
caagcacctg ggcaggcggg cagtcgcagg atgagctgat gctgaaggac gagtgcatct      300
tggtggatgt tgaggacaac atcacaggcc atgccagcaa gctggagtgt cacaagttcc      360
taccacatca gcctgcaggc tgctgcacc gggccttctc tgtgttcctg tttgacgatc       420
agggcgact gctgctgcaa cagcgtgcac gctcaaaaat caccttccca agtgtgtgga      480
cgaacacctg ctgcagccac cctttacatg gcagacccc agatgaggtg gaccaactaa      540
gccaggtggc cgacggaaca gtacctggcg caaaggctgc tgccatccgc aagttggagc      600
acgagctggg gataccagcg caccagctgc cggcaagcgc gtttcgcttc ctcacgcgtt      660
tgcactactg tgccgcggac gtgcagccag ctgcgacaca atcagcgctc tggggcgagc      720
acgaaatgga ctacatcttg ttcatccggg ccaacgtcac cttggcgccc aaccctgacg      780
aggtggacga agtcaggtac gtgacgcaag aggagctgcg gcagatgatg cagccggaca      840
```

```
acgggctgca atggtcgccg tggtttcgca tcatcgccgc gcgcttcctt gagcgttggt    900
gggctgacct ggacgcggcc ctaaacactg acaaacacga ggattgggga acggtgcatc    960
acatcaacga agcgtgaaag cagaagctgc aggatgtgaa gacacgtcat ggggtggaat   1020
tgcgtacttg gcagcttcgt atctcctttt tctgagactg aacctgcagt caggtcccac   1080
aaggtcaggt aaaatggctc gataaaatgt accgtcactt tttgtcgcgt atactgaact   1140
ccaagaggtc aaaaaaaaaa aaaaa                                         1165
```

<210> SEQ ID NO 12
<211> LENGTH: 1135
<212> TYPE: DNA
<213> ORGANISM: Haematococcus pluvialis

<400> SEQUENCE: 12

```
ctcggtagct ggccacaatc gctatttgga acctggcccg gcggcagtcc gatgccgcga     60
tgcttcgttc gttgctcaga ggcctcacgc atatcccgcg cgtgaactcc gcccagcagc    120
ccagctgtgc acacgcgcga ctccagttta agctcaggag catgcagctg ctttccgagg    180
accgcacaga ccacatgagg ggtgcaagca cctgggcagg cgggcagtcg caggatgagc    240
tgatgctgaa ggacgagtgc atcttggtag atgttgagga caacatcaca ggccatgcca    300
gcaagctgga gtgtcacaag ttcctaccac atcagcctgc aggcctgctg caccgggcct    360
tctctgtgtt cctgtttgac gatcagggc gactgctgct gcaacagcgt gcacgctcaa    420
aaatcacctt cccaagtgtg tggacgaaca cctgctgcag ccacccttta catgggcaga    480
ccccagatga ggtggaccaa ctaagccagg tggccgacgg aacagtacct ggcgcaaagg    540
ctgctgccat ccgcaagttg gagcacgagc tggggatacc agcgcaccag ctgccggcaa    600
gcgcgtttcg cttcctcacg cgtttgcact actgtgccgc ggacgtgcag ccagctgcga    660
cacaatcagc gctctggggc gagcacgaaa tggactacat cttgttcatc cgggccaacg    720
tcaccttggc gcccaaccct gacgaggtgg acgaagtcag gtacgtgacg caagaggagc    780
tgcggcagat gatgcagccg acaacgggc ttcaatggtc gccgtggttt cgcatcatcg    840
ccgcgcgctt ccttgagcgt tggtgggctg acctggacgc ggcctaaaac actgacaaac    900
acgaggattg gggaacggtg catcacatca acgaagcgtg aaggcagaag ctgcaggatg    960
tgaagacacg tcatggggtg gaattgcgta cttggcagct tcgtatctcc tttttctgag   1020
actgaacctg cagagctaga gtcaatggtg catcatattc atcgtctctc ttttgtttta   1080
gactaatctg tagctagagt cactgatgaa tcctttacaa ctttcaaaaa aaaaa         1135
```

<210> SEQ ID NO 13
<211> LENGTH: 960
<212> TYPE: DNA
<213> ORGANISM: Tagetes erecta
<220> FEATURE:
<221> NAME/KEY: modified_base
<222> LOCATION: (366)..(680)
<223> OTHER INFORMATION: a, t, c, g, other or unknown

<400> SEQUENCE: 13

```
ccaaaaacaa ctcaaatctc ctccgtcgct cttactccgc catgggtgac gactccggca     60
tggatgctgt tcagcgacgt ctcatgtttg acgatgaatg catttggtg gatgagtgtg    120 acaatgtggt gggacatgat accaaataca attgtcactt gatggagaag attgaaacag    180
gtaaaatgct gcacagagca ttcagcgttt ttctattcaa ttcaaaatac gagttacttc    240
```

-continued

```
ttcagcaacg gtctgcaacc aaggtgacat ttcctttagt atggaccaac acctgttgca    300
gccatccact ctacagagaa tccgagcttg ttcccgaaac gcctgagaga atgctgcaca    360
gaggannnnn nnnnnnnnnn nnnnnnnnnn nnnnnnnnnn nnnnnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn nnnnnnnnnn nnnnnnnnnn nnnnnnnnnn    660
nnnnnnnnnn nnnnnnnnnn tcatgtgcaa aagggtacac tcactgaatg caatttgata    720
tgaaaaccat acacaagctg atatagaaac acaccctcaa ccgaaaagca agcctaataa    780
ttcggggttgg gtcgggtcta ccatcaattg ttttttttctt ttaacaactt ttaatctcta   840
tttgagcatg ttgattcttg tcttttgtgt gtaagatttt gggtttcgtt tcagttgtaa    900
taatgaacca ttgatggttt gcaatttcaa gttcctatcg acatgtagtg atctaaaaaa    960
```

<210> SEQ ID NO 14
<211> LENGTH: 305
<212> TYPE: PRT
<213> ORGANISM: Haematococcus pluvialis

<400> SEQUENCE: 14

```
Met Leu Arg Ser Leu Leu Arg Gly Leu Thr His Ile Pro Arg Val Asn
  1               5                  10                  15

Ser Ala Gln Gln Pro Ser Cys Ala His Ala Arg Leu Gln Phe Lys Leu
             20                  25                  30

Arg Ser Met Gln Met Thr Leu Met Gln Pro Ser Ile Ser Ala Asn Leu
         35                  40                  45

Ser Arg Ala Glu Asp Arg Thr Asp His Met Arg Gly Ala Ser Thr Trp
     50                  55                  60

Ala Gly Gly Gln Ser Gln Asp Glu Leu Met Leu Lys Asp Glu Cys Ile
 65                  70                  75                  80

Leu Val Asp Val Glu Asp Asn Ile Thr Gly His Ala Ser Lys Leu Glu
                 85                  90                  95

Cys His Lys Phe Leu Pro His Gln Pro Ala Gly Leu Leu His Arg Ala
            100                 105                 110

Phe Ser Val Phe Leu Phe Asp Asp Gln Gly Arg Leu Leu Leu Gln Gln
        115                 120                 125

Arg Ala Arg Ser Lys Ile Thr Phe Pro Ser Val Trp Thr Asn Thr Cys
    130                 135                 140

Cys Ser His Pro Leu His Gly Gln Thr Pro Asp Glu Val Asp Gln Leu
145                 150                 155                 160

Ser Gln Val Ala Asp Gly Thr Val Pro Gly Ala Lys Ala Ala Ile
                165                 170                 175

Arg Lys Leu Glu His Glu Leu Gly Ile Pro Ala His Gln Leu Pro Ala
            180                 185                 190

Ser Ala Phe Arg Phe Leu Thr Arg Leu His Tyr Cys Ala Ala Asp Val
        195                 200                 205

Gln Pro Ala Ala Thr Gln Ser Ala Leu Trp Gly Glu His Glu Met Asp
    210                 215                 220

Tyr Ile Leu Phe Ile Arg Ala Asn Val Thr Leu Ala Pro Asn Pro Asp
225                 230                 235                 240

Glu Val Asp Glu Val Arg Tyr Val Thr Gln Glu Glu Leu Arg Gln Met
                245                 250                 255
```

```
Met Gln Pro Asp Asn Gly Leu Gln Trp Ser Pro Trp Phe Arg Ile Ile
            260                 265                 270

Ala Ala Arg Phe Leu Glu Arg Trp Trp Ala Asp Leu Asp Ala Ala Leu
            275                 280                 285

Asn Thr Asp Lys His Glu Asp Trp Gly Thr Val His His Ile Asn Glu
            290                 295                 300

Ala
305

<210> SEQ ID NO 15
<211> LENGTH: 293
<212> TYPE: PRT
<213> ORGANISM: Haematococcus pluvialis

<400> SEQUENCE: 15

Met Leu Arg Ser Leu Leu Arg Gly Leu Thr His Ile Pro Arg Val Asn
  1               5                  10                  15

Ser Ala Gln Gln Pro Ser Cys Ala His Ala Arg Leu Gln Phe Lys Leu
             20                  25                  30

Arg Ser Met Gln Leu Leu Ser Glu Asp Arg Thr Asp His Met Arg Gly
         35                  40                  45

Ala Ser Thr Trp Ala Gly Gly Gln Ser Gln Asp Glu Leu Met Leu Lys
     50                  55                  60

Asp Glu Cys Ile Leu Val Asp Val Glu Asp Asn Ile Thr Gly His Ala
 65                  70                  75                  80

Ser Lys Leu Glu Cys His Lys Phe Leu Pro His Gln Pro Ala Gly Leu
                 85                  90                  95

Leu His Arg Ala Phe Ser Val Phe Leu Phe Asp Asp Gln Gly Arg Leu
            100                 105                 110

Leu Leu Gln Gln Arg Ala Arg Ser Lys Ile Thr Phe Pro Ser Val Trp
        115                 120                 125

Thr Asn Thr Cys Cys Ser His Pro Leu His Gly Gln Thr Pro Asp Glu
    130                 135                 140

Val Asp Gln Leu Ser Gln Val Ala Asp Gly Thr Val Pro Gly Ala Lys
145                 150                 155                 160

Ala Ala Ala Ile Arg Lys Leu Glu His Glu Leu Gly Ile Pro Ala His
                165                 170                 175

Gln Leu Pro Ala Ser Ala Phe Arg Phe Leu Thr Arg Leu His Tyr Cys
            180                 185                 190

Ala Ala Asp Val Gln Pro Ala Ala Thr Gln Ser Ala Leu Trp Gly Glu
        195                 200                 205

His Glu Met Asp Tyr Ile Leu Phe Ile Arg Ala Asn Val Thr Leu Ala
    210                 215                 220

Pro Asn Pro Asp Glu Val Asp Glu Val Arg Tyr Val Thr Gln Glu Glu
225                 230                 235                 240

Leu Arg Gln Met Met Gln Pro Asp Asn Gly Leu Gln Trp Ser Pro Trp
                245                 250                 255

Phe Arg Ile Ile Ala Ala Arg Phe Leu Glu Arg Trp Trp Ala Asp Leu
            260                 265                 270

Asp Ala Ala Leu Asn Thr Asp Lys His Glu Asp Trp Gly Thr Val His
        275                 280                 285

His Ile Asn Glu Ala
            290
```

```
<210> SEQ ID NO 16
<211> LENGTH: 284
<212> TYPE: PRT
<213> ORGANISM: Arabidopsis thaliana

<400> SEQUENCE: 16

Met Ser Val Ser Ser Leu Phe Asn Leu Pro Leu Ile Arg Leu Arg Ser
  1               5                  10                  15

Leu Ala Leu Ser Ser Phe Ser Phe Arg Phe Ala His Arg Pro
             20                  25                  30

Leu Ser Ser Ile Ser Pro Arg Lys Leu Pro Asn Phe Arg Ala Phe Ser
             35                  40                  45

Gly Thr Ala Met Thr Asp Thr Lys Asp Ala Gly Met Asp Ala Val Gln
         50                  55                  60

Arg Arg Leu Met Phe Glu Asp Glu Cys Ile Leu Val Asp Glu Thr Asp
 65                  70                  75                  80

Arg Val Val Gly His Val Ser Lys Tyr Asn Cys His Leu Met Glu Asn
                 85                  90                  95

Ile Glu Ala Lys Asn Leu Leu His Arg Ala Phe Ser Val Phe Leu Phe
            100                 105                 110

Asn Ser Lys Tyr Glu Leu Leu Gln Gln Arg Ser Asn Thr Lys Val
            115                 120                 125

Thr Phe Pro Leu Val Trp Thr Asn Thr Cys Cys Ser His Pro Leu Tyr
130                 135                 140

Arg Glu Ser Glu Leu Ile Gln Asp Asn Ala Leu Gly Val Arg Asn Ala
145                 150                 155                 160

Ala Gln Arg Lys Leu Leu Asp Glu Leu Gly Ile Val Ala Glu Asp Val
                165                 170                 175

Pro Val Asp Glu Phe Thr Pro Leu Gly Arg Met Leu Tyr Lys Ala Pro
            180                 185                 190

Ser Asp Gly Lys Trp Gly Glu His Glu Leu Asp Tyr Leu Leu Phe Ile
            195                 200                 205

Val Arg Asp Val Lys Val Gln Pro Asn Pro Asp Glu Val Ala Glu Ile
        210                 215                 220

Lys Tyr Val Ser Arg Glu Glu Leu Lys Glu Leu Val Lys Lys Ala Asp
225                 230                 235                 240

Ala Gly Glu Glu Gly Leu Lys Leu Ser Pro Trp Phe Arg Leu Val Val
                245                 250                 255

Asp Asn Phe Leu Met Lys Trp Trp Asp His Val Glu Lys Gly Thr Leu
            260                 265                 270

Val Glu Ala Ile Asp Met Lys Thr Ile His Lys Leu
        275                 280

<210> SEQ ID NO 17
<211> LENGTH: 287
<212> TYPE: PRT
<213> ORGANISM: Clarkia breweri

<400> SEQUENCE: 17

Met Ser Ser Ser Met Leu Asn Phe Thr Ala Ser Arg Ile Val Ser Leu
  1               5                  10                  15

Pro Leu Leu Ser Ser Pro Pro Ser Arg Val His Leu Pro Leu Cys Phe
             20                  25                  30

Phe Ser Pro Ile Ser Leu Thr Gln Arg Phe Ser Ala Lys Leu Thr Phe
             35                  40                  45

Ser Ser Gln Ala Thr Thr Met Gly Glu Val Val Asp Ala Gly Met Asp
```

```
            50                  55                  60
Ala Val Gln Arg Arg Leu Met Phe Glu Asp Glu Cys Ile Leu Val Asp
 65                  70                  75                  80

Glu Asn Asp Lys Val Val Gly His Glu Ser Lys Tyr Asn Cys His Leu
                 85                  90                  95

Met Glu Lys Ile Glu Ser Glu Asn Leu Leu His Arg Ala Phe Ser Val
            100                 105                 110

Phe Leu Phe Asn Ser Lys Tyr Glu Leu Leu Leu Gln Gln Arg Ser Ala
        115                 120                 125

Thr Lys Val Thr Phe Pro Leu Val Trp Thr Asn Thr Cys Cys Ser His
130                 135                 140

Pro Leu Tyr Arg Glu Ser Glu Leu Ile Asp Glu Asn Cys Leu Gly Val
145                 150                 155                 160

Arg Asn Ala Ala Gln Arg Lys Leu Leu Asp Glu Leu Gly Ile Pro Ala
                165                 170                 175

Glu Asp Leu Pro Val Asp Gln Phe Ile Pro Leu Ser Arg Ile Leu Tyr
            180                 185                 190

Lys Ala Pro Ser Asp Gly Lys Trp Gly Glu His Glu Leu Asp Tyr Leu
        195                 200                 205

Leu Phe Ile Ile Arg Asp Val Asn Leu Asp Pro Asn Pro Asp Glu Val
210                 215                 220

Ala Glu Val Lys Tyr Met Asn Arg Asp Asp Leu Lys Glu Leu Leu Arg
225                 230                 235                 240

Lys Ala Asp Ala Glu Glu Gly Val Lys Leu Ser Pro Trp Phe Arg
                245                 250                 255

Leu Val Val Asp Asn Phe Leu Phe Lys Trp Trp Asp His Val Glu Lys
            260                 265                 270

Gly Ser Leu Lys Asp Ala Ala Asp Met Lys Thr Ile His Lys Leu
        275                 280                 285

<210> SEQ ID NO 18
<211> LENGTH: 261
<212> TYPE: PRT
<213> ORGANISM: Arabidopsis thaliana

<400> SEQUENCE: 18

Thr Gly Pro Pro Arg Phe Phe Pro Ile Arg Ser Pro Val Pro Arg
 1               5                  10                  15

Thr Gln Leu Phe Val Arg Ala Phe Ser Ala Val Thr Met Thr Asp Ser
                 20                  25                  30

Asn Asp Ala Gly Met Asp Ala Val Gln Arg Arg Leu Met Phe Glu Asp
            35                  40                  45

Glu Cys Ile Leu Val Asp Glu Asn Asn Arg Val Val Gly His Asp Thr
        50                  55                  60

Lys Tyr Asn Cys His Leu Met Glu Lys Ile Glu Ala Glu Asn Leu Leu
65                  70                  75                  80

His Arg Ala Phe Ser Val Phe Leu Phe Asn Ser Lys Tyr Glu Leu Leu
                 85                  90                  95

Leu Gln Gln Arg Ser Lys Thr Lys Val Thr Phe Pro Leu Val Trp Thr
            100                 105                 110

Asn Thr Cys Cys Ser His Pro Leu Tyr Arg Glu Ser Glu Leu Ile Glu
        115                 120                 125

Glu Asn Val Leu Gly Val Arg Asn Ala Ala Gln Arg Lys Leu Phe Asp
    130                 135                 140
```

```
Glu Leu Gly Ile Val Ala Glu Asp Val Pro Val Asp Glu Phe Thr Pro
145                 150                 155                 160

Leu Gly Arg Met Leu Tyr Lys Ala Pro Ser Asp Gly Lys Trp Gly Glu
                165                 170                 175

His Glu Val Asp Tyr Leu Leu Phe Ile Val Arg Asp Val Lys Leu Gln
            180                 185                 190

Pro Asn Pro Asp Glu Val Ala Glu Ile Lys Tyr Val Ser Arg Glu Glu
            195                 200                 205

Leu Lys Glu Leu Val Lys Lys Ala Asp Ala Gly Asp Glu Ala Val Lys
210                 215                 220

Leu Ser Pro Trp Phe Arg Leu Val Asp Asn Phe Leu Met Lys Trp
225                 230                 235                 240

Trp Asp His Val Glu Lys Gly Thr Ile Thr Glu Ala Ala Asp Met Lys
            245                 250                 255

Thr Ile His Lys Leu
            260

<210> SEQ ID NO 19
<211> LENGTH: 288
<212> TYPE: PRT
<213> ORGANISM: Saccharomyces cerevisiae

<400> SEQUENCE: 19

Met Thr Ala Asp Asn Ser Met Pro His Gly Ala Val Ser Ser Tyr
1               5                   10                  15

Ala Lys Leu Val Gln Asn Gln Thr Pro Glu Asp Ile Leu Glu Glu Phe
                20                  25                  30

Pro Glu Ile Ile Pro Leu Gln Gln Arg Pro Asn Thr Arg Ser Ser Glu
            35                  40                  45

Thr Ser Asn Asp Glu Ser Gly Glu Thr Cys Phe Ser Gly His Asp Glu
        50                  55                  60

Glu Gln Ile Lys Leu Met Asn Glu Asn Cys Ile Val Leu Asp Trp Asp
65                  70                  75                  80

Asp Asn Ala Ile Gly Ala Gly Thr Lys Lys Val Cys His Leu Met Glu
                85                  90                  95

Asn Ile Glu Lys Gly Leu Leu His Arg Ala Phe Ser Val Phe Ile Phe
            100                 105                 110

Asn Glu Gln Gly Glu Leu Leu Leu Gln Gln Arg Ala Thr Glu Lys Ile
        115                 120                 125

Thr Phe Pro Asp Leu Trp Thr Asn Thr Cys Cys Ser His Pro Leu Cys
130                 135                 140

Ile Asp Asp Glu Leu Gly Leu Lys Gly Lys Leu Asp Asp Lys Ile Lys
145                 150                 155                 160

Gly Ala Ile Thr Ala Ala Val Arg Lys Leu Asp His Glu Leu Gly Ile
                165                 170                 175

Pro Glu Asp Glu Thr Lys Thr Arg Gly Lys Phe His Phe Leu Asn Arg
            180                 185                 190

Ile His Tyr Met Ala Pro Ser Asn Glu Pro Trp Gly Glu His Glu Ile
        195                 200                 205

Asp Tyr Ile Leu Phe Tyr Lys Ile Asn Ala Lys Glu Asn Leu Thr Val
210                 215                 220

Asn Pro Asn Val Asn Glu Val Arg Asp Phe Lys Trp Val Ser Pro Asn
225                 230                 235                 240

Asp Leu Lys Thr Met Phe Ala Asp Pro Ser Tyr Lys Phe Thr Pro Trp
                245                 250                 255
```

```
Phe Lys Ile Ile Cys Glu Asn Tyr Leu Phe Asn Trp Trp Glu Gln Leu
                260                 265                 270

Asp Asp Leu Ser Glu Val Glu Asn Asp Arg Gln Ile His Arg Met Leu
        275                 280                 285

<210> SEQ ID NO 20
<211> LENGTH: 456
<212> TYPE: PRT
<213> ORGANISM: Artificial Sequence
<220> FEATURE:
<223> OTHER INFORMATION: Description of Artificial Sequence: Consensus
      sequence of four plant B-cyclases

<400> SEQUENCE: 20

Met Asp Thr Leu Leu Lys Thr Pro Asn Leu Glu Phe Leu Pro His Gly
  1               5                  10                  15

Phe Val Lys Ser Phe Ser Lys Phe Gly Lys Cys Glu Gly Val Cys Val
             20                  25                  30

Lys Ser Ser Ala Leu Leu Glu Leu Val Pro Glu Thr Lys Lys Glu Asn
         35                  40                  45

Leu Asp Phe Glu Leu Pro Met Tyr Asp Pro Ser Lys Gly Val Val Asp
     50                  55                  60

Leu Ala Val Val Gly Gly Gly Pro Ala Gly Leu Ala Val Ala Gln Gln
 65                  70                  75                  80

Val Ser Glu Ala Gly Leu Ser Val Cys Ser Ile Asp Pro Pro Lys Leu
                 85                  90                  95

Ile Trp Pro Asn Asn Tyr Gly Val Trp Val Asp Glu Phe Glu Ala Met
            100                 105                 110

Asp Leu Leu Asp Cys Leu Asp Ala Thr Trp Ser Gly Ala Val Tyr Ile
        115                 120                 125

Asp Asp Thr Lys Asp Leu Arg Pro Tyr Gly Arg Val Asn Arg Lys Gln
    130                 135                 140

Leu Lys Ser Lys Met Met Gln Lys Cys Ile Asn Gly Val Lys Phe His
145                 150                 155                 160

Gln Ala Lys Val Ile Lys Val His Glu Glu Lys Ser Met Leu Ile
                165                 170                 175

Cys Asn Asp Gly Thr Ile Gln Ala Thr Val Val Leu Asp Ala Thr Gly
            180                 185                 190

Phe Ser Arg Leu Val Gln Tyr Asp Lys Pro Tyr Asn Pro Gly Tyr Gln
        195                 200                 205

Val Ala Tyr Gly Ile Leu Ala Glu Val Glu Glu His Pro Phe Asp Lys
    210                 215                 220

Met Val Phe Met Asp Trp Arg Asp Ser His Leu Asn Asn Glu Leu Lys
225                 230                 235                 240

Glu Arg Asn Ser Ile Pro Thr Phe Leu Tyr Ala Met Pro Phe Ser Ser
                245                 250                 255

Asn Arg Ile Phe Leu Glu Glu Thr Ser Leu Val Ala Arg Pro Gly Leu
            260                 265                 270

Arg Met Asp Asp Ile Gln Glu Arg Met Val Ala Arg Leu His Leu Gly
        275                 280                 285

Ile Lys Val Lys Ser Ile Glu Glu Asp Glu His Cys Val Ile Pro Met
    290                 295                 300

Gly Gly Pro Leu Pro Val Leu Pro Gln Arg Val Val Gly Ile Gly Gly
305                 310                 315                 320

Thr Ala Gly Met Val His Pro Ser Thr Gly Tyr Met Val Ala Arg Thr
```

-continued

```
                325                 330                 335
Leu Ala Ala Ala Pro Val Val Ala Asn Ala Ile Ile Tyr Leu Gly Ser
                340                 345                 350
Glu Ser Ser Gly Glu Leu Ser Ala Glu Val Trp Lys Asp Leu Trp Pro
                355                 360                 365
Ile Glu Arg Arg Gln Arg Glu Phe Phe Cys Phe Gly Met Asp Ile
370                 375                 380
Leu Leu Lys Leu Asp Leu Pro Ala Thr Arg Arg Phe Phe Asp Ala Phe
385                 390                 395                 400
Phe Asp Leu Glu Pro Arg Tyr Trp His Gly Phe Leu Ser Ser Arg Leu
                405                 410                 415
Phe Leu Pro Glu Leu Ile Val Phe Gly Leu Ser Leu Phe Ser His Ala
                420                 425                 430
Ser Asn Thr Ser Arg Glu Ile Met Thr Lys Gly Thr Pro Leu Val Met
                435                 440                 445
Ile Asn Asn Leu Leu Gln Asp Glu
450                 455

<210> SEQ ID NO 21
<211> LENGTH: 524
<212> TYPE: PRT
<213> ORGANISM: Arabidopsis thaliana

<400> SEQUENCE: 21

Met Glu Cys Val Gly Ala Arg Asn Phe Ala Ala Met Ala Val Ser Thr
1               5                   10                  15
Phe Pro Ser Trp Ser Cys Arg Arg Lys Phe Pro Val Val Lys Arg Tyr
                20                  25                  30
Ser Tyr Arg Asn Ile Arg Phe Gly Leu Cys Ser Val Arg Ala Ser Gly
            35                  40                  45
Gly Gly Ser Ser Gly Ser Glu Ser Cys Val Ala Val Arg Glu Asp Phe
        50                  55                  60
Ala Asp Glu Glu Asp Phe Val Lys Ala Gly Ser Glu Ile Leu Phe
65                  70                  75                  80
Val Gln Met Gln Gln Asn Lys Asp Met Asp Glu Gln Ser Lys Leu Val
                85                  90                  95
Asp Lys Leu Pro Pro Ile Ser Ile Gly Asp Gly Ala Leu Asp His Val
                100                 105                 110
Val Ile Gly Cys Gly Pro Ala Gly Leu Ala Leu Ala Ala Glu Ser Ala
            115                 120                 125
Lys Leu Gly Leu Lys Val Gly Leu Ile Gly Pro Asp Leu Pro Phe Thr
        130                 135                 140
Asn Asn Tyr Gly Val Trp Glu Asp Glu Phe Asn Asp Leu Gly Leu Gln
145                 150                 155                 160
Lys Cys Ile Glu His Val Trp Arg Glu Thr Ile Val Tyr Leu Asp Asp
                165                 170                 175
Asp Lys Pro Ile Thr Ile Gly Arg Ala Tyr Gly Arg Val Ser Arg Arg
                180                 185                 190
Leu Leu His Glu Glu Leu Leu Arg Arg Cys Val Glu Ser Gly Val Ser
            195                 200                 205
Tyr Leu Ser Ser Lys Val Asp Ser Ile Thr Glu Ala Ser Asp Gly Leu
        210                 215                 220
Arg Leu Val Ala Cys Asp Asp Asn Asn Val Ile Pro Cys Arg Leu Ala
225                 230                 235                 240
```

Thr Val Ala Ser Gly Ala Ala Ser Gly Lys Leu Leu Gln Tyr Glu Val
                245                 250                 255

Gly Gly Pro Arg Val Cys Val Gln Thr Ala Tyr Gly Val Glu Val Glu
                260                 265                 270

Val Glu Asn Ser Pro Tyr Asp Pro Asp Gln Met Val Phe Met Asp Tyr
            275                 280                 285

Arg Asp Tyr Thr Asn Glu Lys Val Arg Ser Leu Glu Ala Glu Tyr Pro
        290                 295                 300

Thr Phe Leu Tyr Ala Met Pro Met Thr Lys Ser Arg Leu Phe Phe Glu
305                 310                 315                 320

Glu Thr Cys Leu Ala Ser Lys Asp Val Met Pro Phe Asp Leu Leu Lys
                325                 330                 335

Thr Lys Leu Met Leu Arg Leu Asp Thr Leu Gly Ile Arg Ile Leu Lys
                340                 345                 350

Thr Tyr Glu Glu Glu Trp Ser Tyr Ile Pro Val Gly Gly Ser Leu Pro
                355                 360                 365

Asn Thr Glu Gln Lys Asn Leu Ala Phe Gly Ala Ala Ala Ser Met Val
            370                 375                 380

His Pro Ala Thr Gly Tyr Ser Val Val Arg Ser Leu Ser Glu Ala Pro
385                 390                 395                 400

Lys Tyr Ala Ser Val Ile Ala Glu Ile Leu Arg Glu Glu Thr Thr Lys
                405                 410                 415

Gln Ile Asn Ser Asn Ile Ser Arg Gln Ala Trp Asp Thr Leu Trp Pro
            420                 425                 430

Pro Glu Arg Lys Arg Gln Arg Ala Phe Phe Leu Phe Gly Leu Ala Leu
        435                 440                 445

Ile Val Gln Phe Asp Thr Glu Gly Ile Arg Ser Phe Phe Arg Thr Phe
    450                 455                 460

Phe Arg Leu Pro Lys Trp Met Trp Gln Gly Phe Leu Gly Ser Thr Leu
465                 470                 475                 480

Thr Ser Gly Asp Leu Val Leu Phe Ala Leu Tyr Met Phe Val Ile Ser
                485                 490                 495

Pro Asn Asn Leu Arg Lys Gly Leu Ile Asn His Leu Ile Ser Asp Pro
            500                 505                 510

Thr Gly Ala Thr Met Ile Lys Thr Tyr Leu Lys Val
        515                 520

<210> SEQ ID NO 22
<211> LENGTH: 1898
<212> TYPE: DNA
<213> ORGANISM: Adonis palaestina

<400> SEQUENCE: 22
aaaggagtgt tctattaatg ttactgtcgc attcttgcaa cacttatatt caaactccat    60
tttcttcttt tctcttcaaa caacaaact aatgtgagca gagtatctgg ctatggaact   120
acttggtgtt cgcaacctca tctcttcttg ccctgtgtgg actttgaa caagaaacct    180 tagtagttca aaactagctt ataacataca tcgatatggt tcttcttgta gagtagattt   240
tcaagtgaga gctgatggtg gaagcgggag tagaagttct gttgcttata agagggttt    300 tgtggatgaa gaggatttta tcaaagctgg tggttctgag cttttgtttg tccaaatgca   360
gcaaacaaag tctatggaga aacaggccaa gctcgccgat aagttgccac caataccttt   420
tggagaatcc gtgatggact tggttgtaat aggttgtgga cctgctggtc tttcactggc   480
tgcagaagct gctaagctag ggttgaaagt tggccttatt ggtcctgatc ttccttttac   540

-continued

```
aaataattat ggtgtgtggg aagacgagtt caaagatctt ggacttgaac gttgtatcga    600
gcatgcttgg aaggacacca tcgtatatct tgataatgat gctcctgtcc ttattggtcg    660
tgcatatgga cgagttagtc gacatttgct acatgaggag ttgctgaaaa ggtgtgtgga    720
gtcaggtgta tcatatcttg attctaaagt ggaaaggatc actgaagctg gtgatggcca    780
tagccttgta gtttgtgaaa atgagatctt tatcccttgc aggcttgcta ctgttgcatc    840
tggagcagct tcagggaaac ttttggagta tgaagtaggt ggccctcgtg tttgtgtcca    900
aaccgcttat ggggtggagg ttgaggtgga aacaatccca tacgatccca acttaatggt    960
attcatggac tacagagact atatgcaaca gaaattacag tgctcggaag aagaatatcc   1020
aacatttctc tatgtcatgc ccatgtcgcc aacaagactt ttttttgagg aaacctgttt   1080
ggcctcaaaa gatgccatgc cattcgatct actgaagaga aaactgatgt cacgattgaa   1140
gactctgggt atccaagtta caaagtttta tgaagaggaa tggtcatata ttcctgttgg   1200
tggttcttta ccaaacacag agcaaaagaa cctagcattt ggtgctgcag caagcatggt   1260
gcatccagca acaggctatt cggttgtacg gtcactgtca gaagctccaa aatatgcttc   1320
tgtaattgca aagattttga agcaagataa ctctgcgtat gtggtttctg acaaagtag   1380 tgcagtaaac atttcaatgc aagcatggag cagtctttgg ccaaaggagc gaaaacgtca   1440
aagagcattc tttctttttg gattagagct tattgtgcag ctagatattg aagcaaccag   1500
aacattcttt agaaccttct tccgcttgcc aacttggatg tggtggggtt ccttgggtc   1560 ttcactatca tctttcgatc tcgtcttgtt ttccatgtac atgtttgttt ggcgccaaa   1620 cagcatgagg atgtcacttg tgagacattt gctttcagat ccttctggtg cagttatggt   1680
aagagcttac ctcgaaaggt agtctcatct attattaaac tctagtgttt caccaaataa   1740
atgaggatcc ttcgaatgtg tatatgatca tctctatgta tatcctgtac tctaatctca   1800
taaagtaaat gccgggtttg atattgttgt gtcaaaccgg ccaatgatat aaagtaaatt   1860
tattgataca aaagtagttt ttttccttaa aaaaaaaa                           1898
```

<210> SEQ ID NO 23
<211> LENGTH: 529
<212> TYPE: PRT
<213> ORGANISM: Adonis palaestina

<400> SEQUENCE: 23

```
Met Glu Leu Leu Gly Val Arg Asn Leu Ile Ser Ser Cys Pro Val Trp
  1               5                  10                  15

Thr Phe Gly Thr Arg Asn Leu Ser Ser Ser Lys Leu Ala Tyr Asn Ile
             20                  25                  30

His Arg Tyr Gly Ser Ser Cys Arg Val Asp Phe Gln Val Arg Ala Asp
         35                  40                  45

Gly Gly Ser Gly Ser Arg Ser Ser Val Ala Tyr Lys Glu Gly Phe Val
     50                  55                  60

Asp Glu Glu Asp Phe Ile Lys Ala Gly Ser Glu Leu Leu Phe Val
 65                  70                  75                  80

Gln Met Gln Gln Thr Lys Ser Met Glu Lys Gln Ala Lys Leu Ala Asp
                 85                  90                  95

Lys Leu Pro Pro Ile Pro Phe Gly Glu Ser Val Met Asp Leu Val Val
            100                 105                 110

Ile Gly Cys Gly Pro Ala Gly Leu Ser Leu Ala Ala Glu Ala Ala Lys
        115                 120                 125
```

```
Leu Gly Leu Lys Val Gly Leu Ile Gly Pro Asp Leu Pro Phe Thr Asn
    130                 135                 140
Asn Tyr Gly Val Trp Glu Asp Glu Phe Lys Asp Leu Gly Leu Glu Arg
145                 150                 155                 160
Cys Ile Glu His Ala Trp Lys Asp Thr Ile Val Tyr Leu Asp Asn Asp
                165                 170                 175
Ala Pro Val Leu Ile Gly Arg Ala Tyr Gly Arg Val Ser Arg His Leu
            180                 185                 190
Leu His Glu Glu Leu Leu Lys Arg Cys Val Glu Ser Gly Val Ser Tyr
        195                 200                 205
Leu Asp Ser Lys Val Glu Arg Ile Thr Glu Ala Gly Asp Gly His Ser
    210                 215                 220
Leu Val Val Cys Glu Asn Glu Ile Phe Ile Pro Cys Arg Leu Ala Thr
225                 230                 235                 240
Val Ala Ser Gly Ala Ala Ser Gly Lys Leu Leu Glu Tyr Glu Val Gly
                245                 250                 255
Gly Pro Arg Val Cys Val Gln Thr Ala Tyr Gly Val Glu Val Glu Val
            260                 265                 270
Glu Asn Asn Pro Tyr Asp Pro Asn Leu Met Val Phe Met Asp Tyr Arg
        275                 280                 285
Asp Tyr Met Gln Gln Lys Leu Gln Cys Ser Glu Glu Tyr Pro Thr
    290                 295                 300
Phe Leu Tyr Val Met Pro Met Ser Pro Thr Arg Leu Phe Phe Glu Glu
305                 310                 315                 320
Thr Cys Leu Ala Ser Lys Asp Ala Met Pro Phe Asp Leu Leu Lys Arg
                325                 330                 335
Lys Leu Met Ser Arg Leu Lys Thr Leu Gly Ile Gln Val Thr Lys Val
            340                 345                 350
Tyr Glu Glu Glu Trp Ser Tyr Ile Pro Val Gly Gly Ser Leu Pro Asn
        355                 360                 365
Thr Glu Gln Lys Asn Leu Ala Phe Gly Ala Ala Ala Ser Met Val His
    370                 375                 380
Pro Ala Thr Gly Tyr Ser Val Val Arg Ser Leu Ser Glu Ala Pro Lys
385                 390                 395                 400
Tyr Ala Ser Val Ile Ala Lys Ile Leu Lys Gln Asp Asn Ser Ala Tyr
                405                 410                 415
Val Val Ser Gly Gln Ser Ser Ala Val Asn Ile Ser Met Gln Ala Trp
            420                 425                 430
Ser Ser Leu Trp Pro Lys Glu Arg Lys Arg Gln Arg Ala Phe Phe Leu
        435                 440                 445
Phe Gly Leu Glu Leu Ile Val Gln Leu Asp Ile Glu Ala Thr Arg Thr
    450                 455                 460
Phe Phe Arg Thr Phe Phe Arg Leu Pro Thr Trp Met Trp Gly Phe
465                 470                 475                 480
Leu Gly Ser Ser Leu Ser Ser Phe Asp Leu Val Leu Phe Ser Met Tyr
                485                 490                 495
Met Phe Val Leu Ala Pro Asn Ser Met Arg Met Ser Leu Val Arg His
            500                 505                 510
Leu Leu Ser Asp Pro Ser Gly Ala Val Met Val Arg Ala Tyr Leu Glu
        515                 520                 525

Arg

<210> SEQ ID NO 24
```

<211> LENGTH: 1378
<212> TYPE: DNA
<213> ORGANISM: Solanum tuberosum
<220> FEATURE:
<221> NAME/KEY: modified_base
<222> LOCATION: (7)..(11)
<223> OTHER INFORMATION: a, t, c, g, other or unknown
<220> FEATURE:
<221> NAME/KEY: modified_base
<222> LOCATION: (1180)..(1181)
<223> OTHER INFORMATION: a, t, c, g, other or unknown
<220> FEATURE:
<221> NAME/KEY: modified_base
<222> LOCATION: (1330)
<223> OTHER INFORMATION: a, t, c, g, other or unknown

<400> SEQUENCE: 24

```
tagcggnnnn naggatgagt tcaaagatct tggtcttcaa gcctgcattg aacatgtttg    60
gctgggatac cattgtatat cttgatgatg atgatcctat tcttattggc cgtgcctatg   120
gaagagttag tcgccattta ctgcacgagg agttactcaa aaggtgtgtg gaggcaggtg   180
ttttgtatct aaactcgaaa gtggatagga ttgttgaggc cacaaatggc cacagtcttg   240
tagagtgcga gggtgatgtt gtgattccct gcaggtttgt gactgttgca tcgggagcag   300
cctcggggaa attcttgcag tatgagttgg gaggtcctag agtttctgtt caaacagctt   360
atggagtgga agttgaggtc gataacaatc catttgaccc gagcctgatg gttttcatgg   420
attatagaga ctatgtcaga cacgacgctc aatctttaga agctaaatat ccaacatttc   480
tctatgccat gcccatgtct ccaacacgag tcttttttcga ggaaacttgt ttggcttcaa   540
aagatgcaat gccattcgat ctgttaaaga aaaaattgat gttacgattg aacaccctcg   600
gtgtaagaat taaagaaatt tatgaggagg aatggtctta cataccagtt ggaggatctt   660
tgccaaatac agaacaaaaa acacttgcat ttggtgctgc tgctagcatg gttcatccag   720
ccacaggtta ttcagtcgtc agatcactgt ctgaagctcc aaaatgcgcc ttcgtgcttg   780
caaatatatt acgacaaaat catagcaaga atatgcttac tagttcaagt accccgagta   840
tttcaactca agcttggaac actctttggc cacaagaacg aaaacgacaa agatcgtttt   900
tcctatttgg actggctctg atattgcagc tggatattga ggggataagg tcattttttcc   960
gcgcgttctt ccgtgtgcca aaatggatgt ggcagggatt tcttggttca agtctttctt  1020
agcagacctc atgttatttg ccttctacat gtttattatt gcaccaaatg acatgagaag  1080
aggcttaatc agacatcttt tatctgatcc tactggtgca acattgataa gaacttatct  1140
tacattttag agtaaattcc tcctacaata gttgttgaan nagaggcctc attacttcag  1200
attcataaca gaaatcgcgg tctctcgagg ccttgtatat aacattttca ctaggttaat  1260
attgcttgaa taagttgcac agtttcagtt tttgtatctg cttctttttt gtccaagatc  1320
atgtattgan ccaatttata tacattgcca gtatatataa attttataaa aaaaaaa    1378
```

<210> SEQ ID NO 25
<211> LENGTH: 378
<212> TYPE: PRT
<213> ORGANISM: Solanum tuberosum
<220> FEATURE:
<221> NAME/KEY: MOD_RES
<222> LOCATION: (336)
<223> OTHER INFORMATION: Any amino acid

<400> SEQUENCE: 25

```
Asp Glu Phe Lys Asp Leu Gly Leu Gln Ala Cys Ile Glu His Val Trp
 1               5                  10                  15
```

-continued

```
Arg Asp Thr Ile Val Tyr Leu Asp Asp Asp Pro Ile Leu Ile Gly
         20                  25                  30

Arg Ala Tyr Gly Arg Val Ser Arg His Leu Leu His Glu Glu Leu Leu
         35                  40                  45

Lys Arg Cys Val Glu Ala Gly Val Leu Tyr Leu Asn Ser Lys Val Asp
 50                  55                  60

Arg Ile Val Glu Ala Thr Asn Gly His Ser Leu Val Glu Cys Glu Gly
 65                  70                  75                  80

Asp Val Val Ile Pro Cys Arg Phe Val Thr Val Ala Ser Gly Ala Ala
                 85                  90                  95

Ser Gly Lys Phe Leu Gln Tyr Glu Leu Gly Gly Pro Arg Val Ser Val
             100                 105                 110

Gln Thr Ala Tyr Gly Val Glu Val Glu Val Asp Asn Asn Pro Phe Asp
         115                 120                 125

Pro Ser Leu Met Val Phe Met Asp Tyr Arg Asp Tyr Val Arg His Asp
     130                 135                 140

Ala Gln Ser Leu Glu Ala Lys Tyr Pro Thr Phe Leu Tyr Ala Met Pro
145                 150                 155                 160

Met Ser Pro Thr Arg Val Phe Phe Glu Glu Thr Cys Leu Ala Ser Lys
                 165                 170                 175

Asp Ala Met Pro Phe Asp Leu Leu Lys Lys Lys Leu Met Leu Arg Leu
             180                 185                 190

Asn Thr Leu Gly Val Arg Ile Lys Glu Ile Tyr Glu Glu Trp Ser
         195                 200                 205

Tyr Ile Pro Val Gly Gly Ser Leu Pro Asn Thr Glu Gln Lys Thr Leu
     210                 215                 220

Ala Phe Gly Ala Ala Ala Ser Met Val His Pro Ala Thr Gly Tyr Ser
225                 230                 235                 240

Val Val Arg Ser Leu Ser Glu Ala Pro Lys Cys Ala Phe Val Leu Ala
                 245                 250                 255

Asn Ile Leu Arg Gln Asn His Ser Lys Asn Met Leu Thr Ser Ser Ser
             260                 265                 270

Thr Pro Ser Ile Ser Thr Gln Ala Trp Asn Thr Leu Trp Pro Gln Glu
         275                 280                 285

Arg Lys Arg Gln Arg Ser Phe Phe Leu Phe Gly Leu Ala Leu Ile Leu
     290                 295                 300

Gln Leu Asp Ile Glu Gly Ile Arg Ser Phe Arg Ala Phe Arg
305                 310                 315                 320

Val Pro Lys Trp Met Trp Gln Gly Phe Leu Gly Ser Ser Leu Ser Xaa
                 325                 330                 335

Ala Asp Leu Met Leu Phe Ala Phe Tyr Met Phe Ile Ile Ala Pro Asn
             340                 345                 350

Asp Met Arg Arg Gly Leu Ile Arg His Leu Leu Ser Asp Pro Thr Gly
         355                 360                 365

Ala Thr Leu Ile Arg Thr Tyr Leu Thr Phe
     370                 375
```

<210> SEQ ID NO 26
<211> LENGTH: 533
<212> TYPE: PRT
<213> ORGANISM: Artificial Sequence
<220> FEATURE:
<223> OTHER INFORMATION: Description of Artificial Sequence: Lactuca
      sp./Solanum sp.
<220> FEATURE:
<221> NAME/KEY: MOD_RES

```
<222> LOCATION: (491)
<223> OTHER INFORMATION: Any amino acid

<400> SEQUENCE: 26

Met Glu Cys Phe Gly Ala Arg Asn Met Thr Ala Thr Met Ala Val Phe
 1               5                  10                  15

Thr Cys Pro Arg Phe Thr Asp Cys Asn Ile Arg His Lys Phe Ser Leu
            20                  25                  30

Leu Lys Gly Arg Arg Phe Thr Asn Leu Ser Ala Ser Ser Ser Leu Arg
        35                  40                  45

Gln Ile Lys Cys Ser Ala Lys Ser Asp Arg Cys Val Val Asp Lys Gln
    50                  55                  60

Gly Ile Ser Val Ala Asp Glu Asp Tyr Val Lys Ala Gly Gly Ser
 65                  70                  75                  80

Glu Leu Phe Phe Val Gln Met Gln Arg Thr Lys Ser Met Glu Ser Gln
                85                  90                  95

Ser Lys Leu Ser Glu Lys Leu Ala Gln Ile Pro Ile Gly Asn Cys Ile
            100                 105                 110

Leu Asp Leu Val Val Ile Gly Cys Gly Pro Ala Gly Leu Ala Leu Ala
        115                 120                 125

Ala Glu Ser Ala Lys Leu Gly Leu Asn Val Gly Leu Ile Gly Pro Asp
130                 135                 140

Leu Pro Phe Thr Asn Asn Tyr Gly Val Trp Gln Asp Glu Phe Ile Gly
145                 150                 155                 160

Leu Gly Leu Glu Gly Cys Ile Glu His Ser Trp Lys Asp Thr Leu Val
                165                 170                 175

Tyr Leu Asp Asp Ala Asp Pro Ile Arg Ile Gly Arg Ala Tyr Gly Arg
            180                 185                 190

Val His Arg Asp Leu Leu His Glu Glu Leu Leu Arg Arg Cys Val Glu
        195                 200                 205

Ser Gly Val Ser Tyr Leu Ser Ser Lys Val Glu Arg Ile Thr Glu Ala
    210                 215                 220

Pro Asn Gly Tyr Ser Leu Ile Glu Cys Glu Gly Asn Ile Thr Ile Pro
225                 230                 235                 240

Cys Arg Leu Ala Thr Val Ala Ser Gly Ala Ala Ser Gly Lys Phe Leu
                245                 250                 255

Glu Tyr Glu Leu Gly Gly Pro Arg Val Ser Val Gln Thr Ala Tyr Gly
            260                 265                 270

Val Glu Val Glu Val Asp Asn Asn Pro Phe Asp Pro Ser Leu Met Val
        275                 280                 285

Phe Met Asp Tyr Arg Asp Tyr Val Arg His Asp Ala Gln Ser Leu Glu
    290                 295                 300

Ala Lys Tyr Pro Thr Phe Leu Tyr Ala Met Pro Met Ser Pro Thr Arg
305                 310                 315                 320

Val Phe Phe Glu Glu Thr Cys Leu Ala Ser Lys Asp Ala Met Pro Phe
                325                 330                 335

Asp Leu Leu Lys Lys Leu Met Arg Leu Asn Thr Leu Gly Val
            340                 345                 350

Arg Ile Lys Glu Ile Tyr Glu Glu Trp Ser Tyr Ile Pro Val Gly
        355                 360                 365

Gly Ser Leu Pro Asn Thr Glu Gln Lys Thr Leu Ala Phe Gly Ala Ala
    370                 375                 380

Ala Ser Met Val His Pro Ala Thr Gly Tyr Ser Val Val Arg Ser Leu
385                 390                 395                 400
```

```
Ser Glu Ala Pro Lys Cys Ala Phe Val Leu Ala Asn Ile Leu Arg Gln
                405                 410                 415

Asn His Ser Lys Asn Met Leu Thr Ser Ser Thr Pro Ser Ile Ser
            420                 425                 430

Thr Gln Ala Trp Asn Thr Leu Trp Pro Gln Glu Arg Lys Arg Gln Arg
            435                 440                 445

Ser Phe Phe Leu Phe Gly Leu Ala Leu Ile Leu Gln Leu Asp Ile Glu
            450                 455                 460

Gly Ile Arg Ser Phe Phe Arg Ala Phe Phe Arg Val Pro Lys Trp Met
465                 470                 475                 480

Trp Gln Gly Phe Leu Gly Ser Ser Leu Ser Xaa Ala Asp Leu Met Leu
                485                 490                 495

Phe Ala Phe Tyr Met Phe Ile Ile Ala Pro Asn Asp Met Arg Arg Gly
                500                 505                 510

Leu Ile Arg His Leu Leu Ser Asp Pro Thr Gly Ala Thr Leu Ile Arg
                515                 520                 525

Thr Tyr Leu Thr Phe
            530

<210> SEQ ID NO 27
<211> LENGTH: 374
<212> TYPE: PRT
<213> ORGANISM: Arabidopsis thaliana

<400> SEQUENCE: 27

Glu Asp Glu Phe Asn Asp Leu Gly Leu Gln Lys Cys Ile Glu His Val
1               5                   10                  15

Trp Arg Glu Thr Ile Val Tyr Leu Asp Asp Lys Pro Ile Thr Ile
            20                  25                  30

Gly Arg Ala Tyr Gly Arg Val Ser Arg Arg Leu Leu His Glu Glu Leu
            35                  40                  45

Leu Arg Arg Cys Val Glu Ser Gly Val Ser Tyr Leu Ser Ser Lys Val
    50                  55                  60

Asp Ser Ile Thr Glu Ala Ser Asp Gly Leu Arg Leu Val Ala Cys Asp
65                  70                  75                  80

Asp Asn Asn Val Ile Pro Cys Arg Leu Ala Thr Val Ala Ser Gly Ala
                85                  90                  95

Ala Ser Gly Lys Leu Leu Gln Tyr Glu Val Gly Gly Pro Arg Val Cys
            100                 105                 110

Val Gln Thr Ala Tyr Gly Val Glu Val Glu Val Glu Asn Ser Pro Tyr
            115                 120                 125

Asp Pro Asp Gln Met Val Phe Met Asp Tyr Arg Asp Tyr Thr Asn Glu
    130                 135                 140

Lys Val Arg Ser Leu Glu Ala Glu Tyr Pro Thr Phe Leu Tyr Ala Met
145                 150                 155                 160

Pro Met Thr Lys Ser Arg Leu Phe Phe Glu Glu Thr Cys Leu Ala Ser
                165                 170                 175

Lys Asp Val Met Pro Phe Asp Leu Leu Lys Thr Lys Leu Met Leu Arg
            180                 185                 190

Leu Asp Thr Leu Gly Ile Arg Ile Leu Lys Thr Tyr Glu Glu Glu Trp
            195                 200                 205

Ser Tyr Ile Pro Val Gly Gly Ser Leu Pro Asn Thr Glu Gln Lys Asn
    210                 215                 220

Leu Ala Phe Gly Ala Ala Ala Ser Met Val His Pro Ala Thr Gly Tyr
```

```
225                 230                 235                 240
Ser Val Val Arg Ser Leu Ser Glu Ala Pro Lys Tyr Ala Ser Val Ile
                245                 250                 255

Ala Glu Ile Leu Arg Glu Glu Thr Thr Lys Gln Ile Asn Ser Asn Ile
                260                 265                 270

Ser Arg Gln Ala Trp Asp Thr Leu Trp Pro Pro Glu Arg Lys Arg Gln
            275                 280                 285

Arg Ala Phe Phe Leu Phe Gly Leu Ala Leu Ile Val Gln Phe Asp Thr
        290                 295                 300

Glu Gly Ile Arg Ser Phe Phe Arg Thr Phe Phe Arg Leu Pro Lys Trp
305                 310                 315                 320

Met Trp Gln Gly Phe Leu Gly Ser Thr Leu Thr Ser Gly Asp Leu Val
                325                 330                 335

Leu Phe Ala Leu Tyr Met Phe Val Ile Ser Pro Asn Asn Leu Arg Lys
                340                 345                 350

Gly Leu Ile Asn His Leu Ile Ser Asp Pro Thr Gly Ala Thr Met Ile
            355                 360                 365

Lys Thr Tyr Leu Lys Val
    370

<210> SEQ ID NO 28
<211> LENGTH: 1002
<212> TYPE: DNA
<213> ORGANISM: Adonis palaestina

<400> SEQUENCE: 28
attcatcttc agcagcgctg tcgtactctt tctatatctt cttccatcac taacagtagt      60
cgccgacggt tgaatcggct attcgcctca acgtcaacta tgggtgaagt cactgatgct     120
ggaatggatg ctgttcagaa gcggctcatg ttcgacgacg aatgtatttt ggtggatgag     180
aatgacaagg tcgtcgggca tgattccaaa tacaactgtc atttgatgga aaagatagag     240
gcagaaaatt tgcttcacag agccttcagt gttttcttgt tcaactcaaa atatgaattg     300
cttcttcagc aacgatccgc cacaaaggta acattcccgc tcgtatggac aaacacatgt     360
tgcagtcatc ctctctttcg tgattccgag ctcatagaag aaaattatct cggtgtacga     420
aacgctgcac aaagaaagct tttagacgag ctaggcattc cagctgaaga tgtcccagtt     480
gatgaattta ctcctcttgg tcgcattctt tacaaagctc catctgacgg caaatgggga     540
gagcacgaat tggactatct cctatttatt gtccgagatg tgaaatacga tccaaaccca     600
gatgaagttg ctgatgctaa gtatgttaat cgcgaggagt tgagagagat actgagaaaa     660
gctgatgctg gtgaagaggg actcaagttg tctccttggt ttagattggt tgttgataac     720
tttttgttca gtggtgggga tcatgtagag cagggtacga ttaaggaagt tgctgacatg     780
aaaactatcc acaagttgac ttaagaggac ttctctcctc tgttctacta tttgtttttt     840
gctacaataa gtgggtggtg ataagcagtt tttctgtttt ctttaattta tggcttttga     900
atttgcctcg atgttgaact tgtaacatat ttagacaaat atgagacctt gtaagttgaa     960
tttgaggctg aatttatatt tttgggaaca taataatgtt aa                      1002

<210> SEQ ID NO 29
<211> LENGTH: 1271
<212> TYPE: DNA
<213> ORGANISM: Adonis palaestina

<400> SEQUENCE: 29
```

-continued

| | |
|---|---|
| ttttaaagct ctttcgctcc accaccatca aagccagcca aatttctctg tacaaaagtt | 60 |
| aaaaacaccg ctttgggctt tggcccctcc atatcggaat ccttgtttac gatacgcatc | 120 |
| taaaccagta attctcggtt ttaatttgtt tcctaaatta ggccccttc cggaatcccg | 180 |
| agaattatgt cgtcgatcag gattaatcct ttatatagta tcttctccac caccactaaa | 240 |
| acattatcag cttcgtgttc ttctcccgct gttcatcttc agcagcgttg tacgtactct | 300 |
| ttctatttct tcttccatca ctaacagtcc tcgccgaggg ttgaatcggc tgttcgcctc | 360 |
| aacgtcgact atgggtgaag tcgctgatgc tggtatggat gccgtccaga agcggcttat | 420 |
| gttcgacgat gaatgtattt tggtggatga aatgacaag gtcgtcggac atgattccaa | 480 |
| atacaactgt catttgatgg aaagataga ggcagaaaac ttgcttcaca gagccttcag | 540 |
| tgttttctta ttcaactcaa aatacgagtt gcttcttcag caacgatctg caacgaaggt | 600 |
| aacattcccg ctcgtatgga caaacacctg ttgcagccat cccctcttcc gtgattccga | 660 |
| actcatagaa gaaaattttc tcggggtacg aaacgctgca caaggaagc ttttagacga | 720 |
| gctaggcatt ccagctgaag acgtaccagt tgatgaattc actcctcttg gtcgcattct | 780 |
| ttacaaagct ccatctgacg gaaaatgggg agagcacgaa ctggactatc ttctgtttat | 840 |
| tgtccgagat gtgaaatacg atccaaaccc agatgaagtt gctgacgcta agtacgttaa | 900 |
| tcgcgaggag ttgaaagaga tactgagaaa agctgatgca ggtgaagagg gaataaagtt | 960 |
| gtctccttgg tttagattgg ttgtggataa ctttttgttc aagtggtggg atcatgtaga | 1020 |
| ggaggggaag attaaggacg tcgccgacat gaaaactatc cacaagttga cttaagagaa | 1080 |
| agtctcttaa gttctactat ttggtttttg cttcaataag tggatggtga tgagcagttt | 1140 |
| ttatgcttcc tttaattttg cttttcaat ttgctttatg tgttgaactt gtaacatatt | 1200 |
| tagtcaaata tgagaccttg tgagttgaat ttgaggttat atttatagtt ttgggaacat | 1260 |
| aaaaaaaaa a | 1271 |

<210> SEQ ID NO 30
<211> LENGTH: 1109
<212> TYPE: DNA
<213> ORGANISM: Haematococcus pluvialis

<400> SEQUENCE: 30

| | |
|---|---|
| tggaacctgg cccggcggca gtccgatgcc gcgatgcttc gttcgttgct cagaggcctc | 60 |
| acgcatatcc cgcgcgtgaa ctccgcccag cagcccagct gtgcacacgc gcgactccag | 120 |
| tttaagctca ggagcatgca gctgcttgcc gaggaccgca cagaccacat gagggtgca | 180 |
| agcacctggg caggcgggca gtcgcaggat gagctgatgc tgaaggacga gtgcatctta | 240 |
| gtggatgctg acgacaacat cacaggccat gccagcaagc tggagtgcca caaattccta | 300 |
| ccacatcagc ctgcaggcct gctgcaccgg gccttctctg tgttcctgtt tgacgaccag | 360 |
| gggcgactgc tgctgcaaca gcgtgcacgc tcaaaaatca ccttcccaag tgtgtggacg | 420 |
| aacacctgct gcagccaccc tctacatggg cagaccccag atgaggtgga ccaactaagc | 480 |
| caggtggccg acgcacagt acctggcgca aaagctgctg ccatccgcaa gttggagcac | 540 |
| gagctgggga taccagcgca ccagctgccg gcaagcgcgt ttcgcttcct cacgcgtttg | 600 |
| cactactgtg ccgcggacgt gcagccggct gcgacacaat cagcgctctg gggcgagcac | 660 |
| gagatggact acatcttatt catccgggcc aacgtcacct ggcgcccaa ccctgacgag | 720 |
| gtggacgaag tcaggtacgt gacgcaagag gagctgcggc agatgatgca gccggacaac | 780 |
| gggttgcaat ggtcgccgtg gtttcgcatc atcgccgcgc gcttccttga gcgttggtgg | 840 |

```
gctgacctgg acgcggccct aaacactgac aaacacgagg attggggaac ggtgcatcac    900
atcaacgaag cgtgaaggca gaagctgcag gatgtgaaga cacgtcatgg ggtggaattg    960
cgtacttggc agcttcgtat ctccttttc tgagactgaa cctgcagagc tagagtcaat   1020
ggtgcatcat attcatcgtc tctcttttgt tttagactaa tctgtagcta gagtcactga   1080
tgaatccttt acaactttca aaaaaaaaa                                     1109

<210> SEQ ID NO 31
<211> LENGTH: 985
<212> TYPE: DNA
<213> ORGANISM: Lactuca sativa

<400> SEQUENCE: 31
tgccaaaatg ttgaaatttc ccccttttaa aaccattgct accatgatct cttctccata     60
ttcttccttc ttgctgcctc ggaaatcttc tttcctcca atgccgtctc tcgcagccgc    120
tagtgttttc ctccaccctc tttcgtctgc cgctatgggc gattccagca tggatgctgt    180
ccagcgacgt ctcatgttcg atgacgaatg cattttggtg gatgagaatg acaaagtggt    240
tggccatgat actaaataca attgtcattt gatggagaag attgaaaagg gaaatatgct    300
acacagagca ttcagtgtgt tcttgttcaa ctcgaaatat gaattactcc ttcagcaacg    360
ttctgcaacc aaggtgactt tccctttggt atggacaaac acgtgttgca gccatccact    420 atacaggag agtgagctta ttgacgaaaa cgcccttggg gtgaggaatg ctgcacagag    480
gaagctcctg gatgaactcg gcatccctgg agcagatgtt ccggttgatg agttcactcc    540
attgggtcgc attctataca aggccgcatc ggatggaaag tggggagaac atgaacttga    600
ttacctgctg tttatggtac gtgatgttgg tttggatccg aacccagatg aagtgaaaga    660
tgtaaaatat gtgaaccggg aagagctgaa ggaattggta aggaaggcgg atgctggtga    720
agagggtgtg aagctgtccc cgtggttcaa attgattgtc gataatttct tgtttcagtg    780
gtgggatcga ctccataagg gaaccctaac cgaagctatt gatatgaaaa caatccacaa    840
actcacataa aaacactaca ctagtaggag agaggattat atgagatatt tgttatatgt    900
gaaattgaaa ttcagatgaa tgcttgtatt tatttctatt tggacaaact tcaacttctt    960
tttgctacct tatcagaaaa aaaaa                                          985

<210> SEQ ID NO 32
<211> LENGTH: 988
<212> TYPE: DNA
<213> ORGANISM: Lactuca sativa

<400> SEQUENCE: 32
tattcgcttc aaaatctctt ccattaactg ctcaaatctc caccttcgcc ggtcttaatc     60
tccgccggcg cactttcacc accataaccg ccgccatggg tgacgattcc ggcatggacg    120
ctgtccagag acgtctcatg tttgatgatg aatgcatttt ggttgatgaa atgacaatg    180 ttcttgggca tgataccaaa tacaattgtc acttgatgga agattgag aaagataatt    240 tgcttcatag agcattcagt gtatttttat tcaattcaaa atacgaatta ctccttcagc    300
aaaggtcaga aaccaaggtg acatttcctt tggtatggac aaacacctgt tgcagccatc    360
cactatacag agaatcggag ttaattcccg aaaatgccct tggggtcaga aatgctgcac    420
agaggaagct tctagatgaa ctcggtatcc ctgctgaaga tgttccagtt gatgagttca    480
caactttagg tcgcatgttg tacaaggctc catctgatgg aaaatggggt gaacatgaag    540
```

-continued

```
ttgattacct actcttcctc gtgcgtgacg ttgccgtgaa cccaaaccct gatgaggtgg    600
cggacattag atacgtgaac caagaagagt taaaagagtt actaaggaag gcggatgcgg    660
gtgaggaggg tttgaaattg tccccatggt ttaggctagt ggtggacaac ttcttgttca    720
aatggtggga tcatgtccaa aaggggacac tcaatgaagc aattgacatg aaaaccattc    780
ataagttgat atgaaaaatg gttaatattt atggtggtgg tttggagcta ataatttgtg    840
tgttcaagtc tcggtccttc ttttttaac gtttttttt tttcttttat tgggagtgtt    900
tattgtgtac ttgtaacgta ggcccttttgg ttacgcttta agagtttaat aaagaaccac    960
cgttaattta aaaaaaaaaa aaaaaaa                                        988
```

<210> SEQ ID NO 33
<211> LENGTH: 1874
<212> TYPE: DNA
<213> ORGANISM: Chlamydomonas reinhardtii

<400> SEQUENCE: 33

```
ggcacgagct cgagtttgtt ttaccatgac atcgggaatt tggaagcttg aactacctca     60
attactcaag taactcgcgg caacacattt cgcgcgccat cgctgttttc tctgctccag    120
ctaccgagca gcattgcttt agatcgcttt gatgtcataa actcccactt atatgagatc    180
cagtttcatc gagcccaagc ccagagcgca acctgtctta gccgcggca gggcgtccat    240 gcgcctcgcg caaagccgtg ctctcgttgc gcgtgtcagc tccgccctgt ggccgggagc    300
aggactttca caggctcaaa gcgttgcggt gcgaatggcg agttcgtcaa cctgggaagg    360
cacgggcctg agccaggatg acttcatgca gcgggacgag tgcttggtgg tggacgagca    420
ggaccggctc taggcaccg ccaacaagta cgactgccac cgcttcgagg cggccaaggg    480
ccagccctgc ggccgcctgc accgcgcctt ctccgtgttc ctgttcagcc cgacggccg    540 actgctgctg cagcagcgcg cagccagcaa ggtgacgttc ccgggtgtgt ggaccaacac    600
ctgctgctcg caccgctgg cgggccaggc gccggacgag gtggacctgc cggcggcggt    660
agcctcgggc caggtgccgg gcatcaaggc ggcggcggtg cgcaagctgc agcacgagct    720
ggggataccg ccggagcagg ttcccgcctc ctccttctcc ttcctcacgc gtctgcacta    780
ctgcgccgcc gacaccgcca cgcacggccc ggcggcggag tggggcgagc acgaggtgga    840
ctacgtgctg ttcgtgcggc cgcagcagcc cgtcagcctg cagcccaacc cagacgaggt    900
ggacgccacg cgctacgtga cgctgccgga gcttcagtcc atgatggcgg accccggcct    960
cagctggagc ccctggttcc gcatcctggc cacacagccc gccttcctgc ccgcctggtg   1020
gggcgacctg aagcggcgct ggcgcccggg cggcagccga ctgtcggact ggggcaccat   1080
ccaccgcgtc atgtgaagaa aaaggggaag caggggcggg agcgggggat gaatgggaat   1140
gtgaatgcga ttgtgatgcg gcgtgggatg aggtctgaag acaggggaa aatcggggggg   1200 cgggcgtgag cgtgtgtgta cgtgagcgac aaagccggga ggcggaccgc gcgatgggta   1260
catgtgtgtg cggagggtcg gtgggtcggt cggttgcgcg gcatagcgtg ttgtgtgtgt   1320
gcggctgcag gggtatgtgg gcacccgggc acgaggagga aggcacacgc aggtggcgcg   1380
gaggtgtgtc agggggccatg ggcgggcctc actcctggtc gtgcccagtg gtctcgtggg   1440
cagagtggca gggctgcac ccatatgagc ggcgcactgc cgcgctgggc taagtcctta   1500
tcacttggtg aggtgggggcg aggtggctgt gggcggcggg cgcagtggca gaaggacacg   1560
gtgtgtgagc ggtggagctc tggccgtgcc ggccgtgagg ggcggatagc gatatgacgt   1620
tgtgcttggc cgctgtaatg cgggagaatg tgcaggccgc gagaagcggg cggtggcagg   1680
```

-continued

| aggccgcagg | ctgcagcacc | cgttggggag | gtgccacctg | caggcgcggc | gccgggcggg | 1740 |
| cctgagtaat | gggcgcctga | gtagtggcgg | ccacaggagg | cgcaggaggc | agcagcagga | 1800 |
| ggacgagctg | gagggacccg | ttggcaaccc | aaggttgcgc | gtgtaacata | gtggccatac | 1860 |
| aaaaaaaaaa | aaaa       |            |            |            |            | 1874 |

<210> SEQ ID NO 34
<211> LENGTH: 954
<212> TYPE: DNA
<213> ORGANISM: Tagetes erecta

<400> SEQUENCE: 34

| ccaaaaacaa | ctcaaatctc | ctccgtcgct | cttactccgc | catgggtgac | gactccggca | 60 |
| tggatgctgt | tcagcgacgt | ctcatgtttg | acgatgaatg | cattttggtg | gatgagtgtg | 120 |
| acaatgtggt | gggacatgat | accaaataca | attgtcactt | gatggagaag | attgaaacag | 180 |
| gtaaaatgct | gcacagagca | ttcagcgttt | ttctattcaa | ttcaaaatac | gagttacttc | 240 |
| ttcagcaacg | gtctgcaacc | aaggtgacat | tcctttagt | atggaccaac | acctgttgca | 300 |
| gccatccact | ctacagagaa | tccgagcttg | ttcccgaaaa | cgcccttgga | gtaagaaatg | 360 |
| ctgcacagag | gaagctgttg | gatgaactcg | gtatccctgc | tgaagatgtt | cccgttgatc | 420 |
| agtttactcc | tttaggtcgc | atgctctaca | aggctccatc | tgatggaaag | tggggagaac | 480 |
| atgaacttga | ctacctactt | ttcatagtga | gagacgttgc | tgtaaacccg | aacccagatg | 540 |
| aagtggcgga | tatcaaatat | gtgaccagaa | gagttaaagg | agctgctaag | gaaagcagat | 600 |
| gcggggagg  | agggtttgaa | gctgtctcca | tggttcaggt | tagtggttga | taacttcttg | 660 |
| ttcaagtggt | gggatcatgt | gcaaaagggt | acactcactg | aagcaattga | tatgaaaacc | 720 |
| atacacaagc | tgatatagaa | acacaccctc | aaccgaaaag | ttcaagccta | ataattcggg | 780 |
| ttgggtcggg | tctaccatca | attgtttttt | tcttttaaga | agttttaatc | tctatttgag | 840 |
| catgttgatt | cttgtctttt | gtgtgtaaga | ttttgggttt | cgtttcagtt | gtaataatga | 900 |
| accattgatg | gtttgcaatt | tcaagttcct | atcgacatgt | agtgatctaa | aaaa       | 954 |

<210> SEQ ID NO 35
<211> LENGTH: 1031
<212> TYPE: DNA
<213> ORGANISM: Oryza sativa

<400> SEQUENCE: 35

| cctcccttg  | cctcgcgcag | aggcggccgc | gccttctccg | ccgcgaggat | ggccggcgcc | 60 |
| gccgccgccg | tggaggacgc | cgggatggac | gaggtccaga | agcggctcat | gttcgacgac | 120 |
| gaatgcattt | tggtggatga | acaagacaat | gttgttggcc | atgaatcaaa | atataactgc | 180 |
| catctgatgg | aaaaaatcga | atctgaaaat | ctacttcata | gggctttcag | tgtattcctg | 240 |
| ttcaactcaa | aatatgaact | cctactccag | caacgatctg | caacaaaggt | tacatttcct | 300 |
| ctagtttgga | ccaacacttg | ctgcagccat | cctctgtacc | gtgagtctga | gcttatacag | 360 |
| gaaaactacc | ttggtgttag | aaatgctgct | cagaggaagc | tcttggatga | gctgggcatc | 420 |
| ccagctgaag | atgtgccagt | tgaccaattc | acccctcttg | gtcggatgct | ttacaaggcc | 480 |
| ccatctgatg | gaaaatgggg | tgaacacgag | cttgactacc | tgctgttcat | cgtccgcgac | 540 |
| gtgaaggtag | tcccgaaccc | ggacgaagtg | gccgatgtga | aatacgtgag | ccgtgagcag | 600 |
| ctgaaggagc | tcatccgcaa | agcggacgcc | ggagaggaag | gcctgaagct | gtctccctgg | 660 |
| ttccggctgg | ttgttgacaa | cttcctcatg | ggctggtggg | atcacgtcga | gaaaggcacc | 720 |

-continued

```
ctcaacgagg ccgtggacat ggagaccatc cacaagctga agtaaggact gcgatgttgt    780
ggctggaaag aatgatcctg aagactctgt tcttgtgctg ctgcatatta ctcttaccag    840
ggaagttgca gaagtcagaa gaagcttttg tatgtttctg ggtttggagc ttggaagtgt    900
tgggctctgc tgactgagag attcccttat agagtgtcta tgttaattta gcaaacttct    960
atattataca tgattagtta attgttcggt gtctgaataa agaacaatag catgttccat   1020
gtttatttgc t                                                        1031
```

<210> SEQ ID NO 36
<211> LENGTH: 232
<212> TYPE: PRT
<213> ORGANISM: Tagetes erecta

<400> SEQUENCE: 36

```
Met Gly Asp Asp Ser Gly Met Asp Ala Val Gln Arg Arg Leu Met Phe
  1               5                  10                  15

Asp Asp Glu Cys Ile Leu Val Asp Glu Cys Asp Asn Val Val Gly His
                 20                  25                  30

Asp Thr Lys Tyr Asn Cys His Leu Met Glu Lys Ile Glu Thr Gly Lys
             35                  40                  45

Met Leu His Arg Ala Phe Ser Val Phe Leu Phe Asn Ser Lys Tyr Glu
         50                  55                  60

Leu Leu Leu Gln Gln Arg Ser Ala Thr Lys Val Thr Phe Pro Leu Val
 65                  70                  75                  80

Trp Thr Asn Thr Cys Cys Ser His Pro Leu Tyr Arg Glu Ser Glu Leu
                 85                  90                  95

Val Pro Glu Asn Ala Leu Gly Val Arg Asn Ala Ala Gln Arg Lys Leu
                100                 105                 110

Leu Asp Glu Leu Gly Ile Pro Ala Glu Asp Val Pro Val Asp Gln Phe
            115                 120                 125

Thr Pro Leu Gly Arg Met Leu Tyr Lys Ala Pro Ser Asp Gly Lys Trp
        130                 135                 140

Gly Glu His Glu Leu Asp Tyr Leu Leu Phe Ile Val Arg Asp Val Ala
145                 150                 155                 160

Val Asn Pro Asn Pro Asp Glu Val Ala Asp Ile Lys Tyr Val Ser His
                165                 170                 175

Glu Glu Leu Lys Glu Leu Leu Arg Lys Ala Asp Ala Gly Glu Glu Gly
            180                 185                 190

Leu Lys Leu Ser Pro Trp Phe Arg Leu Val Val Asp Asn Phe Leu Phe
        195                 200                 205

Lys Trp Trp Asp His Val Gln Lys Gly Thr Leu Thr Glu Ala Ile Asp
    210                 215                 220

Met Lys Thr Ile His Lys Leu Ile
225                 230
```

<210> SEQ ID NO 37
<211> LENGTH: 280
<212> TYPE: PRT
<213> ORGANISM: Lactuca Sativa

<400> SEQUENCE: 37

```
Met Leu Lys Phe Pro Pro Phe Lys Thr Ile Ala Thr Met Ile Ser Ser
  1               5                  10                  15

Pro Tyr Ser Ser Phe Leu Leu Pro Arg Lys Ser Ser Phe Pro Pro Met
                 20                  25                  30
```

```
Pro Ser Leu Ala Ala Ser Val Phe Leu His Pro Leu Ser Ser Ala
        35                  40                  45

Ala Met Gly Asp Ser Ser Met Asp Ala Val Gln Arg Arg Leu Met Phe
 50                  55                  60

Asp Asp Glu Cys Ile Leu Val Asp Glu Asn Asp Lys Val Val Gly His
 65                  70                  75                  80

Asp Thr Lys Tyr Asn Cys His Leu Met Glu Lys Ile Glu Lys Gly Asn
                 85                  90                  95

Met Leu His Arg Ala Phe Ser Val Phe Leu Phe Asn Ser Lys Tyr Glu
                100                 105                 110

Leu Leu Leu Gln Gln Arg Ser Ala Thr Lys Val Thr Phe Pro Leu Val
            115                 120                 125

Trp Thr Asn Thr Cys Cys Ser His Pro Leu Tyr Arg Glu Ser Glu Leu
        130                 135                 140

Ile Asp Glu Asn Ala Leu Gly Val Arg Asn Ala Ala Gln Arg Lys Leu
145                 150                 155                 160

Leu Asp Glu Leu Gly Ile Pro Gly Ala Asp Val Pro Val Asp Glu Phe
                165                 170                 175

Thr Pro Leu Gly Arg Ile Leu Tyr Lys Ala Ala Ser Asp Gly Lys Trp
                180                 185                 190

Gly Glu His Glu Leu Asp Tyr Leu Leu Phe Met Val Arg Asp Val Gly
            195                 200                 205

Leu Asp Pro Asn Pro Asp Glu Val Lys Asp Val Lys Tyr Val Asn Arg
        210                 215                 220

Glu Glu Leu Lys Glu Leu Val Arg Lys Ala Asp Ala Gly Glu Gly
225                 230                 235                 240

Val Lys Leu Ser Pro Trp Phe Lys Leu Ile Val Asp Asn Phe Leu Phe
                245                 250                 255

Gln Trp Trp Asp Arg Leu His Lys Gly Thr Leu Thr Glu Ala Ile Asp
                260                 265                 270

Met Lys Thr Ile His Lys Leu Thr
            275                 280

<210> SEQ ID NO 38
<211> LENGTH: 229
<212> TYPE: PRT
<213> ORGANISM: Lactuca Sativa

<400> SEQUENCE: 38

Met Gly Asp Asp Ser Gly Met Asp Ala Val Gln Arg Arg Leu Met Phe
 1               5                  10                  15

Asp Asp Glu Cys Ile Leu Val Asp Glu Asn Asp Asn Val Leu Gly His
                 20                  25                  30

Asp Thr Lys Tyr Asn Cys His Leu Met Glu Lys Ile Glu Lys Asp Asn
                 35                  40                  45

Leu Leu His Arg Ala Phe Ser Val Phe Leu Phe Asn Ser Lys Tyr Glu
             50                  55                  60

Leu Leu Leu Gln Gln Arg Ser Glu Thr Lys Val Thr Phe Pro Leu Val
 65                  70                  75                  80

Trp Thr Asn Thr Cys Cys Ser His Pro Leu Tyr Arg Glu Ser Glu Leu
                 85                  90                  95

Ile Pro Glu Asn Ala Leu Gly Val Arg Asn Ala Ala Gln Arg Lys Leu
                100                 105                 110

Leu Asp Glu Leu Gly Ile Pro Ala Glu Asp Val Pro Val Asp Glu Phe
```

-continued

```
                115                 120                 125
Thr Thr Leu Gly Arg Met Leu Tyr Lys Ala Pro Ser Asp Gly Lys Trp
    130                 135                 140

Gly Glu His Glu Val Asp Tyr Leu Leu Phe Leu Val Arg Asp Val Ala
145                 150                 155                 160

Val Asn Pro Asn Pro Asp Glu Val Ala Asp Ile Arg Tyr Val Asn Gln
                165                 170                 175

Glu Glu Leu Lys Glu Leu Leu Arg Lys Ala Asp Ala Gly Glu Glu Gly
            180                 185                 190

Leu Lys Leu Ser Pro Trp Phe Arg Leu Val Val Asp Asn Phe Leu Phe
        195                 200                 205

Lys Trp Trp Asp His Val Gln Lys Gly Thr Leu Asn Glu Ala Ile Asp
    210                 215                 220

Met Lys Thr Ile His
225
```

<210> SEQ ID NO 39
<211> LENGTH: 295
<212> TYPE: PRT
<213> ORGANISM: Adonis Palaestina

<400> SEQUENCE: 39

```
Met Ser Ser Ile Arg Ile Asn Pro Leu Tyr Ser Ile Phe Ser Thr Thr
 1               5                  10                  15

Thr Lys Thr Leu Ser Ala Ser Cys Ser Ser Pro Ala Val His Leu Gln
            20                  25                  30

Gln Arg Cys Arg Thr Leu Ser Ile Ser Ser Ser Ile Thr Asn Ser Pro
        35                  40                  45

Arg Arg Gly Leu Asn Arg Leu Phe Ala Ser Thr Ser Thr Met Gly Glu
    50                  55                  60

Val Ala Asp Ala Gly Met Asp Ala Val Gln Lys Arg Leu Met Phe Asp
65                  70                  75                  80

Asp Glu Cys Ile Leu Val Asp Glu Asn Asp Lys Val Val Gly Tyr Asp
                85                  90                  95

Ser Lys Tyr Asn Cys His Leu Met Glu Lys Ile Glu Ala Glu Asn Leu
            100                 105                 110

Leu His Arg Ala Phe Ser Val Phe Leu Phe Asn Ser Lys Tyr Glu Leu
        115                 120                 125

Leu Leu Gln Gln Arg Ser Ala Thr Lys Val Thr Phe Pro Leu Val Trp
    130                 135                 140

Thr Asn Thr Cys Cys Ser His Pro Leu Phe Arg Asp Ser Glu Leu Ile
145                 150                 155                 160

Glu Glu Asn Phe Leu Gly Val Arg Asn Ala Ala Gln Arg Lys Leu Leu
                165                 170                 175

Asp Glu Leu Gly Ile Pro Ala Glu Asp Val Pro Val Asp Glu Phe Thr
            180                 185                 190

Pro Leu Gly Arg Ile Leu Tyr Lys Ala Pro Ser Asp Gly Lys Trp Gly
        195                 200                 205

Glu His Glu Leu Asp Tyr Leu Leu Phe Ile Val Arg Asp Val Lys Tyr
    210                 215                 220

Asp Pro Asn Pro Asp Glu Val Ala Asp Ala Lys Tyr Val Asn Arg Glu
225                 230                 235                 240

Glu Leu Lys Glu Ile Leu Arg Lys Ala Asp Ala Gly Glu Glu Gly Ile
                245                 250                 255
```

```
Lys Leu Ser Pro Trp Phe Arg Leu Val Asp Asn Phe Leu Phe Lys
            260                 265                 270

Trp Trp Asp His Val Glu Glu Gly Lys Ile Lys Asp Val Ala Asp Met
        275                 280                 285

Lys Thr Ile His Lys Leu Thr
    290                 295

<210> SEQ ID NO 40
<211> LENGTH: 234
<212> TYPE: PRT
<213> ORGANISM: Adonis Palaestina

<400> SEQUENCE: 40

Met Gly Glu Val Thr Asp Ala Gly Met Asp Ala Val Gln Lys Arg Leu
 1               5                  10                  15

Met Phe Asp Asp Glu Cys Ile Leu Val Asp Glu Asn Asp Lys Val Val
                20                  25                  30

Gly His Asp Ser Lys Tyr Asn Cys His Leu Met Glu Lys Ile Glu Ala
            35                  40                  45

Glu Asn Leu Leu His Arg Ala Phe Ser Val Phe Leu Phe Asn Ser Lys
        50                  55                  60

Tyr Glu Leu Leu Leu Gln Gln Arg Ser Ala Thr Lys Val Thr Phe Pro
 65                  70                  75                  80

Leu Val Trp Thr Asn Thr Cys Cys Ser His Pro Leu Phe Arg Asp Ser
                85                  90                  95

Glu Leu Ile Glu Glu Asn Tyr Leu Gly Val Arg Asn Ala Ala Gln Arg
            100                 105                 110

Lys Leu Leu Asp Glu Leu Gly Ile Pro Ala Glu Asp Val Pro Val Asp
        115                 120                 125

Glu Phe Thr Pro Leu Gly Arg Ile Leu Tyr Lys Ala Pro Ser Asp Gly
    130                 135                 140

Lys Trp Gly Glu His Glu Leu Asp Tyr Leu Leu Phe Ile Val Arg Asp
145                 150                 155                 160

Val Lys Tyr Asp Pro Asn Pro Asp Glu Val Ala Asp Ala Lys Tyr Val
                165                 170                 175

Asn Arg Glu Glu Leu Arg Glu Ile Leu Arg Lys Ala Asp Ala Gly Glu
            180                 185                 190

Glu Gly Leu Lys Leu Ser Pro Trp Phe Arg Leu Val Val Asp Asn Phe
        195                 200                 205

Leu Phe Lys Trp Trp Asp His Val Glu Gln Gly Thr Ile Lys Glu Val
    210                 215                 220

Ala Asp Met Lys Thr Ile His Lys Leu Thr
225                 230

<210> SEQ ID NO 41
<211> LENGTH: 238
<212> TYPE: PRT
<213> ORGANISM: Oryza Sativa

<400> SEQUENCE: 41

Met Ala Gly Ala Ala Ala Ala Val Glu Asp Ala Gly Met Asp Glu Val
 1               5                  10                  15

Gln Lys Arg Leu Met Phe Asp Asp Glu Cys Ile Leu Val Asp Glu Gln
                20                  25                  30

Asp Asn Val Val Gly His Glu Ser Lys Tyr Asn Cys His Leu Met Glu
            35                  40                  45
```

```
Lys Ile Glu Ser Glu Asn Leu Leu His Arg Ala Phe Ser Val Phe Leu
         50                  55                  60

Phe Asn Ser Lys Tyr Glu Leu Leu Gln Gln Arg Ser Ala Thr Lys
 65                  70                  75                  80

Val Thr Phe Pro Leu Val Trp Thr Asn Thr Cys Cys Ser His Pro Leu
                 85                  90                  95

Tyr Arg Glu Ser Glu Leu Ile Gln Glu Asn Tyr Leu Gly Val Arg Asn
                100                 105                 110

Ala Ala Gln Arg Lys Leu Leu Asp Glu Leu Gly Ile Pro Ala Glu Asp
            115                 120                 125

Val Pro Val Asp Gln Phe Thr Pro Leu Gly Arg Met Leu Tyr Lys Ala
        130                 135                 140

Pro Ser Asp Gly Lys Trp Gly Glu His Glu Leu Asp Tyr Leu Leu Phe
145                 150                 155                 160

Ile Val Arg Asp Val Lys Val Val Pro Asn Pro Asp Glu Val Ala Asp
                165                 170                 175

Val Lys Tyr Val Ser Arg Glu Gln Leu Lys Glu Leu Ile Arg Lys Ala
                180                 185                 190

Asp Ala Gly Glu Glu Gly Leu Lys Leu Ser Pro Trp Phe Arg Leu Val
            195                 200                 205

Val Asp Asn Phe Leu Met Gly Trp Trp Asp His Val Glu Lys Gly Thr
        210                 215                 220

Leu Asn Glu Ala Val Asp Met Glu Thr Ile His Lys Leu Lys
225                 230                 235

<210> SEQ ID NO 42
<211> LENGTH: 233
<212> TYPE: PRT
<213> ORGANISM: Arabidopsis thaliana

<400> SEQUENCE: 42

Met Thr Asp Ser Asn Asp Ala Gly Met Asp Ala Val Gln Arg Arg Leu
  1               5                  10                  15

Met Phe Glu Asp Glu Cys Ile Leu Val Asp Glu Asn Asn Arg Val Val
             20                  25                  30

Gly His Asp Thr Lys Tyr Asn Cys His Leu Met Glu Lys Ile Glu Ala
         35                  40                  45

Glu Asn Leu Leu His Arg Ala Phe Ser Val Phe Leu Phe Asn Ser Lys
     50                  55                  60

Tyr Glu Leu Leu Leu Gln Gln Arg Ser Lys Thr Lys Val Thr Phe Pro
 65                  70                  75                  80

Leu Val Trp Thr Asn Thr Cys Cys Ser His Pro Leu Tyr Arg Glu Ser
                 85                  90                  95

Glu Leu Ile Glu Glu Asn Val Leu Gly Val Arg Asn Ala Ala Gln Arg
                100                 105                 110

Lys Leu Phe Asp Glu Leu Gly Ile Val Ala Glu Asp Val Pro Val Asp
            115                 120                 125

Glu Phe Thr Pro Leu Gly Arg Met Leu Tyr Lys Ala Pro Ser Asp Gly
        130                 135                 140

Lys Trp Gly Glu His Glu Val Asp Tyr Leu Leu Phe Ile Val Arg Asp
145                 150                 155                 160

Val Lys Leu Gln Pro Asn Pro Asp Glu Val Ala Glu Ile Lys Tyr Val
                165                 170                 175

Ser Arg Glu Glu Leu Lys Glu Leu Val Lys Lys Ala Asp Ala Gly Asp
                180                 185                 190
```

-continued

```
Glu Ala Val Lys Leu Ser Pro Trp Phe Arg Leu Val Asp Asn Phe
            195                 200                 205

Leu Met Lys Trp Trp Asp His Val Glu Lys Gly Thr Ile Thr Glu Ala
    210                 215                 220

Ala Asp Met Lys Thr Ile His Lys Leu
225                 230

<210> SEQ ID NO 43
<211> LENGTH: 293
<212> TYPE: PRT
<213> ORGANISM: Haematococcus pluvialis

<400> SEQUENCE: 43

Met Leu Arg Ser Leu Leu Arg Gly Leu Thr His Ile Pro Arg Val Asn
  1               5                  10                  15

Ser Ala Gln Gln Pro Ser Cys Ala His Ala Arg Leu Gln Phe Lys Leu
                 20                  25                  30

Arg Ser Met Gln Leu Leu Ser Glu Asp Arg Thr Asp His Met Arg Gly
             35                  40                  45

Ala Ser Thr Trp Ala Gly Gly Gln Ser Gln Asp Glu Leu Met Leu Lys
         50                  55                  60

Asp Glu Cys Ile Leu Val Asp Val Glu Asp Asn Ile Thr Gly His Ala
 65                  70                  75                  80

Ser Lys Leu Glu Cys His Lys Phe Leu Pro His Gln Pro Ala Gly Leu
                 85                  90                  95

Leu His Arg Ala Phe Ser Val Phe Leu Phe Asp Asp Gln Gly Arg Leu
            100                 105                 110

Leu Leu Gln Gln Arg Ala Arg Ser Lys Ile Thr Phe Pro Ser Val Trp
        115                 120                 125

Thr Asn Thr Cys Cys Ser His Pro Leu His Gly Gln Thr Pro Asp Glu
    130                 135                 140

Val Asp Gln Leu Ser Gln Val Ala Asp Gly Thr Val Pro Gly Ala Lys
145                 150                 155                 160

Ala Ala Ala Ile Arg Lys Leu Glu His Glu Leu Gly Ile Pro Ala His
                165                 170                 175

Gln Leu Pro Ala Ser Ala Phe Arg Phe Leu Thr Arg Leu His Tyr Cys
            180                 185                 190

Ala Ala Asp Val Gln Pro Ala Thr Gln Ser Ala Leu Trp Gly Glu
        195                 200                 205

His Glu Met Asp Tyr Ile Leu Phe Ile Arg Ala Asn Val Thr Leu Ala
    210                 215                 220

Pro Asn Pro Asp Glu Val Asp Glu Val Arg Tyr Val Thr Gln Glu Glu
225                 230                 235                 240

Leu Arg Gln Met Met Gln Pro Asp Asn Gly Leu Gln Trp Ser Pro Trp
                245                 250                 255

Phe Arg Ile Ile Ala Ala Arg Phe Leu Glu Arg Trp Trp Ala Asp Leu
            260                 265                 270

Asp Ala Ala Leu Asn Thr Asp Lys His Glu Asp Trp Gly Thr Val His
        275                 280                 285

His Ile Asn Glu Ala
    290

<210> SEQ ID NO 44
<211> LENGTH: 305
<212> TYPE: PRT
```

<213> ORGANISM: Haematococcus pluvialis

<400> SEQUENCE: 44

```
Met Leu Arg Ser Leu Leu Arg Gly Leu Thr His Ile Pro Arg Val Asn
 1               5                  10                  15

Ser Ala Gln Gln Pro Ser Cys Ala His Ala Arg Leu Gln Phe Lys Leu
            20                  25                  30

Arg Ser Met Gln Met Thr Leu Met Gln Pro Ser Ile Ser Ala Asn Leu
        35                  40                  45

Ser Arg Ala Glu Arg Thr Asp His Met Arg Gly Ala Ser Thr Trp
    50                  55                  60

Ala Gly Gly Gln Ser Gln Asp Glu Leu Met Leu Lys Asp Glu Cys Ile
65                  70                  75                  80

Leu Val Asp Val Glu Asp Asn Ile Thr Gly His Ala Ser Lys Leu Glu
                85                  90                  95

Cys His Lys Phe Leu Pro His Gln Pro Ala Gly Leu Leu His Arg Ala
            100                 105                 110

Phe Ser Val Phe Leu Phe Asp Asp Gln Gly Arg Leu Leu Leu Gln Gln
        115                 120                 125

Arg Ala Arg Ser Lys Ile Thr Phe Pro Ser Val Trp Thr Asn Thr Cys
    130                 135                 140

Cys Ser His Pro Leu His Gly Gln Thr Pro Asp Glu Val Asp Gln Leu
145                 150                 155                 160

Ser Gln Val Ala Asp Gly Thr Val Pro Gly Ala Lys Ala Ala Ile
                165                 170                 175

Arg Lys Leu Glu His Glu Leu Gly Ile Pro Ala His Gln Leu Pro Ala
            180                 185                 190

Ser Ala Phe Arg Phe Leu Thr Arg Leu His Tyr Cys Ala Ala Asp Val
        195                 200                 205

Gln Pro Ala Ala Thr Gln Ser Ala Leu Trp Gly Glu His Glu Met Asp
    210                 215                 220

Tyr Ile Leu Phe Ile Arg Ala Asn Val Thr Leu Ala Pro Asn Pro Asp
225                 230                 235                 240

Glu Val Asp Glu Val Arg Tyr Val Thr Gln Glu Glu Leu Arg Gln Met
                245                 250                 255

Met Gln Pro Asp Asn Gly Leu Gln Trp Ser Pro Trp Phe Arg Ile Ile
            260                 265                 270

Ala Ala Arg Phe Leu Glu Arg Trp Trp Ala Asp Leu Asp Ala Ala Leu
        275                 280                 285

Asn Thr Asp Lys His Glu Asp Trp Gly Thr Val His His Ile Asn Glu
    290                 295                 300

Ala
305
```

<210> SEQ ID NO 45
<211> LENGTH: 307
<212> TYPE: PRT
<213> ORGANISM: Chlamydomonas reinhardtii

<400> SEQUENCE: 45

```
Met Arg Ser Ser Phe Ile Glu Pro Lys Pro Arg Ala Gln Pro Val Leu
 1               5                  10                  15

Ser Arg Gly Arg Ala Ser Met Arg Leu Ala Gln Ser Arg Ala Leu Val
            20                  25                  30

Ala Arg Val Ser Ser Ala Leu Trp Pro Gly Ala Gly Leu Ser Gln Ala
```

```
            35                  40                  45
Gln Ser Val Ala Val Arg Met Ala Ser Ser Thr Trp Glu Gly Thr
     50                  55                  60
Gly Leu Ser Gln Asp Asp Phe Met Gln Arg Asp Glu Cys Leu Val Val
 65                  70                  75                  80
Asp Glu Gln Asp Arg Leu Leu Gly Thr Ala Asn Lys Tyr Asp Cys His
                 85                  90                  95
Arg Phe Glu Ala Ala Lys Gly Gln Pro Cys Gly Arg Leu His Arg Ala
                100                 105                 110
Phe Ser Val Phe Leu Phe Ser Pro Asp Gly Arg Leu Leu Leu Gln Gln
                115                 120                 125
Arg Ala Ala Ser Lys Val Thr Phe Pro Gly Val Trp Thr Asn Thr Cys
            130                 135                 140
Cys Ser His Pro Leu Ala Gly Gln Ala Pro Asp Glu Val Asp Leu Pro
145                 150                 155                 160
Ala Ala Val Ala Ser Gly Gln Val Pro Gly Ile Lys Ala Ala Ala Val
                165                 170                 175
Arg Lys Leu Gln His Glu Leu Gly Ile Pro Pro Glu Gln Val Pro Ala
            180                 185                 190
Ser Ser Phe Ser Phe Leu Thr Arg Leu His Tyr Cys Ala Ala Asp Thr
            195                 200                 205
Ala Thr His Gly Pro Ala Ala Glu Trp Gly Glu His Glu Val Asp Tyr
        210                 215                 220
Val Leu Phe Val Arg Pro Gln Gln Pro Val Ser Leu Gln Pro Asn Pro
225                 230                 235                 240
Asp Glu Val Asp Ala Thr Arg Tyr Val Thr Leu Pro Glu Leu Gln Ser
                245                 250                 255
Met Met Ala Asp Pro Gly Leu Ser Trp Ser Pro Trp Phe Arg Ile Leu
                260                 265                 270
Ala Thr Gln Pro Ala Phe Leu Pro Ala Trp Trp Gly Asp Leu Lys Arg
            275                 280                 285
Arg Trp Arg Pro Gly Gly Ser Arg Leu Ser Asp Trp Gly Thr Ile His
        290                 295                 300
Arg Val Met
305

<210> SEQ ID NO 46
<211> LENGTH: 1848
<212> TYPE: DNA
<213> ORGANISM: Adonis palaestina

<400> SEQUENCE: 46
gagagaaaaa gagtgttata ttaatgttac tgtcgcattc ttgcaacaca tattcagact    60
ccatttttctt gttttctctt caaaacaaca aactaatgtg acggagtatc tagctatgga   120
actacttggt gttcgcaacc tcatctcttc ttgccctgtc tggacttttg aacaagaaa    180
ccttagtagt tcaaaactag cttataacat acatcgatat ggttcttctt gtagagtaga   240
ttttcaagtg agggctgatg gtggaagcgg gagtagaact tctgttgctt ataaagaggg   300
ttttgtggac gaggaggatt ttatcaaagc tggtggttct gagcttttgt ttgtccaaat   360
gcagcaaaca aagtctatgg agaaacaggc caagctcgcc gataagttgc accaatacc    420
tttcggagaa tctgtgatgg acttggttgt aataggttgt ggacctgctg gtctttcact   480
ggctgcagaa gctgctaagc taggcttgaa agttggcctt attggtcctg atcttccttt   540
```

-continued

```
tacaaataat tatggtgtgt gggaagacga gttcaaagat cttggacttg aacgttgtat    600
cgagcatgct tggaaggaca ccatcgtata tcttgacaat gatgctcctg tccttattgg    660
tcgtgcatat ggacgagtta gccggcattt gctgcatgaa gagttgctga aaaggtgtgt    720
cgagtcaggt gtatcatatc tgaattctaa agtggaaagg atcactgaag ctggtgatgg    780
ccatagtctt gtagtttgtg aaaacgacat ctttatccct tgcaggcttg ctactgttgc    840
atctggagca gcttcaggga aacttttgga gtatgaagta ggtggccctc gtgtttgtgt    900
ccaaactgct tatggtgtgg aggttgaggt ggagaacaat ccatacgatc caacttaat    960 ggtatttatg gactacagag actatatgca acagaaatta cagtgctcgg aagaagaata   1020
tccaacattt ctctatgtca tgcccatgtc gccaacaaga cttttttttg aggaaacctg   1080
tttggcctca aaagatgcca tgcctttcga tctactgaag agaaaactaa tgtcacgatt   1140
gaagactctg ggtatccaag ttacaaaaat ttatgaagag aatggtcttt atattcctgt   1200
tgggggttct ttaccaaaca cagagcaaaa gaacctagca tttggtgctg cagcaagcat   1260
ggtgcatcca gcaacaggct attcggttgt acgatcacta tcagaagctc caaaatatgc   1320
ttctgtaatt gcaaagattt tgaagcaaga taactctgca tatgtggttt ctggacaaag   1380
cagtgcagta acatttcaa tgcaagcatg gagcagtctt tggccaaagg agcgaaaacg   1440
tcaaagagca ttctttcttt tcggttaga gcttattgtg cagctagata ttgaagcaac   1500
cagaacgttc tttagaacct tcttccgctt gccaacttgg atgtggtggg gtttccttgg   1560
gtcttcacta tcatctttcg atcttgtatt gttttccatg tacatgtttg ttttggcccc   1620
gaacagcatg aggatgtcac ttgtgagaca tttgctttca gatccttctg gtgcagttat   1680
ggttaaagct tacctcgaaa ggtaatctgt tttatgaaac tatagtgtct cattaaataa   1740
atgaggatcc ttcgtatatg tatatgatca tctctatgta tatcctatat ctaatctca   1800 taaagtaatc gaaaattcat tgatagaaaa aaaaaaaaaa aaaaaaaa               1848
```

<210> SEQ ID NO 47
<211> LENGTH: 529
<212> TYPE: PRT
<213> ORGANISM: Adonis palaestina

<400> SEQUENCE: 47

```
Met Glu Leu Leu Gly Val Arg Asn Leu Ile Ser Ser Cys Pro Val Trp
 1               5                  10                  15

Thr Phe Gly Thr Arg Asn Leu Ser Ser Ser Lys Leu Ala Tyr Asn Ile
            20                  25                  30

His Arg Tyr Gly Ser Ser Cys Arg Val Asp Phe Gln Val Arg Ala Asp
        35                  40                  45

Gly Gly Ser Gly Ser Arg Ser Ser Val Ala Tyr Lys Glu Gly Phe Val
    50                  55                  60

Asp Glu Glu Asp Phe Ile Lys Ala Gly Ser Glu Leu Leu Phe Val
 65                  70                  75                  80

Gln Met Gln Gln Thr Lys Ser Met Glu Lys Gln Ala Lys Leu Ala Asp
                85                  90                  95

Lys Leu Pro Pro Ile Pro Phe Gly Glu Ser Val Met Asp Leu Val Val
            100                 105                 110

Ile Gly Cys Gly Pro Ala Gly Leu Ser Leu Ala Ala Glu Ala Ala Lys
        115                 120                 125

Leu Gly Leu Lys Val Gly Leu Ile Gly Pro Asp Leu Pro Phe Thr Asn
    130                 135                 140
```

```
Asn Tyr Gly Val Trp Glu Asp Glu Phe Lys Asp Leu Gly Leu Glu Arg
145                 150                 155                 160

Cys Ile Glu His Ala Trp Lys Asp Thr Ile Val Tyr Leu Asp Asn Asp
            165                 170                 175

Ala Pro Val Leu Ile Gly Arg Ala Tyr Gly Arg Val Ser Arg His Leu
                180                 185                 190

Leu His Glu Glu Leu Leu Lys Arg Cys Val Glu Ser Gly Val Ser Tyr
        195                 200                 205

Leu Asp Ser Lys Val Glu Arg Ile Thr Glu Ala Gly Asp Gly His Ser
    210                 215                 220

Leu Val Val Cys Glu Asn Asp Ile Phe Ile Pro Cys Arg Leu Ala Thr
225                 230                 235                 240

Val Ala Ser Gly Ala Ala Ser Gly Lys Leu Leu Glu Tyr Glu Val Gly
                245                 250                 255

Gly Pro Arg Val Cys Val Gln Thr Ala Tyr Gly Val Glu Val Glu Val
                260                 265                 270

Glu Asn Asn Pro Tyr Asp Pro Asn Leu Met Val Phe Met Asp Tyr Arg
        275                 280                 285

Asp Tyr Met Gln Gln Lys Leu Gln Cys Ser Glu Glu Glu Tyr Pro Thr
    290                 295                 300

Phe Leu Tyr Val Met Pro Met Ser Pro Thr Arg Leu Phe Phe Glu Glu
305                 310                 315                 320

Thr Cys Leu Ala Ser Lys Asp Ala Met Pro Phe Asp Leu Leu Lys Arg
                325                 330                 335

Lys Leu Met Ser Arg Leu Lys Thr Leu Gly Ile Gln Val Thr Lys Val
                340                 345                 350

Tyr Glu Glu Glu Trp Ser Tyr Ile Pro Val Gly Gly Ser Leu Pro Asn
        355                 360                 365

Thr Glu Gln Lys Asn Leu Ala Phe Gly Ala Ala Ser Met Val His
    370                 375                 380

Pro Ala Thr Gly Tyr Ser Val Val Arg Ser Leu Ser Glu Ala Pro Lys
385                 390                 395                 400

Tyr Ala Ser Val Ile Ala Lys Ile Leu Lys Gln Asp Asn Ser Ala Tyr
                405                 410                 415

Val Val Ser Gly Gln Ser Ser Ala Val Asn Ile Ser Met Gln Ala Trp
                420                 425                 430

Ser Ser Leu Trp Pro Lys Glu Arg Lys Arg Gln Arg Ala Phe Phe Leu
            435                 440                 445

Phe Gly Leu Glu Leu Ile Val Gln Leu Asp Ile Glu Ala Thr Arg Thr
    450                 455                 460

Phe Phe Arg Thr Phe Phe Arg Leu Pro Thr Trp Met Trp Gly Phe
465                 470                 475                 480

Leu Gly Ser Ser Leu Ser Ser Phe Asp Leu Val Leu Phe Ser Met Tyr
                485                 490                 495

Met Phe Val Leu Ala Pro Asn Ser Met Arg Met Ser Leu Val Arg His
            500                 505                 510

Leu Leu Ser Asp Pro Ser Gly Ala Val Met Val Lys Ala Tyr Leu Glu
        515                 520                 525

Arg

<210> SEQ ID NO 48
<211> LENGTH: 378
<212> TYPE: PRT
<213> ORGANISM: Solanum tuberosum
```

```
<220> FEATURE:
<221> NAME/KEY: MOD_RES
<222> LOCATION: (336)
<223> OTHER INFORMATION: Any amino acid

<400> SEQUENCE: 48
```

| | | | | | | | | | | | | | | |
|---|---|---|---|---|---|---|---|---|---|---|---|---|---|---|
| Asp | Glu | Phe | Lys | Asp | Leu | Gly | Leu | Gln | Ala | Cys | Ile | Glu | His | Val | Trp |
| 1 | | | | 5 | | | | | 10 | | | | | 15 | |
| Arg | Asp | Thr | Ile | Val | Tyr | Leu | Asp | Asp | Asp | Pro | Ile | Leu | Ile | Gly |
| | | | 20 | | | | | 25 | | | | | 30 | |
| Arg | Ala | Tyr | Gly | Arg | Val | Ser | Arg | His | Leu | Leu | His | Glu | Glu | Leu | Leu |
| | | 35 | | | | | 40 | | | | | 45 | | |
| Lys | Arg | Cys | Val | Glu | Ala | Gly | Val | Leu | Tyr | Leu | Asn | Ser | Lys | Val | Asp |
| | 50 | | | | | 55 | | | | | 60 | | | |
| Arg | Ile | Val | Glu | Ala | Thr | Asn | Gly | His | Ser | Leu | Val | Glu | Cys | Glu | Gly |
| 65 | | | | | 70 | | | | | 75 | | | | | 80 |
| Asp | Val | Val | Ile | Pro | Cys | Arg | Phe | Val | Thr | Val | Ala | Ser | Gly | Ala | Ala |
| | | | | 85 | | | | | 90 | | | | | 95 | |
| Ser | Gly | Lys | Phe | Leu | Gln | Tyr | Glu | Leu | Gly | Pro | Arg | Val | Ser | Val |
| | | | 100 | | | | | 105 | | | | | 110 | |
| Gln | Thr | Ala | Tyr | Gly | Val | Glu | Val | Glu | Val | Asp | Asn | Asn | Pro | Phe | Asp |
| | | | 115 | | | | | 120 | | | | | 125 | | |
| Pro | Ser | Leu | Met | Val | Phe | Met | Asp | Tyr | Arg | Asp | Tyr | Val | Arg | His | Asp |
| | 130 | | | | | 135 | | | | | 140 | | | |
| Ala | Gln | Ser | Leu | Glu | Ala | Lys | Tyr | Pro | Thr | Phe | Leu | Tyr | Ala | Met | Pro |
| 145 | | | | | 150 | | | | | 155 | | | | | 160 |
| Met | Ser | Pro | Thr | Arg | Val | Phe | Phe | Glu | Glu | Thr | Cys | Leu | Ala | Ser | Lys |
| | | | | 165 | | | | | 170 | | | | | 175 | |
| Asp | Ala | Met | Pro | Phe | Asp | Leu | Leu | Lys | Lys | Leu | Met | Leu | Arg | Leu |
| | | | 180 | | | | | 185 | | | | | 190 | | |
| Asn | Thr | Leu | Gly | Val | Arg | Ile | Lys | Glu | Ile | Tyr | Glu | Glu | Trp | Ser |
| | | | 195 | | | | | 200 | | | | | 205 | | |
| Tyr | Ile | Pro | Val | Gly | Gly | Ser | Leu | Pro | Asn | Thr | Glu | Gln | Lys | Thr | Leu |
| | | 210 | | | | | 215 | | | | | 220 | | | |
| Ala | Phe | Gly | Ala | Ala | Ala | Ser | Met | Val | His | Pro | Ala | Thr | Gly | Tyr | Ser |
| 225 | | | | | 230 | | | | | 235 | | | | | 240 |
| Val | Val | Arg | Ser | Leu | Ser | Glu | Ala | Pro | Lys | Cys | Ala | Phe | Val | Leu | Ala |
| | | | | 245 | | | | | 250 | | | | | 255 | |
| Asn | Ile | Leu | Arg | Gln | Asn | His | Ser | Lys | Asn | Met | Leu | Thr | Ser | Ser | Ser |
| | | | 260 | | | | | 265 | | | | | 270 | | |
| Thr | Pro | Ser | Ile | Ser | Thr | Gln | Ala | Trp | Asn | Thr | Leu | Trp | Pro | Gln | Glu |
| | | | 275 | | | | | 280 | | | | | 285 | | |
| Arg | Lys | Arg | Gln | Arg | Ser | Phe | Phe | Leu | Phe | Gly | Leu | Ala | Leu | Ile | Leu |
| | | 290 | | | | | 295 | | | | | 300 | | | |
| Gln | Leu | Asp | Ile | Glu | Gly | Ile | Arg | Ser | Phe | Arg | Ala | Phe | Phe | Arg |
| 305 | | | | | 310 | | | | | 315 | | | | | 320 |
| Val | Pro | Lys | Trp | Met | Trp | Gln | Gly | Phe | Leu | Gly | Ser | Ser | Leu | Ser | Xaa |
| | | | | 325 | | | | | 330 | | | | | 335 | |
| Ala | Asp | Leu | Met | Leu | Phe | Ala | Phe | Tyr | Met | Phe | Ile | Ile | Ala | Pro | Asn |
| | | | 340 | | | | | 345 | | | | | 350 | | |
| Asp | Met | Arg | Arg | Gly | Leu | Ile | Arg | His | Leu | Leu | Ser | Asp | Pro | Thr | Gly |
| | | | 355 | | | | | 360 | | | | | 365 | | |
| Ala | Thr | Leu | Ile | Arg | Thr | Tyr | Leu | Thr | Phe |
| | | 370 | | | | | 375 | | |

```
<210> SEQ ID NO 49
<211> LENGTH: 524
<212> TYPE: PRT
<213> ORGANISM: Arabidopsis thaliana

<400> SEQUENCE: 49
```

| | | | | | | | | | | | | | | |
|---|---|---|---|---|---|---|---|---|---|---|---|---|---|---|
| Met | Glu | Cys | Val | Gly | Ala | Arg | Asn | Phe | Ala | Ala | Met | Ala | Val | Ser | Thr |
| 1 | | | | 5 | | | | | 10 | | | | | 15 | |
| Phe | Pro | Ser | Trp | Ser | Cys | Arg | Arg | Lys | Phe | Pro | Val | Val | Lys | Arg | Tyr |
| | | | 20 | | | | | 25 | | | | | 30 | | |
| Ser | Tyr | Arg | Asn | Ile | Arg | Phe | Gly | Leu | Cys | Ser | Val | Arg | Ala | Ser | Gly |
| | | 35 | | | | | 40 | | | | | 45 | | | |
| Gly | Gly | Ser | Ser | Gly | Ser | Glu | Ser | Cys | Val | Ala | Val | Arg | Glu | Asp | Phe |
| | 50 | | | | | 55 | | | | | 60 | | | | |
| Ala | Asp | Glu | Glu | Asp | Phe | Val | Lys | Ala | Gly | Gly | Ser | Glu | Ile | Leu | Phe |
| 65 | | | | | 70 | | | | | 75 | | | | | 80 |
| Val | Gln | Met | Gln | Gln | Asn | Lys | Asp | Met | Asp | Glu | Gln | Ser | Lys | Leu | Val |
| | | | | 85 | | | | | 90 | | | | | 95 | |
| Asp | Lys | Leu | Pro | Pro | Ile | Ser | Ile | Gly | Asp | Gly | Ala | Leu | Asp | His | Val |
| | | | | 100 | | | | | 105 | | | | | 110 | |
| Val | Ile | Gly | Cys | Gly | Pro | Ala | Gly | Leu | Ala | Leu | Ala | Ala | Glu | Ser | Ala |
| | | | | 115 | | | | | 120 | | | | | 125 | |
| Lys | Leu | Gly | Leu | Lys | Val | Gly | Leu | Ile | Gly | Pro | Asp | Leu | Pro | Phe | Thr |
| | 130 | | | | | 135 | | | | | 140 | | | | |
| Asn | Asn | Tyr | Gly | Val | Trp | Glu | Asp | Glu | Phe | Asn | Asp | Leu | Gly | Leu | Gln |
| 145 | | | | | 150 | | | | | 155 | | | | | 160 |
| Lys | Cys | Ile | Glu | His | Val | Trp | Arg | Glu | Thr | Ile | Val | Tyr | Leu | Asp | Asp |
| | | | | 165 | | | | | 170 | | | | | 175 | |
| Asp | Lys | Pro | Ile | Thr | Ile | Gly | Arg | Ala | Tyr | Gly | Arg | Val | Ser | Arg | Arg |
| | | | 180 | | | | | 185 | | | | | 190 | | |
| Leu | Leu | His | Glu | Glu | Leu | Leu | Arg | Arg | Cys | Val | Glu | Ser | Gly | Val | Ser |
| | | | 195 | | | | | 200 | | | | | 205 | | |
| Tyr | Leu | Ser | Ser | Lys | Val | Asp | Ser | Ile | Thr | Glu | Ala | Ser | Asp | Gly | Leu |
| | 210 | | | | | 215 | | | | | 220 | | | | |
| Arg | Leu | Val | Ala | Cys | Asp | Asp | Asn | Asn | Val | Ile | Pro | Cys | Arg | Leu | Ala |
| 225 | | | | | 230 | | | | | 235 | | | | | 240 |
| Thr | Val | Ala | Ser | Gly | Ala | Ala | Ser | Gly | Lys | Leu | Leu | Gln | Tyr | Glu | Val |
| | | | | 245 | | | | | 250 | | | | | 255 | |
| Gly | Gly | Pro | Arg | Val | Cys | Val | Gln | Thr | Ala | Tyr | Gly | Val | Glu | Val | Glu |
| | | | 260 | | | | | 265 | | | | | 270 | | |
| Val | Glu | Asn | Ser | Pro | Tyr | Asp | Pro | Asp | Gln | Met | Val | Phe | Met | Asp | Tyr |
| | | | 275 | | | | | 280 | | | | | 285 | | |
| Arg | Asp | Tyr | Thr | Asn | Glu | Lys | Val | Arg | Ser | Leu | Glu | Ala | Glu | Tyr | Pro |
| | 290 | | | | | 295 | | | | | 300 | | | | |
| Thr | Phe | Leu | Tyr | Ala | Met | Pro | Met | Thr | Lys | Ser | Arg | Leu | Phe | Phe | Glu |
| 305 | | | | | 310 | | | | | 315 | | | | | 320 |
| Glu | Thr | Cys | Leu | Ala | Ser | Lys | Asp | Val | Met | Pro | Phe | Asp | Leu | Leu | Lys |
| | | | | 325 | | | | | 330 | | | | | 335 | |
| Thr | Lys | Leu | Met | Leu | Arg | Leu | Asp | Thr | Leu | Gly | Ile | Arg | Ile | Leu | Lys |
| | | | 340 | | | | | 345 | | | | | 350 | | |
| Thr | Tyr | Glu | Glu | Glu | Trp | Ser | Tyr | Ile | Pro | Val | Gly | Gly | Ser | Leu | Pro |
| | | | 355 | | | | | 360 | | | | | 365 | | |
| Asn | Thr | Glu | Gln | Lys | Asn | Leu | Ala | Phe | Gly | Ala | Ala | Ala | Ser | Met | Val |
| 370 | | | | | 375 | | | | | 380 | | | | | |

-continued

```
His Pro Ala Thr Gly Tyr Ser Val Val Arg Ser Leu Ser Glu Ala Pro
385                 390                 395                 400

Lys Tyr Ala Ser Val Ile Ala Glu Ile Leu Arg Glu Thr Thr Lys
                405                 410                 415

Gln Ile Asn Ser Asn Ile Ser Arg Gln Ala Trp Asp Thr Leu Trp Pro
                420                 425                 430

Pro Glu Arg Lys Arg Gln Arg Ala Phe Phe Leu Phe Gly Leu Ala Leu
            435                 440                 445

Ile Val Gln Phe Asp Thr Glu Gly Ile Arg Ser Phe Phe Arg Thr Phe
        450                 455                 460

Phe Arg Leu Pro Lys Trp Met Trp Gln Gly Phe Leu Gly Ser Thr Leu
465                 470                 475                 480

Thr Ser Gly Asp Leu Val Leu Phe Ala Leu Tyr Met Phe Val Ile Ser
                485                 490                 495

Pro Asn Asn Leu Arg Lys Gly Leu Ile Asn His Leu Ile Ser Asp Pro
                500                 505                 510

Thr Gly Ala Thr Met Ile Lys Thr Tyr Leu Lys Val
            515                 520

<210> SEQ ID NO 50
<211> LENGTH: 529
<212> TYPE: PRT
<213> ORGANISM: Adonis palaestina

<400> SEQUENCE: 50

Met Glu Leu Leu Gly Val Arg Asn Leu Ile Ser Ser Cys Pro Val Trp
 1               5                  10                  15

Thr Phe Gly Thr Arg Asn Leu Ser Ser Ser Lys Leu Ala Tyr Asn Ile
                20                  25                  30

His Arg Tyr Gly Ser Ser Cys Arg Val Asp Phe Gln Val Arg Ala Asp
            35                  40                  45

Gly Gly Ser Gly Ser Arg Ser Ser Val Ala Tyr Lys Glu Gly Phe Val
    50                  55                  60

Asp Glu Glu Asp Phe Ile Lys Ala Gly Gly Ser Glu Leu Leu Phe Val
65                  70                  75                  80

Gln Met Gln Gln Thr Lys Ser Met Glu Lys Gln Ala Lys Leu Ala Asp
                85                  90                  95

Lys Leu Pro Pro Ile Pro Phe Gly Glu Ser Val Met Asp Leu Val Val
                100                 105                 110

Ile Gly Cys Gly Pro Ala Gly Leu Ser Leu Ala Ala Glu Ala Ala Lys
            115                 120                 125

Leu Gly Leu Lys Val Gly Leu Ile Gly Pro Asp Leu Pro Phe Thr Asn
130                 135                 140

Asn Tyr Gly Val Trp Glu Asp Glu Phe Lys Asp Leu Gly Leu Glu Arg
145                 150                 155                 160

Cys Ile Glu His Ala Trp Lys Asp Thr Ile Val Tyr Leu Asp Asn Asp
                165                 170                 175

Ala Pro Val Leu Ile Gly Arg Ala Tyr Gly Arg Val Ser Arg His Leu
                180                 185                 190

Leu His Glu Glu Leu Leu Lys Arg Cys Val Glu Ser Gly Val Ser Tyr
            195                 200                 205

Leu Asp Ser Lys Val Glu Arg Ile Thr Glu Ala Gly Asp Gly His Ser
    210                 215                 220

Leu Val Val Cys Glu Asn Glu Ile Phe Ile Pro Cys Arg Leu Ala Thr
```

```
               225                 230                 235                 240
Val Ala Ser Gly Ala Ala Ser Gly Lys Leu Leu Glu Tyr Glu Val Gly
                245                 250                 255

Gly Pro Arg Val Cys Val Gln Thr Ala Tyr Gly Val Glu Val Glu Val
                260                 265                 270

Glu Asn Asn Pro Tyr Asp Pro Asn Leu Met Val Phe Met Asp Tyr Arg
                275                 280                 285

Asp Tyr Met Gln Gln Lys Leu Gln Cys Ser Glu Glu Tyr Pro Thr
            290                 295                 300

Phe Leu Tyr Val Met Pro Met Ser Pro Thr Arg Leu Phe Phe Glu Glu
305                 310                 315                 320

Thr Cys Leu Ala Ser Lys Asp Ala Met Pro Phe Asp Leu Leu Lys Arg
                325                 330                 335

Lys Leu Met Ser Arg Leu Lys Thr Leu Gly Ile Gln Val Thr Lys Val
                340                 345                 350

Tyr Glu Glu Glu Trp Ser Tyr Ile Pro Val Gly Gly Ser Leu Pro Asn
                355                 360                 365

Thr Glu Gln Lys Asn Leu Ala Phe Gly Ala Ala Ser Met Val His
    370                 375                 380

Pro Ala Thr Gly Tyr Ser Val Val Arg Ser Leu Ser Glu Ala Pro Lys
385                 390                 395                 400

Tyr Ala Ser Val Ile Ala Lys Ile Leu Lys Gln Asp Asn Ser Ala Tyr
                405                 410                 415

Val Val Ser Gly Gln Ser Ser Ala Val Asn Ile Ser Met Gln Ala Trp
                420                 425                 430

Ser Ser Leu Trp Pro Lys Glu Arg Lys Arg Gln Arg Ala Phe Phe Leu
                435                 440                 445

Phe Gly Leu Glu Leu Ile Val Gln Leu Asp Ile Glu Ala Thr Arg Thr
                450                 455                 460

Phe Phe Arg Thr Phe Phe Arg Leu Pro Thr Trp Met Trp Gly Phe
465                 470                 475                 480

Leu Gly Ser Ser Leu Ser Ser Phe Asp Leu Val Leu Phe Ser Met Tyr
                485                 490                 495

Met Phe Val Leu Ala Pro Asn Ser Met Arg Met Ser Leu Val Arg His
                500                 505                 510

Leu Leu Ser Asp Pro Ser Gly Ala Val Met Val Arg Ala Tyr Leu Glu
            515                 520                 525

Arg

<210> SEQ ID NO 51
<211> LENGTH: 529
<212> TYPE: PRT
<213> ORGANISM: Adonis palaestina

<400> SEQUENCE: 51

Met Glu Leu Leu Gly Val Arg Asn Leu Ile Ser Ser Cys Pro Val Trp
  1               5                  10                  15

Thr Phe Gly Thr Arg Asn Leu Ser Ser Ser Lys Leu Ala Tyr Asn Ile
                20                  25                  30

His Arg Tyr Gly Ser Ser Cys Arg Val Asp Phe Gln Val Arg Ala Asp
            35                  40                  45

Gly Gly Ser Gly Ser Arg Thr Ser Val Ala Tyr Lys Glu Gly Phe Val
    50                  55                  60

Asp Glu Glu Asp Phe Ile Lys Ala Gly Gly Ser Glu Leu Leu Phe Val
```

-continued

```
             65                  70                  75                  80
    Gln Met Gln Gln Thr Lys Ser Met Glu Lys Gln Ala Lys Leu Ala Asp
                         85                  90                  95
    Lys Leu Pro Pro Ile Pro Phe Gly Glu Ser Val Met Asp Leu Val Val
                    100                 105                 110
    Ile Gly Cys Gly Pro Ala Gly Leu Ser Leu Ala Ala Glu Ala Ala Lys
                115                 120                 125
    Leu Gly Leu Lys Val Gly Leu Ile Gly Pro Asp Leu Pro Phe Thr Asn
    130                 135                 140
    Asn Tyr Gly Val Trp Glu Asp Glu Phe Lys Asp Leu Gly Leu Glu Arg
    145                 150                 155                 160
    Cys Ile Glu His Ala Trp Lys Asp Thr Ile Val Tyr Leu Asp Asn Asp
                    165                 170                 175
    Ala Pro Val Leu Ile Gly Arg Ala Tyr Gly Arg Val Ser Arg His Leu
                180                 185                 190
    Leu His Glu Glu Leu Leu Lys Arg Cys Val Glu Ser Gly Val Ser Tyr
                195                 200                 205
    Leu Asn Ser Lys Val Glu Arg Ile Thr Glu Ala Gly Asp Gly His Ser
    210                 215                 220
    Leu Val Val Cys Glu Asn Asp Ile Phe Ile Pro Cys Arg Leu Ala Thr
    225                 230                 235                 240
    Val Ala Ser Gly Ala Ala Ser Gly Lys Leu Leu Glu Tyr Glu Val Gly
                    245                 250                 255
    Gly Pro Arg Val Cys Val Gln Thr Ala Tyr Gly Val Glu Val Glu Val
                260                 265                 270
    Glu Asn Asn Pro Tyr Asp Pro Asn Leu Met Val Phe Met Asp Tyr Arg
                275                 280                 285
    Asp Tyr Met Gln Gln Lys Leu Gln Cys Ser Glu Glu Tyr Pro Thr
    290                 295                 300
    Phe Leu Tyr Val Met Pro Met Ser Pro Thr Arg Leu Phe Phe Glu Glu
    305                 310                 315                 320
    Thr Cys Leu Ala Ser Lys Asp Ala Met Pro Phe Asp Leu Leu Lys Arg
                    325                 330                 335
    Lys Leu Met Ser Arg Leu Lys Thr Leu Gly Ile Gln Val Thr Lys Ile
                340                 345                 350
    Tyr Glu Glu Glu Trp Ser Tyr Ile Pro Val Gly Gly Ser Leu Pro Asn
                355                 360                 365
    Thr Glu Gln Lys Asn Leu Ala Phe Gly Ala Ala Ser Met Val His
    370                 375                 380
    Pro Ala Thr Gly Tyr Ser Val Val Arg Ser Leu Ser Glu Ala Pro Lys
    385                 390                 395                 400
    Tyr Ala Ser Val Ile Ala Lys Ile Leu Lys Gln Asp Asn Ser Ala Tyr
                    405                 410                 415
    Val Val Ser Gly Gln Ser Ser Ala Val Asn Ile Ser Met Gln Ala Trp
                420                 425                 430
    Ser Ser Leu Trp Pro Lys Glu Arg Lys Arg Gln Arg Ala Phe Phe Leu
                435                 440                 445
    Phe Gly Leu Glu Leu Ile Val Gln Leu Asp Ile Glu Ala Thr Arg Thr
                450                 455                 460
    Phe Phe Arg Thr Phe Phe Arg Leu Pro Thr Trp Met Trp Trp Gly Phe
    465                 470                 475                 480
    Leu Gly Ser Ser Leu Ser Ser Phe Asp Leu Val Leu Phe Ser Met Tyr
                    485                 490                 495
```

Met Phe Val Leu Ala Pro Asn Ser Met Arg Met Ser Leu Val Arg His
                500                 505                 510

Leu Leu Ser Asp Pro Ser Gly Ala Val Met Val Lys Ala Tyr Leu Glu
            515                 520                 525

Arg

<210> SEQ ID NO 52
<211> LENGTH: 533
<212> TYPE: PRT
<213> ORGANISM: Lactuca sp.

<400> SEQUENCE: 52

Met Glu Cys Phe Gly Ala Arg Asn Met Thr Ala Thr Met Ala Val Phe
  1               5                  10                  15

Thr Cys Pro Arg Phe Thr Asp Cys Asn Ile Arg His Lys Phe Ser Leu
             20                  25                  30

Leu Lys Gln Arg Arg Phe Thr Asn Leu Ser Ala Ser Ser Ser Leu Arg
         35                  40                  45

Gln Ile Lys Cys Ser Ala Lys Ser Asp Arg Cys Val Val Asp Lys Gln
     50                  55                  60

Gly Ile Ser Val Ala Asp Glu Glu Asp Tyr Val Lys Ala Gly Gly Ser
 65                  70                  75                  80

Glu Leu Phe Phe Val Gln Met Gln Arg Thr Lys Ser Met Glu Ser Gln
                 85                  90                  95

Ser Lys Leu Ser Glu Lys Leu Ala Gln Ile Pro Ile Gly Asn Cys Ile
            100                 105                 110

Leu Asp Leu Val Val Ile Gly Cys Gly Pro Ala Gly Leu Ala Leu Ala
        115                 120                 125

Ala Glu Ser Ala Lys Leu Gly Leu Asn Val Gly Leu Ile Gly Pro Asp
    130                 135                 140

Leu Pro Phe Thr Asn Asn Tyr Gly Val Trp Gln Asp Glu Phe Ile Gly
145                 150                 155                 160

Leu Gly Leu Glu Gly Cys Ile Glu His Ser Trp Lys Asp Thr Leu Val
                165                 170                 175

Tyr Leu Asp Asp Ala Asp Pro Ile Arg Ile Gly Arg Ala Tyr Gly Arg
            180                 185                 190

Val His Arg Asp Leu Leu His Glu Glu Leu Leu Arg Arg Cys Val Glu
        195                 200                 205

Ser Gly Val Ser Tyr Leu Ser Ser Lys Val Glu Arg Ile Thr Glu Ala
    210                 215                 220

Pro Asn Gly Tyr Ser Leu Ile Glu Cys Glu Gly Asn Ile Thr Ile Pro
225                 230                 235                 240

Cys Arg Leu Ala Thr Val Ala Ser Gly Ala Ala Ser Gly Lys Phe Leu
                245                 250                 255

Glu Tyr Glu Leu Gly Gly Pro Arg Val Cys Val Gln Thr Ala Tyr Gly
            260                 265                 270

Ile Glu Val Glu Val Glu Asn Asn Pro Tyr Asp Pro Asp Leu Met Val
        275                 280                 285

Phe Met Asp Tyr Arg Asp Phe Ser Lys His Lys Pro Glu Ser Leu Glu
    290                 295                 300

Ala Lys Tyr Pro Thr Phe Leu Tyr Val Met Ala Met Ser Pro Thr Lys
305                 310                 315                 320

Ile Phe Phe Glu Glu Thr Cys Leu Ala Ser Arg Glu Ala Met Pro Phe
                325                 330                 335

```
Asn Leu Leu Lys Ser Lys Leu Met Ser Arg Leu Lys Ala Met Gly Ile
                340                 345                 350

Arg Ile Thr Arg Thr Tyr Glu Glu Trp Ser Tyr Ile Pro Val Gly
            355                 360                 365

Gly Ser Leu Pro Asn Thr Glu Gln Lys Asn Leu Ala Phe Gly Ala Ala
    370                 375                 380

Ala Ser Met Val His Pro Ala Thr Gly Tyr Ser Val Val Arg Ser Leu
385                 390                 395                 400

Ser Glu Ala Pro Asn Tyr Ala Ala Val Ile Ala Lys Ile Leu Arg Gln
                405                 410                 415

Asp Gln Ser Lys Glu Met Ile Ser Leu Gly Lys Tyr Thr Asn Ile Ser
            420                 425                 430

Lys Gln Ala Trp Glu Thr Leu Trp Pro Leu Glu Arg Lys Arg Gln Arg
            435                 440                 445

Ala Phe Phe Leu Phe Gly Leu Ser His Ile Val Leu Met Asp Leu Glu
            450                 455                 460

Gly Thr Arg Thr Phe Phe Arg Thr Phe Arg Leu Pro Lys Trp Met
465                 470                 475                 480

Trp Trp Gly Phe Leu Gly Ser Ser Leu Ser Ser Thr Asp Leu Ile Ile
                485                 490                 495

Phe Ala Leu Tyr Met Phe Val Ile Ala Pro His Ser Leu Arg Met Glu
                500                 505                 510

Leu Val Arg His Leu Leu Ser Asp Pro Thr Gly Ala Thr Met Val Lys
            515                 520                 525

Ala Tyr Leu Thr Ile
        530

<210> SEQ ID NO 53
<211> LENGTH: 526
<212> TYPE: PRT
<213> ORGANISM: Lycopersicon esculentum

<400> SEQUENCE: 53

Met Glu Cys Val Gly Val Gln Asn Val Gly Ala Met Ala Val Leu Thr
1               5                   10                  15

Arg Pro Arg Leu Asn Arg Trp Ser Gly Gly Glu Leu Cys Gln Glu Lys
            20                  25                  30

Ser Ile Phe Leu Ala Tyr Glu Gln Tyr Glu Ser Lys Cys Asn Ser Ser
        35                  40                  45

Ser Gly Ser Asp Ser Cys Val Val Asp Lys Glu Asp Phe Ala Asp Glu
    50                  55                  60

Glu Asp Tyr Ile Lys Ala Gly Gly Ser Gln Leu Val Phe Val Gln Met
65                  70                  75                  80

Gln Gln Lys Lys Asp Met Asp Gln Gln Ser Lys Leu Ser Asp Glu Leu
                85                  90                  95

Arg Gln Ile Ser Ala Gly Gln Thr Val Leu Asp Leu Val Ile Gly
            100                 105                 110

Cys Gly Pro Ala Gly Leu Ala Leu Ala Ala Glu Ser Ala Lys Leu Gly
            115                 120                 125

Leu Asn Val Gly Leu Val Gly Pro Asp Leu Pro Phe Thr Asn Asn Tyr
    130                 135                 140

Gly Val Trp Glu Asp Glu Phe Lys Asp Leu Gly Leu Gln Ala Cys Ile
145                 150                 155                 160

Glu His Val Trp Arg Asp Thr Ile Val Tyr Leu Asp Asp Asp Glu Pro
```

```
                    165                 170                 175
Ile Leu Ile Gly Arg Ala Tyr Gly Arg Val Ser Arg His Phe Leu His
                180                 185                 190

Glu Glu Leu Leu Lys Arg Cys Val Glu Ala Gly Val Leu Tyr Leu Asn
            195                 200                 205

Ser Lys Val Asp Arg Ile Val Glu Ala Thr Asn Gly Gln Ser Leu Val
        210                 215                 220

Glu Cys Glu Gly Asp Val Val Ile Pro Cys Arg Phe Val Thr Val Ala
225                 230                 235                 240

Ser Gly Ala Ala Ser Gly Lys Phe Leu Gln Tyr Glu Leu Gly Ser Pro
                245                 250                 255

Arg Val Ser Val Gln Thr Ala Tyr Gly Val Glu Val Glu Val Asp Asn
            260                 265                 270

Asn Pro Phe Asp Pro Ser Leu Met Val Phe Met Asp Tyr Arg Asp Tyr
        275                 280                 285

Leu Arg His Asp Ala Gln Ser Leu Glu Ala Lys Tyr Pro Thr Phe Leu
        290                 295                 300

Tyr Ala Met Pro Met Ser Pro Thr Arg Val Phe Phe Glu Glu Thr Cys
305                 310                 315                 320

Leu Ala Ser Lys Asp Ala Met Pro Phe Asp Leu Leu Lys Lys Lys Leu
                325                 330                 335

Met Leu Arg Leu Asn Thr Leu Gly Val Arg Ile Lys Glu Ile Tyr Glu
            340                 345                 350

Glu Glu Trp Ser Tyr Ile Pro Val Gly Gly Ser Leu Pro Asn Thr Glu
        355                 360                 365

Gln Lys Thr Leu Ala Phe Gly Ala Ala Ser Met Val His Pro Ala
        370                 375                 380

Thr Gly Tyr Ser Val Val Arg Ser Leu Ser Glu Ala Pro Lys Cys Ala
385                 390                 395                 400

Ser Val Leu Ala Asn Ile Leu Arg Gln His Tyr Ser Lys Asn Met Leu
                405                 410                 415

Thr Ser Ser Ser Ile Pro Ser Ile Ser Thr Gln Ala Trp Asn Thr Leu
            420                 425                 430

Trp Pro Gln Glu Arg Lys Arg Gln Arg Ser Phe Phe Leu Phe Gly Leu
        435                 440                 445

Ala Leu Ile Leu Gln Leu Asp Ile Glu Gly Ile Arg Ser Phe Phe Arg
450                 455                 460

Ala Phe Phe Arg Val Pro Lys Trp Met Trp Gln Gly Phe Leu Gly Ser
465                 470                 475                 480

Ser Leu Ser Ser Ala Asp Leu Met Leu Phe Ala Phe Tyr Met Phe Ile
                485                 490                 495

Ile Ala Pro Asn Asp Met Arg Lys Gly Leu Ile Arg His Leu Leu Ser
            500                 505                 510

Asp Pro Thr Gly Ala Thr Leu Ile Arg Thr Tyr Leu Thr Phe
        515                 520                 525

<210> SEQ ID NO 54
<211> LENGTH: 516
<212> TYPE: PRT
<213> ORGANISM: Tagetes erecta

<400> SEQUENCE: 54

Met Ser Met Arg Ala Gly His Met Thr Ala Thr Met Ala Ala Phe Thr
  1               5                  10                  15

Cys Pro Arg Phe Met Thr Ser Ile Arg Tyr Thr Lys Gln Ile Lys Cys
```

-continued

```
            20                  25                  30
Asn Ala Ala Lys Ser Gln Leu Val Lys Gln Glu Ile Glu Glu Glu
             35                  40                  45
Glu Asp Tyr Val Lys Ala Gly Gly Ser Glu Leu Leu Phe Val Gln Met
 50                  55                  60
Gln Gln Asn Lys Ser Met Asp Ala Gln Ser Ser Leu Ser Gln Lys Leu
 65                  70                  75                  80
Pro Arg Val Pro Ile Gly Gly Gly Asp Ser Asn Cys Ile Leu Asp
                 85                  90                  95
Leu Val Val Ile Gly Cys Gly Pro Ala Gly Leu Ala Leu Ala Gly Glu
                100                 105                 110
Ser Ala Lys Leu Gly Leu Asn Val Ala Leu Ile Gly Pro Asp Leu Pro
                115                 120                 125
Phe Thr Asn Asn Tyr Gly Val Trp Glu Asp Glu Phe Ile Gly Leu Gly
 130                 135                 140
Leu Glu Gly Cys Ile Glu His Val Trp Arg Asp Thr Val Val Tyr Leu
 145                 150                 155                 160
Asp Asp Asn Asp Pro Ile Leu Ile Gly Arg Ala Tyr Gly Arg Val Ser
                165                 170                 175
Arg Asp Leu Leu His Glu Glu Leu Leu Thr Arg Cys Met Glu Ser Gly
                180                 185                 190
Val Ser Tyr Leu Ser Ser Lys Val Glu Arg Ile Thr Glu Ala Pro Asn
                195                 200                 205
Gly Leu Ser Leu Ile Glu Cys Glu Gly Asn Ile Thr Ile Pro Cys Arg
                210                 215                 220
Leu Ala Thr Val Ala Ser Gly Ala Ala Ser Gly Lys Leu Leu Gln Tyr
 225                 230                 235                 240
Glu Leu Gly Gly Pro Arg Val Cys Val Gln Thr Ala Tyr Gly Ile Glu
                245                 250                 255
Val Glu Val Glu Ser Ile Pro Tyr Asp Pro Ser Leu Met Val Phe Met
                260                 265                 270
Asp Tyr Arg Asp Tyr Thr Lys His Lys Ser Gln Ser Leu Glu Ala Gln
                275                 280                 285
Tyr Pro Thr Phe Leu Tyr Val Met Pro Met Ser Pro Thr Lys Val Phe
 290                 295                 300
Phe Glu Glu Thr Cys Leu Ala Ser Lys Glu Ala Met Pro Phe Glu Leu
 305                 310                 315                 320
Leu Lys Thr Lys Leu Met Ser Arg Leu Lys Thr Met Gly Ile Arg Ile
                325                 330                 335
Thr Lys Thr Tyr Glu Glu Glu Trp Ser Tyr Ile Pro Val Gly Gly Ser
                340                 345                 350
Leu Pro Asn Thr Glu Gln Lys Asn Leu Ala Phe Gly Ala Ala Ala Ser
                355                 360                 365
Met Val His Pro Ala Thr Gly Tyr Ser Val Val Arg Ser Leu Ser Glu
 370                 375                 380
Ala Pro Asn Tyr Ala Ala Val Ile Ala Lys Ile Leu Gly Lys Gly Asn
 385                 390                 395                 400
Ser Lys Gln Met Leu Asp His Gly Arg Tyr Thr Thr Asn Ile Ser Lys
                405                 410                 415
Gln Ala Trp Glu Thr Leu Trp Pro Leu Glu Arg Lys Arg Gln Arg Ala
                420                 425                 430
Phe Phe Leu Phe Gly Leu Ala Leu Ile Val Gln Met Asp Ile Glu Gly
 435                 440                 445
```

```
Thr Arg Thr Phe Phe Arg Thr Phe Phe Arg Leu Pro Thr Trp Met Trp
    450                 455                 460

Trp Gly Phe Leu Gly Ser Ser Leu Ser Ser Thr Asp Leu Ile Ile Phe
465                 470                 475                 480

Ala Phe Tyr Met Phe Ile Ile Ala Pro His Ser Leu Arg Met Gly Leu
                485                 490                 495

Val Arg His Leu Leu Ser Asp Pro Thr Gly Gly Thr Met Leu Lys Ala
            500                 505                 510

Tyr Leu Thr Ile
        515

<210> SEQ ID NO 55
<211> LENGTH: 501
<212> TYPE: PRT
<213> ORGANISM: Arabidopsis thaliana

<400> SEQUENCE: 55

Met Asp Thr Leu Leu Lys Thr Pro Asn Lys Leu Asp Phe Phe Ile Pro
 1               5                  10                  15

Gln Phe His Gly Phe Glu Arg Leu Cys Ser Asn Asn Pro Tyr His Ser
                20                  25                  30

Arg Val Arg Leu Gly Val Lys Lys Arg Ala Ile Lys Ile Val Ser Ser
            35                  40                  45

Val Val Ser Gly Ser Ala Ala Leu Leu Asp Leu Val Pro Glu Thr Lys
    50                  55                  60

Lys Glu Asn Leu Asp Phe Glu Leu Pro Leu Tyr Asp Thr Ser Lys Ser
65                  70                  75                  80

Gln Val Val Asp Leu Ala Ile Val Gly Gly Pro Ala Gly Leu Ala
                85                  90                  95

Val Ala Gln Gln Val Ser Glu Ala Gly Leu Ser Val Cys Ser Ile Asp
                100                 105                 110

Pro Ser Pro Lys Leu Ile Trp Pro Asn Asn Tyr Gly Val Trp Val Asp
            115                 120                 125

Glu Phe Glu Ala Met Asp Leu Leu Asp Cys Leu Asp Thr Thr Trp Ser
        130                 135                 140

Gly Ala Val Val Tyr Val Asp Glu Gly Val Lys Lys Asp Leu Ser Arg
145                 150                 155                 160

Pro Tyr Gly Arg Val Asn Arg Lys Gln Leu Lys Ser Lys Met Leu Gln
                165                 170                 175

Lys Cys Ile Thr Asn Gly Val Lys Phe His Gln Ser Lys Val Thr Asn
            180                 185                 190

Val Val His Glu Glu Ala Asn Ser Thr Val Val Cys Ser Asp Gly Val
        195                 200                 205

Lys Ile Gln Ala Ser Val Val Leu Asp Ala Thr Gly Phe Ser Arg Cys
    210                 215                 220

Leu Val Gln Tyr Asp Lys Pro Tyr Asn Pro Gly Tyr Gln Val Ala Tyr
225                 230                 235                 240

Gly Ile Val Ala Glu Val Asp Gly His Pro Phe Asp Val Asp Lys Met
                245                 250                 255

Val Phe Met Asp Trp Arg Asp Lys His Leu Asp Ser Tyr Pro Glu Leu
            260                 265                 270

Lys Glu Arg Asn Ser Lys Ile Pro Thr Phe Leu Tyr Ala Met Pro Phe
        275                 280                 285

Ser Ser Asn Arg Ile Phe Leu Glu Glu Thr Ser Leu Val Ala Arg Pro
```

-continued

```
                290                 295                 300
Gly Leu Arg Met Glu Asp Ile Gln Glu Arg Met Ala Ala Arg Leu Lys
305                 310                 315                 320

His Leu Gly Ile Asn Val Lys Arg Ile Glu Glu Asp Glu Arg Cys Val
                325                 330                 335

Ile Pro Met Gly Gly Pro Leu Pro Val Leu Pro Gln Arg Val Val Gly
                340                 345                 350

Ile Gly Gly Thr Ala Gly Met Val His Pro Ser Thr Gly Tyr Met Val
                355                 360                 365

Ala Arg Thr Leu Ala Ala Pro Ile Val Ala Asn Ala Ile Val Arg
                370                 375                 380

Tyr Leu Gly Ser Pro Ser Ser Asn Ser Leu Arg Gly Asp Gln Leu Ser
385                 390                 395                 400

Ala Glu Val Trp Arg Asp Leu Trp Pro Ile Glu Arg Arg Gln Arg
                405                 410                 415

Glu Phe Phe Cys Phe Gly Met Asp Ile Leu Lys Leu Asp Leu Asp
                420                 425                 430

Ala Thr Arg Arg Phe Phe Asp Ala Phe Asp Leu Gln Pro His Tyr
                435                 440                 445

Trp His Gly Phe Leu Ser Ser Arg Leu Phe Leu Pro Glu Leu Leu Val
                450                 455                 460

Phe Gly Leu Ser Leu Phe Ser His Ala Ser Asn Thr Ser Arg Leu Glu
465                 470                 475                 480

Ile Met Thr Lys Gly Thr Val Pro Leu Ala Lys Met Ile Asn Asn Leu
                485                 490                 495

Val Gln Asp Arg Asp
                500

<210> SEQ ID NO 56
<211> LENGTH: 502
<212> TYPE: PRT
<213> ORGANISM: Adonis palaestina

<400> SEQUENCE: 56

Met Asp Thr Leu Leu Arg Thr His Asn Lys Leu Glu Leu Leu Pro Thr
1               5                   10                  15

Leu His Gly Phe Ala Glu Lys Gln His Leu Val Ser Thr Ser Lys Leu
                20                  25                  30

Gln Asn Gln Val Phe Arg Ile Ala Ser Arg Asn Ile His Pro Cys Arg
                35                  40                  45

Asn Gly Thr Val Lys Ala Arg Gly Ser Ala Leu Leu Glu Leu Val Pro
50                  55                  60

Glu Thr Lys Lys Glu Asn Leu Glu Phe Asp Leu Pro Ala Tyr Asp Pro
65                  70                  75                  80

Ser Arg Gly Ile Val Val Asp Leu Ala Val Val Gly Gly Pro Ala
                85                  90                  95

Gly Leu Ala Ile Ala Gln Gln Val Ser Glu Ala Gly Leu Leu Val Cys
                100                 105                 110

Ser Ile Asp Pro Ser Pro Lys Leu Ile Trp Pro Asn Asn Tyr Gly Val
                115                 120                 125

Trp Val Asp Glu Phe Glu Ala Met Asp Leu Leu Asp Cys Leu Asp Thr
                130                 135                 140

Thr Trp Ser Gly Ala Val Val Tyr Thr Asp Asp Asn Ser Lys Lys Tyr
145                 150                 155                 160
```

```
Leu Asp Arg Pro Tyr Gly Arg Val Asn Arg Lys Gln Leu Lys Ser Lys
            165                 170                 175

Met Leu Gln Lys Cys Val Thr Asn Gly Val Lys Phe His Gln Ala Lys
            180                 185                 190

Val Ile Lys Val Ile His Glu Glu Ser Lys Ser Leu Leu Ile Cys Asn
            195                 200                 205

Asp Gly Ile Thr Ile Asn Ala Thr Val Val Leu Asp Ala Thr Gly Phe
            210                 215                 220

Ser Arg Cys Leu Val Gln Tyr Asp Lys Pro Tyr Asn Pro Gly Tyr Gln
225                 230                 235                 240

Val Ala Tyr Gly Ile Met Ala Glu Val Glu His Pro Phe Asp Leu
                    245                 250                 255

Asp Lys Met Leu Phe Met Asp Trp Arg Asp Ser His Leu Asn Glu Lys
            260                 265                 270

Leu Glu Leu Lys Asp Lys Asn Arg Lys Ile Pro Thr Phe Leu Tyr Ala
            275                 280                 285

Met Pro Phe Ser Ser Thr Lys Ile Phe Leu Glu Glu Thr Ser Leu Val
            290                 295                 300

Ala Arg Pro Gly Leu Arg Phe Glu Asp Ile Gln Glu Arg Met Val Ala
305                 310                 315                 320

Arg Leu Lys His Leu Gly Ile Lys Val Lys Ser Ile Glu Glu Asp Glu
                    325                 330                 335

Arg Cys Val Ile Pro Met Gly Gly Pro Leu Pro Val Leu Pro Gln Arg
                    340                 345                 350

Val Val Gly Ile Gly Gly Thr Ala Gly Met Val His Pro Ser Thr Gly
                    355                 360                 365

Tyr Met Val Ala Arg Thr Leu Ala Ala Pro Val Val Ala Lys Ser
            370                 375                 380

Ile Val Gln Tyr Leu Gly Ser Asp Arg Ser Leu Ser Gly Asn Glu Leu
385                 390                 395                 400

Ser Ala Glu Val Trp Lys Asp Leu Trp Pro Ile Glu Arg Arg Arg Gln
                    405                 410                 415

Arg Glu Phe Phe Cys Phe Gly Met Asp Ile Leu Leu Lys Leu Asp Leu
                    420                 425                 430

Gln Gly Thr Arg Arg Phe Asp Ala Phe Phe Asp Leu Glu Pro His
            435                 440                 445

Tyr Trp His Gly Phe Leu Ser Ser Arg Leu Phe Leu Pro Glu Leu Leu
450                 455                 460

Phe Phe Gly Leu Ser Leu Phe Ser His Ala Ser Asn Ala Ser Arg Ile
465                 470                 475                 480

Glu Ile Met Ala Lys Gly Thr Val Pro Leu Val Asn Met Met Asn Asn
                    485                 490                 495

Leu Ile Gln Asp Thr Asp
            500

<210> SEQ ID NO 57
<211> LENGTH: 498
<212> TYPE: PRT
<213> ORGANISM: Capsicum sp.

<400> SEQUENCE: 57

Met Asp Thr Leu Leu Arg Thr Pro Asn Asn Leu Glu Phe Leu His Gly
1               5                   10                  15

Phe Gly Val Lys Val Ser Ala Phe Ser Ser Val Lys Ser Gln Lys Phe
            20                  25                  30
```

-continued

```
Gly Ala Lys Lys Phe Cys Glu Gly Leu Gly Ser Arg Ser Val Cys Val
         35                  40                  45
Lys Ala Ser Ser Ala Leu Leu Glu Leu Val Pro Glu Thr Lys Lys
 50                  55                  60
Glu Asn Leu Asp Phe Glu Leu Pro Met Tyr Asp Pro Ser Lys Gly Val
 65                  70                  75                  80
Val Val Asp Leu Ala Val Val Gly Gly Pro Ala Gly Leu Ala Val
                 85                  90                  95
Ala Gln Gln Val Ser Glu Ala Gly Leu Ser Val Cys Ser Ile Asp Pro
                100                 105                 110
Asn Pro Lys Leu Ile Trp Pro Asn Asn Tyr Gly Val Trp Val Asp Glu
        115                 120                 125
Phe Glu Ala Met Asp Leu Leu Asp Cys Leu Asp Ala Thr Trp Ser Gly
    130                 135                 140
Ala Ala Val Tyr Ile Asp Asp Lys Thr Thr Lys Asp Leu Asn Arg Pro
145                 150                 155                 160
Tyr Gly Arg Val Asn Arg Lys Gln Leu Lys Ser Lys Met Met Gln Lys
                165                 170                 175
Cys Ile Leu Asn Gly Val Lys Phe His Gln Ala Lys Val Ile Lys Val
                180                 185                 190
Ile His Glu Glu Ser Lys Ser Met Leu Ile Cys Asn Asp Gly Ile Thr
            195                 200                 205
Ile Gln Ala Thr Val Val Leu Asp Ala Thr Gly Phe Ser Arg Ser Leu
        210                 215                 220
Val Gln Tyr Asp Lys Pro Tyr Asn Pro Gly Tyr Gln Val Ala Tyr Gly
225                 230                 235                 240
Ile Leu Ala Glu Val Glu Glu His Pro Phe Asp Val Asn Lys Met Val
                245                 250                 255
Phe Met Asp Trp Arg Asp Ser His Leu Lys Asn Asn Val Glu Leu Lys
                260                 265                 270
Glu Arg Asn Ser Arg Ile Pro Thr Phe Leu Tyr Ala Met Pro Phe Ser
            275                 280                 285
Ser Asn Arg Ile Phe Leu Glu Glu Thr Ser Leu Val Ala Arg Pro Gly
        290                 295                 300
Leu Gly Met Asp Asp Ile Gln Glu Arg Met Val Ala Arg Leu Ser His
305                 310                 315                 320
Leu Gly Ile Lys Val Lys Ser Ile Glu Glu Asp Glu His Cys Val Ile
                325                 330                 335
Pro Met Gly Gly Pro Leu Pro Val Leu Pro Gln Arg Val Val Gly Ile
                340                 345                 350
Gly Gly Thr Ala Gly Met Val His Pro Ser Thr Gly Tyr Met Val Ala
            355                 360                 365
Arg Thr Leu Ala Ala Ala Pro Val Val Ala Asn Ala Ile Ile Gln Tyr
        370                 375                 380
Leu Ser Ser Glu Arg Ser His Ser Gly Asp Glu Leu Ser Ala Ala Val
385                 390                 395                 400
Trp Lys Asp Leu Trp Pro Ile Glu Arg Arg Gln Arg Glu Phe Phe
                405                 410                 415
Cys Phe Gly Met Asp Ile Leu Leu Lys Leu Asp Leu Pro Ala Thr Arg
                420                 425                 430
Arg Phe Phe Asp Ala Phe Phe Asp Leu Glu Pro Arg Tyr Trp His Gly
        435                 440                 445
```

```
Phe Leu Ser Ser Arg Leu Phe Leu Pro Glu Leu Ile Val Phe Gly Leu
        450                 455                 460

Ser Leu Phe Ser His Ala Ser Asn Thr Ser Arg Leu Glu Ile Met Thr
465                 470                 475                 480

Lys Gly Thr Leu Pro Leu Val His Met Ile Asn Asn Leu Leu Gln Asp
                    485                 490                 495

Lys Glu

<210> SEQ ID NO 58
<211> LENGTH: 500
<212> TYPE: PRT
<213> ORGANISM: Lycopersicon esculentum

<400> SEQUENCE: 58

Met Asp Thr Leu Leu Lys Thr Pro Asn Asn Leu Glu Phe Leu Asn Pro
 1               5                  10                  15

His His Gly Phe Ala Val Lys Ala Ser Thr Phe Arg Ser Glu Lys His
            20                  25                  30

His Asn Phe Gly Ser Arg Lys Phe Cys Glu Thr Leu Gly Arg Ser Val
        35                  40                  45

Cys Val Lys Gly Ser Ser Ala Leu Leu Glu Leu Val Pro Glu Thr
 50                  55                  60

Lys Lys Glu Asn Leu Asp Phe Glu Leu Pro Met Tyr Asp Pro Ser Lys
 65                  70                  75                  80

Gly Val Val Val Asp Leu Ala Val Val Gly Gly Pro Ala Gly Leu
                    85                  90                  95

Ala Val Ala Gln Gln Val Ser Glu Ala Gly Leu Ser Val Cys Ser Ile
                100                 105                 110

Asp Pro Asn Pro Lys Leu Ile Trp Pro Asn Asn Tyr Gly Val Trp Val
            115                 120                 125

Asp Glu Phe Glu Ala Met Asp Leu Leu Asp Cys Leu Asp Ala Thr Trp
        130                 135                 140

Ser Gly Ala Ala Val Tyr Ile Asp Asp Asn Thr Ala Lys Asp Leu His
145                 150                 155                 160

Arg Pro Tyr Gly Arg Val Asn Arg Lys Gln Leu Lys Ser Lys Met Met
                165                 170                 175

Gln Lys Cys Ile Met Asn Gly Val Lys Phe His Gln Ala Lys Val Ile
            180                 185                 190

Lys Val Ile His Glu Glu Ser Lys Ser Met Leu Ile Cys Asn Asp Gly
        195                 200                 205

Ile Thr Ile Gln Ala Thr Val Val Leu Asp Ala Thr Gly Phe Ser Arg
    210                 215                 220

Ser Leu Val Gln Tyr Asp Lys Pro Tyr Asn Pro Gly Tyr Gln Val Ala
225                 230                 235                 240

Tyr Gly Ile Leu Ala Glu Val Glu His Pro Phe Asp Val Asn Lys
                245                 250                 255

Met Val Phe Met Asp Trp Arg Asp Ser His Leu Lys Asn Asn Thr Asp
            260                 265                 270

Leu Lys Glu Arg Asn Ser Arg Ile Pro Thr Phe Leu Tyr Ala Met Pro
        275                 280                 285

Phe Ser Ser Asn Arg Ile Phe Leu Glu Glu Thr Ser Leu Val Ala Arg
    290                 295                 300

Pro Gly Leu Arg Ile Asp Asp Ile Gln Glu Arg Met Val Ala Arg Leu
305                 310                 315                 320
```

-continued

```
Asn His Leu Gly Ile Lys Val Lys Ser Ile Glu Glu Asp Glu His Cys
                325                 330                 335

Leu Ile Pro Met Gly Gly Pro Leu Pro Val Leu Pro Gln Arg Val Val
            340                 345                 350

Gly Ile Gly Gly Thr Ala Gly Met Val His Pro Ser Thr Gly Tyr Met
            355                 360                 365

Val Ala Arg Thr Leu Ala Ala Pro Val Ala Asn Ala Ile Ile
370                 375                 380

Gln Tyr Leu Gly Ser Glu Arg Ser His Ser Gly Asn Glu Leu Ser Thr
385                 390                 395                 400

Ala Val Trp Lys Asp Leu Trp Pro Ile Glu Arg Arg Gln Arg Glu
                405                 410                 415

Phe Phe Cys Phe Gly Met Asp Ile Leu Leu Lys Leu Asp Leu Pro Ala
            420                 425                 430

Thr Arg Arg Phe Phe Asp Ala Phe Phe Asp Leu Glu Pro Arg Tyr Trp
            435                 440                 445

His Gly Phe Leu Ser Ser Arg Leu Phe Leu Pro Glu Leu Ile Val Phe
        450                 455                 460

Gly Leu Ser Leu Phe Ser His Ala Ser Asn Thr Ser Arg Phe Glu Ile
465                 470                 475                 480

Met Thr Lys Gly Thr Val Pro Leu Val Asn Met Ile Asn Asn Leu Leu
                485                 490                 495

Gln Asp Lys Glu
            500

<210> SEQ ID NO 59
<211> LENGTH: 500
<212> TYPE: PRT
<213> ORGANISM: Nicotiana sp.

<400> SEQUENCE: 59

Met Asp Thr Leu Leu Lys Thr Pro Asn Lys Leu Glu Phe Leu His Pro
1               5                   10                  15

Val His Gly Phe Ser Val Lys Ala Ser Ser Phe Asn Ser Val Lys Pro
            20                  25                  30

His Lys Phe Gly Ser Arg Lys Ile Cys Glu Asn Trp Gly Lys Gly Val
            35                  40                  45

Cys Val Lys Ala Lys Ser Ser Ala Leu Leu Glu Leu Val Pro Glu Thr
        50                  55                  60

Lys Lys Glu Asn Leu Asp Phe Glu Leu Pro Met Tyr Asp Pro Ser Lys
65                  70                  75                  80

Gly Leu Val Val Asp Leu Ala Val Gly Gly Pro Ala Gly Leu
                85                  90                  95

Ala Val Ala Gln Gln Val Ser Glu Ala Gly Leu Ser Val Ser Ile
            100                 105                 110

Asp Pro Ser Pro Lys Leu Ile Trp Pro Asn Asn Tyr Gly Val Trp Val
            115                 120                 125

Asp Glu Phe Glu Ala Met Asp Leu Leu Asp Cys Leu Asp Ala Thr Trp
        130                 135                 140

Ser Gly Thr Val Val Tyr Ile Asp Asp Asn Thr Thr Lys Asp Leu Asp
145                 150                 155                 160

Arg Pro Tyr Gly Arg Val Asn Arg Lys Gln Leu Lys Ser Lys Met Met
                165                 170                 175

Gln Lys Cys Ile Leu Asn Gly Val Lys Phe His His Ala Lys Val Ile
            180                 185                 190
```

```
Lys Val Ile His Glu Ala Lys Ser Met Leu Ile Cys Asn Asp Gly
        195                 200                 205

Val Thr Ile Gln Ala Thr Val Val Leu Asp Ala Thr Gly Phe Ser Arg
    210                 215                 220

Cys Leu Val Gln Tyr Asp Lys Pro Tyr Lys Pro Gly Tyr Gln Val Ala
225                 230                 235                 240

Tyr Gly Ile Leu Ala Glu Val Glu His Pro Phe Asp Thr Ser Lys
                245                 250                 255

Met Val Leu Met Asp Trp Arg Asp Ser His Leu Gly Asn Asn Met Glu
            260                 265                 270

Leu Lys Glu Arg Asn Arg Lys Val Pro Thr Phe Leu Tyr Ala Met Pro
    275                 280                 285

Phe Ser Ser Asn Lys Ile Phe Leu Glu Glu Thr Ser Leu Val Ala Arg
    290                 295                 300

Pro Gly Leu Arg Met Asp Asp Ile Gln Glu Arg Met Val Ala Arg Leu
305                 310                 315                 320

Asn His Leu Gly Ile Lys Val Lys Ser Ile Glu Glu Asp Glu His Cys
                325                 330                 335

Val Ile Pro Met Gly Gly Ser Leu Pro Val Ile Pro Gln Arg Val Val
            340                 345                 350

Gly Thr Gly Gly Thr Ala Gly Leu Val His Pro Ser Thr Gly Tyr Met
        355                 360                 365

Val Ala Arg Thr Leu Ala Ala Pro Val Val Ala Asn Ala Ile Ile
    370                 375                 380

His Tyr Leu Gly Ser Glu Lys Asp Leu Leu Gly Asn Glu Leu Ser Ala
385                 390                 395                 400

Ala Val Trp Lys Asp Leu Trp Pro Ile Glu Arg Arg Gln Arg Glu
                405                 410                 415

Phe Phe Cys Phe Gly Met Asp Ile Leu Leu Lys Leu Asp Leu Pro Ala
            420                 425                 430

Thr Arg Arg Phe Phe Asp Ala Phe Phe Asp Leu Glu Pro Arg Tyr Trp
        435                 440                 445

His Gly Phe Leu Ser Ser Arg Leu Tyr Leu Pro Glu Leu Ile Phe Phe
    450                 455                 460

Gly Leu Ser Leu Phe Ser Arg Ala Ser Asn Thr Ser Arg Ile Glu Ile
465                 470                 475                 480

Met Thr Lys Gly Thr Leu Pro Leu Val Asn Met Ile Asn Asn Leu Leu
                485                 490                 495

Gln Asp Thr Glu
            500

<210> SEQ ID NO 60
<211> LENGTH: 511
<212> TYPE: PRT
<213> ORGANISM: Tagetes erecta

<400> SEQUENCE: 60

Met Asp Thr Phe Leu Arg Thr Tyr Asn Ser Phe Glu Phe Val His Pro
1               5                   10                  15

Ser Asn Lys Phe Ala Gly Asn Leu Asn Asn Leu Asn Gln Leu Asn Gln
            20                  25                  30

Ser Lys Ser Gln Phe Gln Asp Phe Arg Phe Gly Pro Lys Lys Ser Gln
        35                  40                  45

Phe Lys Leu Gly Gln Lys Tyr Cys Val Lys Ala Ser Ser Ser Ala Leu
```

-continued

```
            50                  55                  60
Leu Glu Leu Val Pro Glu Ile Lys Lys Glu Asn Leu Asp Phe Asp Leu
 65                  70                  75                  80
Pro Met Tyr Asp Pro Ser Arg Asn Val Val Asp Leu Val Val Val Val
                     85                  90                  95
Gly Gly Gly Pro Ser Gly Leu Ala Val Ala Gln Gln Val Ser Glu Ala
                100                 105                 110
Gly Leu Thr Val Cys Ser Ile Asp Pro Ser Pro Lys Leu Ile Trp Pro
                115                 120                 125
Asn Asn Tyr Gly Val Trp Val Asp Glu Phe Glu Ala Met Asp Leu Leu
130                 135                 140
Asp Cys Leu Asp Thr Thr Trp Ser Ser Ala Val Val Tyr Ile Asp Glu
145                 150                 155                 160
Lys Ser Thr Lys Ser Leu Asn Arg Pro Tyr Ala Arg Val Asn Arg Lys
                165                 170                 175
Gln Leu Lys Thr Lys Met Leu Gln Lys Cys Ile Ala Asn Gly Val Lys
                180                 185                 190
Phe His Gln Ala Lys Val Ile Lys Val Ile His Glu Glu Leu Lys Ser
                195                 200                 205
Leu Leu Ile Cys Asn Asp Gly Val Thr Ile Gln Ala Thr Leu Val Leu
                210                 215                 220
Asp Ala Thr Gly Phe Ser Arg Ser Leu Val Gln Tyr Asp Lys Pro Tyr
225                 230                 235                 240
Asn Pro Gly Tyr Gln Val Ala Tyr Gly Ile Leu Ala Glu Val Glu Glu
                245                 250                 255
His Pro Phe Asp Val Asp Lys Met Leu Phe Met Asp Trp Arg Asp Ser
                260                 265                 270
His Leu Asp Gln Asn Leu Glu Ile Lys Ala Arg Asn Ser Arg Ile Pro
                275                 280                 285
Thr Phe Leu Tyr Ala Met Pro Phe Ser Ser Thr Arg Ile Phe Leu Glu
                290                 295                 300
Glu Thr Ser Leu Val Ala Arg Pro Gly Leu Lys Met Glu Asp Ile Gln
305                 310                 315                 320
Glu Arg Met Ala Tyr Arg Leu Lys His Leu Gly Ile Lys Val Lys Ser
                325                 330                 335
Ile Glu Glu Asp Glu Arg Cys Val Ile Pro Met Gly Gly Pro Leu Pro
                340                 345                 350
Val Leu Pro Gln Arg Val Leu Gly Ile Gly Gly Thr Ala Gly Met Val
                355                 360                 365
His Pro Ser Thr Gly Tyr Met Val Ala Arg Thr Leu Ala Ala Ala Pro
                370                 375                 380
Ile Val Ala Lys Ser Ile Ile Arg Tyr Leu Asn Asn Glu Lys Ser Met
385                 390                 395                 400
Val Ala Asp Val Thr Gly Asp Asp Leu Ala Ala Gly Ile Trp Arg Glu
                405                 410                 415
Leu Trp Pro Ile Glu Arg Arg Arg Gln Arg Glu Phe Phe Cys Phe Gly
                420                 425                 430
Met Asp Ile Leu Leu Lys Leu Asp Leu Glu Gly Thr Arg Arg Phe Phe
                435                 440                 445
Asp Ala Phe Phe Asp Leu Glu Pro Arg Tyr Trp His Gly Phe Leu Ser
                450                 455                 460
Ser Arg Leu Phe Leu Pro Glu Leu Val Thr Phe Gly Leu Ser Leu Phe
465                 470                 475                 480
```

-continued

```
Gly His Ala Ser Asn Thr Cys Arg Val Glu Ile Met Ala Lys Gly Thr
                485                 490                 495

Leu Pro Leu Ala Thr Met Ile Gly Asn Leu Val Arg Asp Arg Glu
            500                 505                 510

<210> SEQ ID NO 61
<211> LENGTH: 503
<212> TYPE: PRT
<213> ORGANISM: Narcissus sp.

<400> SEQUENCE: 61

Met Asp Thr Leu Leu Arg Thr His Asn Arg Leu Glu Leu Leu Tyr Pro
  1               5                  10                  15

Leu His Glu Leu Ala Lys Arg His Phe Leu Ser Pro Ser Pro Asn Pro
                 20                  25                  30

Gln Asn Pro Asn Phe Lys Phe Phe Ser Arg Lys Pro Tyr Gln Lys Lys
             35                  40                  45

Cys Arg Asn Gly Tyr Ile Gly Val Ser Ser Asn Gln Leu Leu Asp Leu
     50                  55                  60

Val Pro Glu Ile Lys Lys Glu His Leu Glu Phe Asp Leu Pro Leu Tyr
 65                  70                  75                  80

Asp Pro Ser Lys Ala Leu Thr Leu Asp Leu Ala Val Val Gly Gly Gly
                 85                  90                  95

Pro Leu Ala Arg Ser Cys Ser Thr Ser Leu Gly Gly Gly Leu Ser Val
            100                 105                 110

Val Ser Ile Asp Pro Asn Pro Lys Leu Ile Trp Pro Asn Asn Tyr Gly
        115                 120                 125

Val Trp Val Asp Glu Phe Glu Asp Met Asp Leu Leu Asp Cys Leu Asp
130                 135                 140

Ala Thr Trp Ser Gly Ala Ile Val Tyr Val Asp Asp Arg Ser Thr Lys
145                 150                 155                 160

Asn Leu Ser Arg Pro Tyr Ala Arg Val Asn Arg Lys Asn Leu Lys Ser
                165                 170                 175

Lys Met Met Lys Lys Cys Val Ser Asn Gly Val Arg Phe His Gln Ala
            180                 185                 190

Thr Val Val Lys Ala Met His Glu Glu Lys Ser Tyr Leu Ile Cys
        195                 200                 205

Ser Asp Gly Val Thr Ile Asp Ala Arg Val Val Leu Asp Ala Thr Gly
    210                 215                 220

Phe Ser Arg Cys Leu Val Gln Tyr Asp Lys Pro Tyr Asn Pro Gly Tyr
225                 230                 235                 240

Gln Val Ala Tyr Gly Ile Leu Ala Glu Val Glu His Pro Phe Asp
                245                 250                 255

Val Asp Lys Met Val Phe Met Asp Trp Arg Asp Ser His Leu Asn Gly
            260                 265                 270

Lys Ala Glu Leu Asn Glu Arg Asn Ala Lys Ile Pro Thr Phe Leu Tyr
        275                 280                 285

Ala Met Pro Phe Ser Ser Asn Arg Ile Phe Leu Glu Glu Thr Ser Leu
    290                 295                 300

Val Ala Arg Pro Gly Leu Lys Met Glu Asp Ile Gln Glu Arg Met Val
305                 310                 315                 320

Ala Arg Leu Asn His Leu Gly Ile Arg Ile Lys Ser Ile Glu Glu Asp
                325                 330                 335

Glu Arg Cys Val Ile Pro Met Gly Gly Pro Leu Pro Val Ile Pro Gln
```

-continued

```
                340                 345                 350
Arg Val Val Gly Ile Gly Gly Thr Ala Gly Met Val His Pro Ser Thr
        355                 360                 365
Gly Tyr Met Val Ala Arg Thr Leu Ala Ala Ala Pro Ile Val Ala Asn
    370                 375                 380
Ser Ile Val Gln Tyr Leu Val Ser Asp Ser Gly Leu Ser Gly Asn Asp
385                 390                 395                 400
Leu Ser Ala Asp Val Trp Lys Asp Leu Trp Pro Ile Glu Arg Arg Arg
                405                 410                 415
Gln Arg Glu Phe Phe Cys Phe Gly Met Asp Ile Leu Leu Lys Leu Asp
                420                 425                 430
Leu Glu Gly Thr Arg Arg Phe Phe Asp Ala Phe Asp Leu Glu Pro
            435                 440                 445
Arg Tyr Trp His Gly Phe Leu Ser Ser Arg Leu Phe Leu Pro Glu Leu
    450                 455                 460
Val Pro Phe Gly Leu Ser Leu Phe Ser His Ala Ser Asn Thr Cys Lys
465                 470                 475                 480
Leu Glu Ile Met Ala Lys Gly Thr Leu Pro Leu Val Asn Met Ile Asn
                485                 490                 495
Asn Leu Val Gln Asp Arg Asp
                500
```

US 6,642,021 B2

METHODS OF PRODUCING CAROTENOIDS BY THE EXPRESSION OF PLANT ε-CYCLASE GENES

CROSS-REFERENCE TO RELATED APPLICATIONS

This application is a continuation-in-part of U.S. application Ser. No. 09/088,724, filed Jun. 2, 1998 now abandoned, Ser. No. 09/088,725, filed Jun. 2, 1998 now abandoned, and Ser. No. 08/937,155, filed Sep. 25, 1997, U.S. application Ser. No. 08/937,155 being a divisional of U.S. application Ser. No. 08/624,125, filed Mar. 29, 1996, now U.S. Pat. No. 5,744,341.

BACKGROUND OF THE INVENTION

1. Field of the Invention

The present invention describes nucleic acid sequences for eukaryotic genes encoding ∈ lycopene ∈-cyclase (also known as ∈-cyclase and ∈ lycopene cyclase), isopentenyl pyrophosphate isomerase (IPP) and β-carotene hydroxylase as well as vectors containing the same and hosts transformed with said vectors. The present invention also provides methods for augmenting the accumulation of carotenoids, changing the composition of the carotenoids, and producing novel and rare carotenoids. The present invention provides methods for controlling the ratio or relative amounts of various carotenoids in a host. The invention also relates to modified lycopene ∈-cyclase, IPP isomerase and β-carotene hydroxylase. Additionally, the present invention provides a method for screening for genes and cDNAs encoding enzymes of carotenoid biosynthesis and metabolism.

1. Background of the Invention

Carotenoid pigments with cyclic endgroups are essential components of the photosynthetic apparatus in oxygenic photosynthetic organisms (e.g., cyanobacteria, algae and plants; Goodwin, 1980). The symmetrical bicyclic yellow carotenoid pigment β-carotene (or, in rare cases, the asymmetrical bicyclic α-carotene) is intimately associated with the photosynthetic reaction centers and plays a vital role in protecting against potentially lethal photooxidative damage (Koyama, 1991). β-carotene and other carotenoids derived from it or from α-carotene also serve as light-harvesting pigments (Siefermann-Harms, 1987), are involved in the thermal dissipation of excess light energy captured by the light-harvesting antenna (Demmig-Adams & Adams, 1992), provide substrate for the biosynthesis of the plant growth regulator abscisic acid (Rock & Zeevaart, 1991; Parry & Horgan, 1991), and are precursors of vitamin A in human and animal diets (Krinsky, 1987). Plants also exploit carotenoids as coloring agents in flowers and fruits to attract pollinators and agents of seed dispersal (Goodwin, 1980). The color provided by carotenoids is also of agronomic value in a number of important crops. Carotenoids are currently harvested from a variety of organisms, including plants, algae, yeasts, cyanobacteria and bacteria, for use as pigments in food and feed.

The probable pathway for formation of cyclic carotenoids in plants, algae and cyanobacteria is illustrated in FIG. 1. Two types of cyclic endgroups or rings are commonly found in higher plant carotenoids, these are referred to as the β (beta) and ∈ (epsilon) rings (FIG. 3). The precursor acyclic endgroup (no ring structure) is referred to as the Ψ (psi) endgroup. The β and ∈ endgroups differ only in the position of the double bond in the ring. Carotenoids with two β rings are ubiquitous, and those with one β and one ∈ ring are common, but carotenoids with two ∈ rings are uncommon. β-carotene (FIG. 1) has two β-endgroups and is a symmetrical compound that is the precursor of a number of other important plant carotenoids such as zeaxanthin and violaxanthin (FIG. 2).

Genes encoding enzymes of carotenoid biosynthesis have previously been isolated from a variety of sources including bacteria (Armstrong et al., 1989, Mol. Gen. Genet. 216, 254–268; Misawa et al., 1990, J. Bacteriol., 172, 6704–12), fungi (Schmidhauser et al., 1990, Mol. Cell. Biol. 10, 5064–70), cyanobacteria (Chamovitz et al., 1990, Z. Naturforsch, 45c, 482–86; Cunningham et al., 1994) and higher plants (Bartley et al., Proc. Natl. Acad. Sci USA 88, 6532–36; Martinez-Ferez & Vioque, 1992, Plant Mol. Biol. 18, 981–83). Many of the isolated enzymes show a great diversity in structure, function and inhibitory properties between sources. For example, phytoene desaturases from the cyanobacterium Synechococcus and from higher plants and green algae carry out a two-step desaturation to yield ζ-carotene as a reaction product. In plants and cyanobacteria a second enzyme (ζ-carotene desaturase), similar in amino acid sequence to the phytoene desaturase, catalyzes two additional desaturations to yield lycopene. In contrast, a single desaturase enzyme from Erwinia herbicola and from other bacteria introduces all four double bonds required to form lycopene. The Erwinia and other bacterial desaturases bear little amino acid sequence similarity to the plant and cyanobacterial desaturase enzymes, and are thought to be of unrelated ancestry. Therefore, even with a gene in hand from one source, it may be difficult to identify a gene encoding an enzyme of similar function in another organism. In particular, the sequence similarity between certain of the prokaryotic and eukaryotic genes encoding enzymes of carotenoid biosynthesis is quite low.

Further, the mechanism of gene expression in prokaryotes and eukaryotes appears to differ sufficiently such that one cannot expect that an isolated eukaryotic gene will be properly expressed in a prokaryotic host.

The difficulties in isolating genes encoding enzymes with similar functions is exemplified by recent efforts to isolate the gene encoding the enzyme that catalyzes the formation of β-carotene from the acyclic precursor lycopene. Although a gene encoding an enzyme with this function had been isolated from a bacterium, it had not been isolated from any photosynthetic procaryote or from any eukaryotic organism. The isolation and characterization of the enzyme catalyzing formation of β-carotene in the cyanobacterium Synechococcus PCC7942 was described by the present inventors and others (Cunningham et al., 1993 and 1994). The amino acid sequence similarity of the cyanobacterial enzyme to the various bacterial lycopene β-cyclases is so low (ca. 18–25% overall; Cunningham et al., 1994) that there is much uncertainty as to whether they share a common ancestry or, instead, represent an example of convergent evolution.

The need remains for the isolation of eukaryotic and prokaryotic genes and cDNAs encoding polypeptides involved in the carotenoid biosynthetic pathway, including those encoding a lycopene ∈-cyclase, IPP isomerase and β-carotene hydroxylase. There remains a need for methods to enhance the production of carotenoids, to alter the composition of carotenoids, and to reduce or eliminate carotenoid production. There also remains a need in the art for methods for screening for genes and cDNAs encoding enzymes of carotenoid biosynthesis and metabolism.

SUMMARY OF THE INVENTION

Accordingly, a first object of this invention is to provide purified and/or isolated nucleic acids which encode enzymes involved in carotenoid biosynthesis; in particular, lycopene ∈-cyclase, IPP isomerase and β-carotene hydroxylase.

A second object of this invention is to provide purified and/or isolated nucleic acids which encode enzymes which produce novel or uncommon carotenoids.

A third object of the present invention is to provide vectors containing said genes.

A fourth object of the present invention is to provide hosts transformed with said vectors.

Another object of the present invention is to provide hosts which accumulate novel or uncommon carotenoids or which accumulate greater amounts of specific or total carotenoids.

Another object of the present invention is to provide hosts with inhibited and/or altered carotenoid production.

Another object of this invention is to secure the expression of eukaryotic carotenoid-related genes in a recombinant prokaryotic host.

Yet another object of the present invention is to provide a method for screening for eukaryotic and prokaryotic genes and cDNAs which encode enzymes involved in carotenoid biosynthesis and metabolism.

An additional object of the invention is to provide a method for manipulating carotenoid biosynthesis in photosynthetic organisms by inhibiting the synthesis of certain enzymatic products to cause accumulation of precursor compounds.

Another object of the invention is to provide modified lycopene ∈-cyclase, IPP isomerase and βcarotene hydroxylase.

These and other objects of the present invention have been realized by the present inventors as described below.

A subject of the present invention is an isolated and/or purified nucleic acid sequence which encodes for a protein having lycopene ∈-cyclase, IPP isomerase or β-carotene hydroxylase enzyme activity and having the amino acid sequence of SEQ ID NOS:2, 4, 14–21, 23 or 25–27.

The invention also includes vectors which comprise any of the nucleic acid sequences listed above, and host cells transformed with such vectors.

Another subject of the present invention is a method of producing or enhancing the production of a carotenoid in a host cell, comprising inserting into the host cell a vector comprising a heterologous nucleic acid sequence which encodes for a protein having lycopene ∈-cyclase, IPP isomerase or β-carotene hydroxylase enzyme activity, wherein the heterologous nucleic acid sequence is operably linked to a promoter; and expressing the heterologous nucleic acid sequence to produce the protein.

Yet another subject of the present invention is a method of modifying the production of carotenoids in a host cell, the method comprising inserting into the host cell a vector comprising a heterologous nucleic acid sequence which produces an RNA and/or encodes for a protein which modifies lycopene ∈-cyclase, IPP isomerase or β-carotene hydroxylase enzyme activity, relative to an untransformed host cell, wherein the heterologous nucleic acid sequence is operably linked to a promoter; and expressing the heterologous nucleic acid sequence in the host cell to modify the production of the carotenoids in the host cell, relative to the untransformed host cell.

The present invention also includes a method of expressing, in a host cell, a heterologous nucleic acid sequence which encodes for a protein having lycopene ∈-cyclase, IPP isomerase or β-carotene hydroxylase enzyme activity, the method comprising inserting into the host cell a vector comprising the heterologous nucleic acid sequence, wherein the heterologous nucleic acid sequence is operably linked to a promoter; and expressing the heterologous nucleic acid sequence.

Also included is a method of expressing, in a host cell, a heterologous nucleic acid sequence which encodes for a protein which modifies lycopene ∈-cyclase, IPP isomerase or β-carotene hydroxylase enzyme activity in the host cell, relative to an untransformed host cell, the method comprising inserting into the host cell a vector comprising the heterologous nucleic acid sequence, wherein the heterologous nucleic acid sequence is operably linked to a promoter; and expressing the heterologous nucleic acid sequence.

Another subject of the present invention is a method for screening for genes and cDNAs which encode enzymes involved in carotenoid biosynthesis and metabolism.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 is a DNA sequence and the predicted amino acid sequence of a lycopene ∈-cyclase cDNA isolated from A. thaliana (SEQ ID NOS:1 and 2). These sequences were deposited under Genbank accession number U50738. This cDNA is incorporated into the plasmid pATeps.

FIG. 5 is a DNA sequence encoding the β-carotene hydroxylase isolated from A. thaliana (SEQ ID NO:3). This cDNA is incorporated into the plasmid pATOHB.

FIG. 6 is an alignment of the predicted amino acid sequences of A. thaliana β-carotene hydroxylase (SEQ ID NO:4) with those of the bacterial β-carotene hydroxylase enzymes from Alicalgenes sp. (SEQ ID NO:5) (Genbank D58422), *Erwinia herbicola* Eho10 (SEQ ID NO.: 6)

Figure 1:
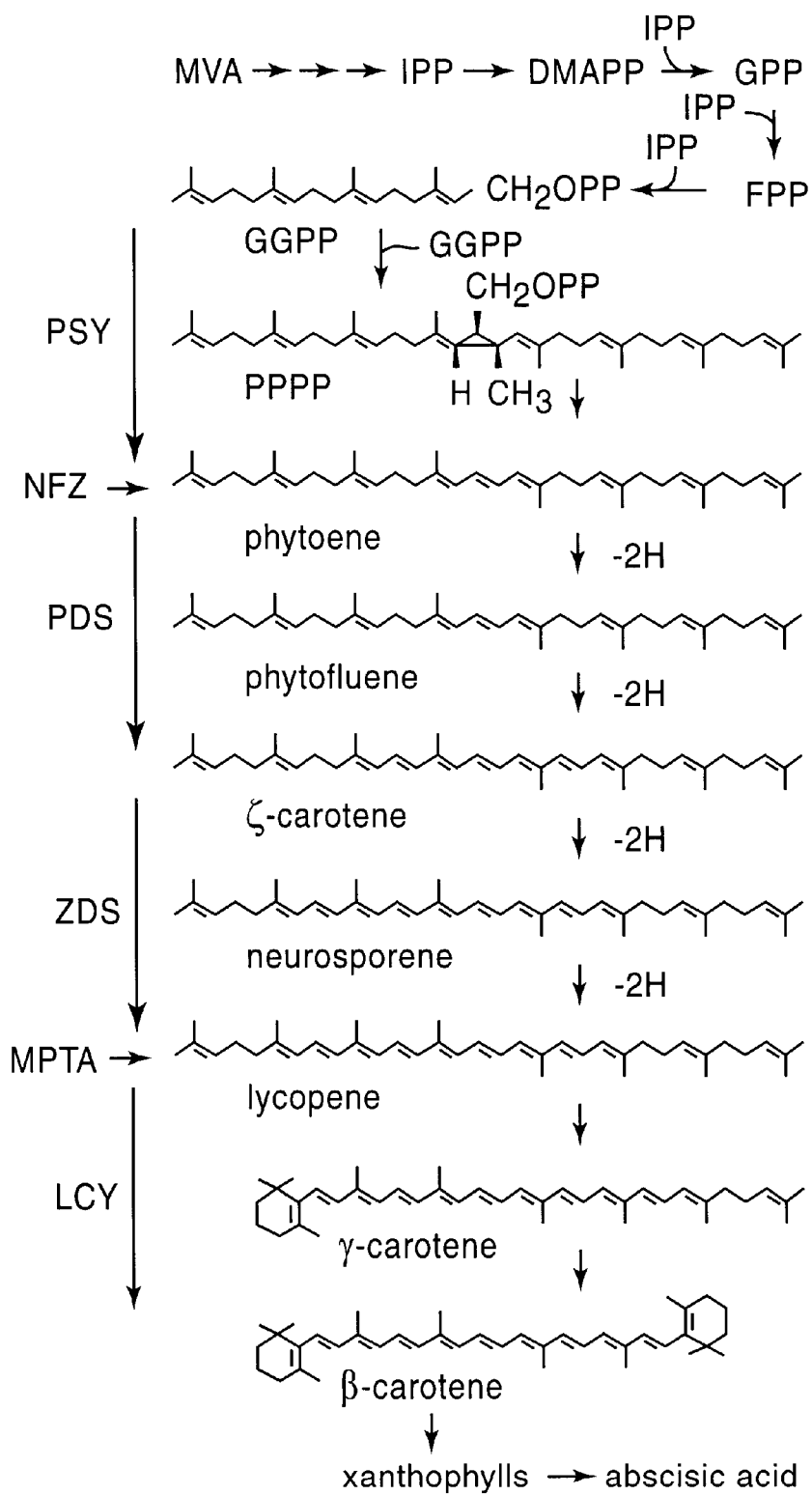
FIG. 1 is a schematic representation of the putative pathway of β-carotene biosynthesis in cyanobacteria, algae and plants. The enzymes catalyzing various steps are indicated at the left. Target sites of the bleaching herbicides NFZ and MPTA are also indicated at the left. Abbreviations: DMAPP, dimethylallyl pyrophosphate; FPP, farnesyl pyrophosphate; GGPP, geranylgeranyl pyrophosphate; GPP, geranyl pyrophosphate; IPP, isopentenyl pyrophosphate; LCY, lycopene cyclase; MVA, mevalonic acid; MPTA, 2-(4-methylphenoxy)triethylamine hydrochloride; NFZ, norflurazon; PDS, phytoene desaturase; PSY, phytoene synthase; ZDS, ζ-carotene desaturase; PPPP, prephytoene pyrophosphate.

(GenBank M872280), *Erwinia uredovora* (SEQ ID NO.: 7) (GenBank D90087) and *Agrobacterium aurianticum* (SEQ ID NO.: 8) (GenBank D58420). A consensus sequence is also shown. All five genes are identical where a capital letter appears in the consensus. A lowercase letter indicates that three of five, including *A. thaliana*, have the identical residue. TM; transmembrane.

FIG. 7 is a DNA sequence of a cDNA encoding an IPP isomerase isolated from *A. thaliana* (SEQ ID NO:9). This cDNA is incorporated into the plasmid pATDP5.

FIG. 8 is a DNA sequence of a second cDNA encoding another IPP isomerase isolated from *A. thaliana* (SEQ ID NO:10). This cDNA is incorporated into the plasmid pATDP7.

FIG. 9 is a DNA sequence of a cDNA encoding an IPP isomerase isolated from *Haematococcus pluvialis* (SEQ ID NO:11). This cDNA is incorporated into the plasmid pHP04.

FIG. 10 is a DNA sequence of a second cDNA encoding another IPP isomerase isolated from *Haematococcus pluvialis* (SEQ ID NO:12). This cDNA is incorporated into the plasmid pHP05.

FIG. 11 is an alignment of the amino acid sequences predicted by IPP isomerase cDNAs isolated from *A. thaliana* (SEQ ID NO.: 16 and 18), *H. pluvialis* (SEQ ID NOS.: 14 and 15), *Clarkia breweri* (SEQ ID NO.: 17) (See, Blanc & Pichersky, Plant Physiol. (1995) 108:855; Genbank accession no. X82627) and *Saccharomyces cerevisiae* (SEQ ID NO.: 19) (Genbank accession no. J05090).

FIG. 12 is a DNA sequence of the cDNA encoding an IPP isomerase isolated from *Tagetes erecta* (marigold; SEQ ID NO:13). This cDNA is incorporated into the plasmid pPMDP1. xxx's denote a region not originally sequenced. FIG. 21A shows the complete marigold sequence.

FIG. 13 is an alignment of the consensus sequence of four plant β-cyclases (SEQ ID NO.: 20) with the *A. thaliana* lycopene ∈-cyclase (SEQ ID NO.: 21). A capital letter in the plant β consensus is used where all four β-cyclase genes predict the same amino acid residue in this position. A small letter indicates that an identical residue was found in three of the four. Dashes indicate that the amino acid residue was not conserved and dots in the sequence denote a gap. A consensus for the aligned sequences is given, in capital letters below the alignment, where the β- and ∈-cyclases have the same amino acid residue. Arrows indicate some of the conserved amino acids that will be used as junction sites for construction of chimeric cyclases with novel enzymatic activities. Several regions of interest including a sequence signature indicative of a dinucleotide-binding motif and two predicted transmembrane (TM) helical regions are indicated below the alignment and are underlined.

FIG. 14 shows the nucleotide (SEQ ID NO:22) and amino acid sequences (SEQ ID NO:23) of the *Adonis palaestina* (pheasant's eye) ∈-cyclase cDNA #5.

FIG. 15A shows the nucleotide (SEQ ID NO:24) and amino acid sequences (SEQ ID NO:25) of a potato ∈-cyclase cDNA. FIG. 15B shows the amino acid sequence (SEQ ID NO:26) of a chimeric lettuce/potato lycopene ∈-cyclase. Amino acids in lower case are from the lettuce cDNA and those in upper case are from the potato cDNA. The product of this chimeric cDNA has ∈-cyclase activity and converts lycopene to the monocyclic δ-carotene.

FIG. 16 shows a comparison between the amino acid sequences of the Arabidopsis ∈-cyclase (SEQ ID NO:27) and the potato ∈-cyclase (SEQ ID NO:25).

FIG. 17A shows the nucleotide sequence of the *Adonis palaestina* Ipi1 (SEQ ID NO:28) and FIG. 17B shows the nucleotide sequence of the *Adonis palaestina* Ipi2 (SEQ ID NO:29).

FIG. 18A shows the nucleotide sequence of the *Haematoccus pluvialis* Ipi1 (SEQ ID NO:11) and FIG. 18B shows the nucleotide sequence of the *Haematoccus pluvialis* Ipi2 (SEQ ID NO:30).

FIG. 19A shows the nucleotide sequence of the *Lactuca sativa* (romaine lettuce) Ipi1 (SEQ ID NO:31) and FIG. 19B shows the nucleotide sequence of the *Lactuca sativa* Ipi2 (SEQ ID NO:32).

FIG. 20 shows the nucleotide sequence of the *Chlamydomonas reinhardtii* Ipi1 (SEQ ID NO:33).

FIG. 21A shows the nucleotide sequence of the *Tagetes erecta* (marigold) Ipi1 (SEQ ID NO:34) and FIG. 21B shows the nucleotide sequence of the *Oryza sativa* (rice) Ipi1 (SEQ ID NO:35).

FIG. 22 shows an amino acid sequence alignment of various plant and green algal isopentenyl isomerases (IPI) (SEQ ID NOS 36–41, 16, 42–45, respectively, in order of appearance).

FIGS. 23A and 23B show comparison between *Adonis palaestina* ∈-cyclase cDNA #3 (SEQ ID NO: 46) and cDNA #5 (SEQ ID NO: 62) nucleotide sequences.

FIG. 24 shows a comparison between *Adonis palaestina* ∈-cyclase cDNA #3 (SEQ ID NO: 47) and cDNA #5 (SEQ ID NO: 23) predicted amino acid sequences.

Figure 25A:
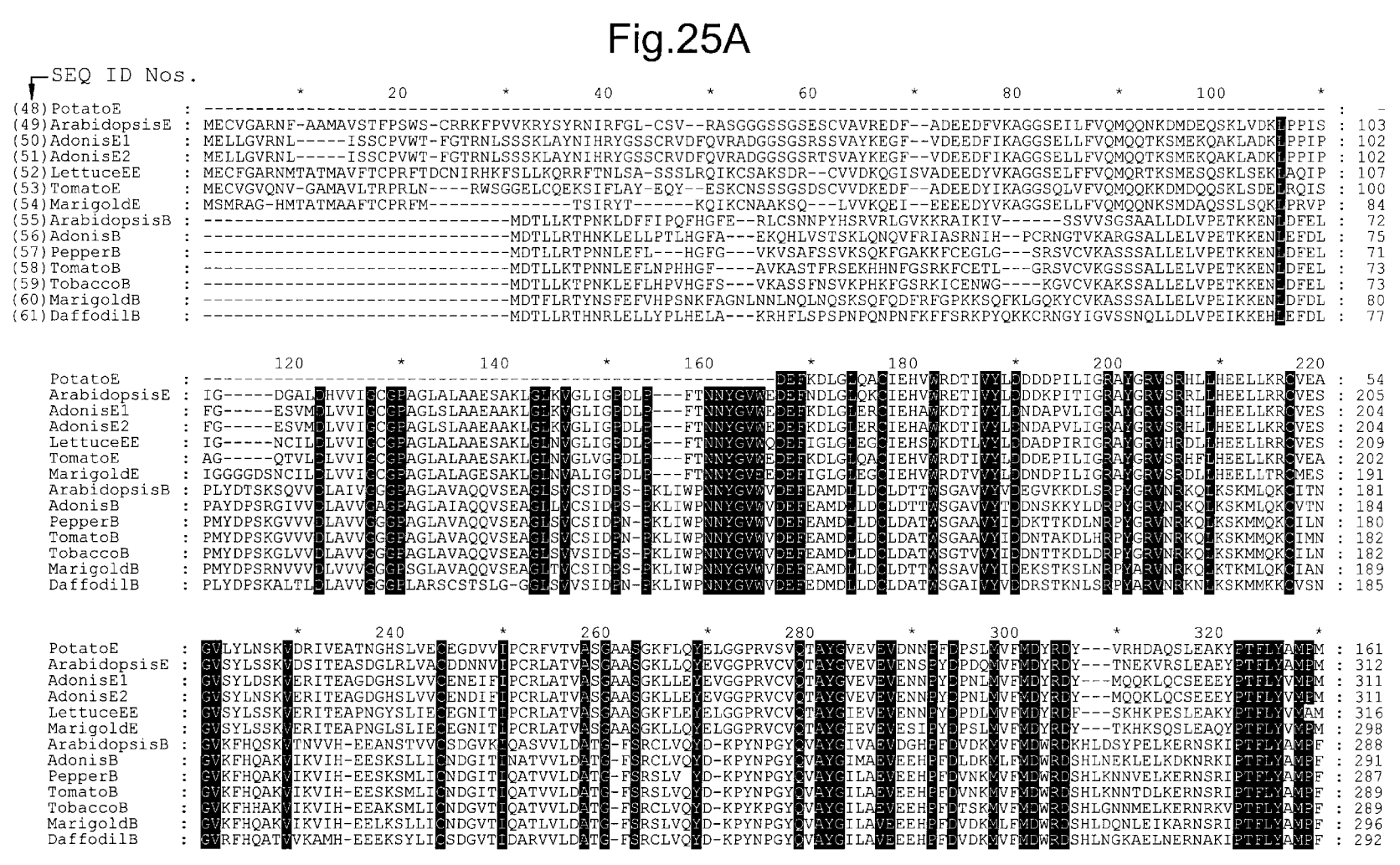
Figure 25B:
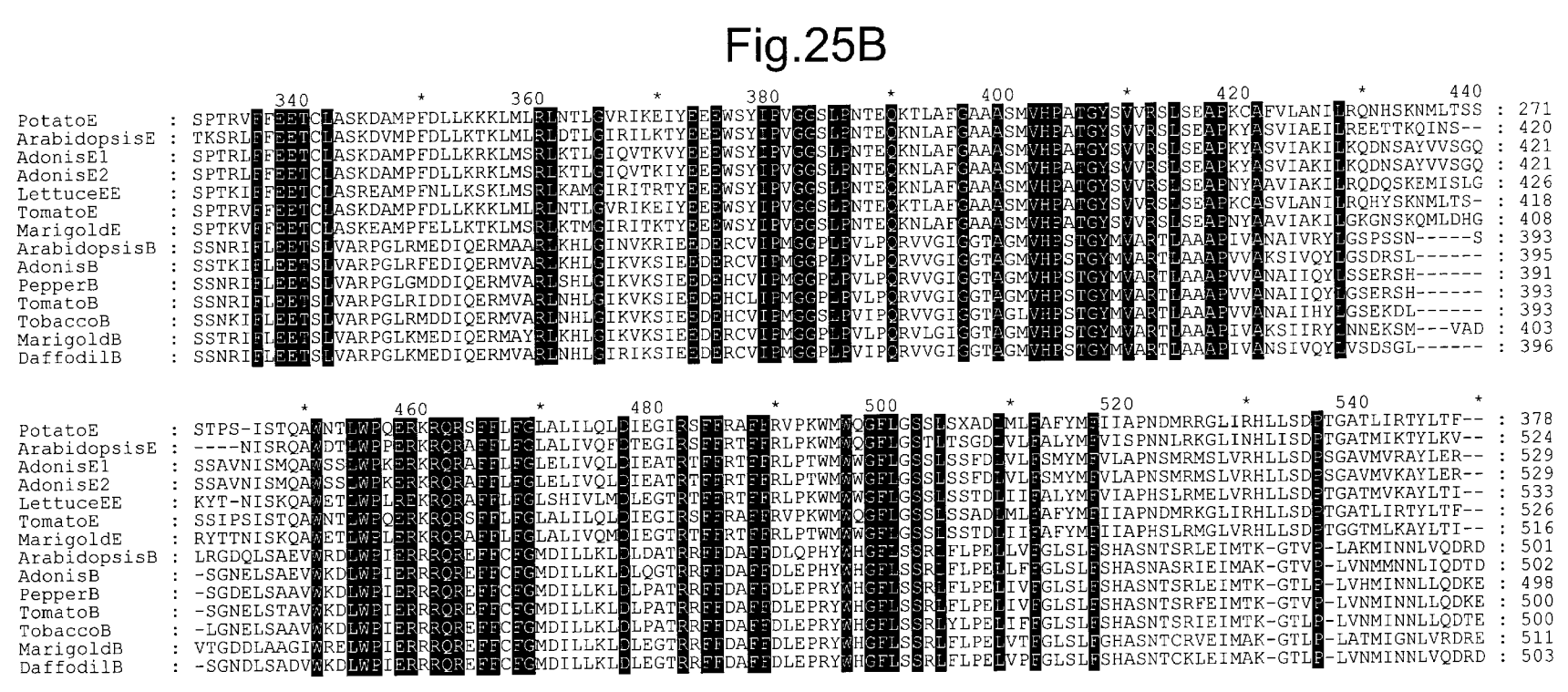

FIGS. 25A and 25B show a sequence alignment of various plant β- and ∈-cyclases (SEQ ID NOS 48–61, respectively, in order of appearance). Those sequences outlined in grey denote identical sequences among the ∈-cyclases. Those sequences outlined in black denote identical sequences among both the β- and ∈-cyclases.

Figure 26:
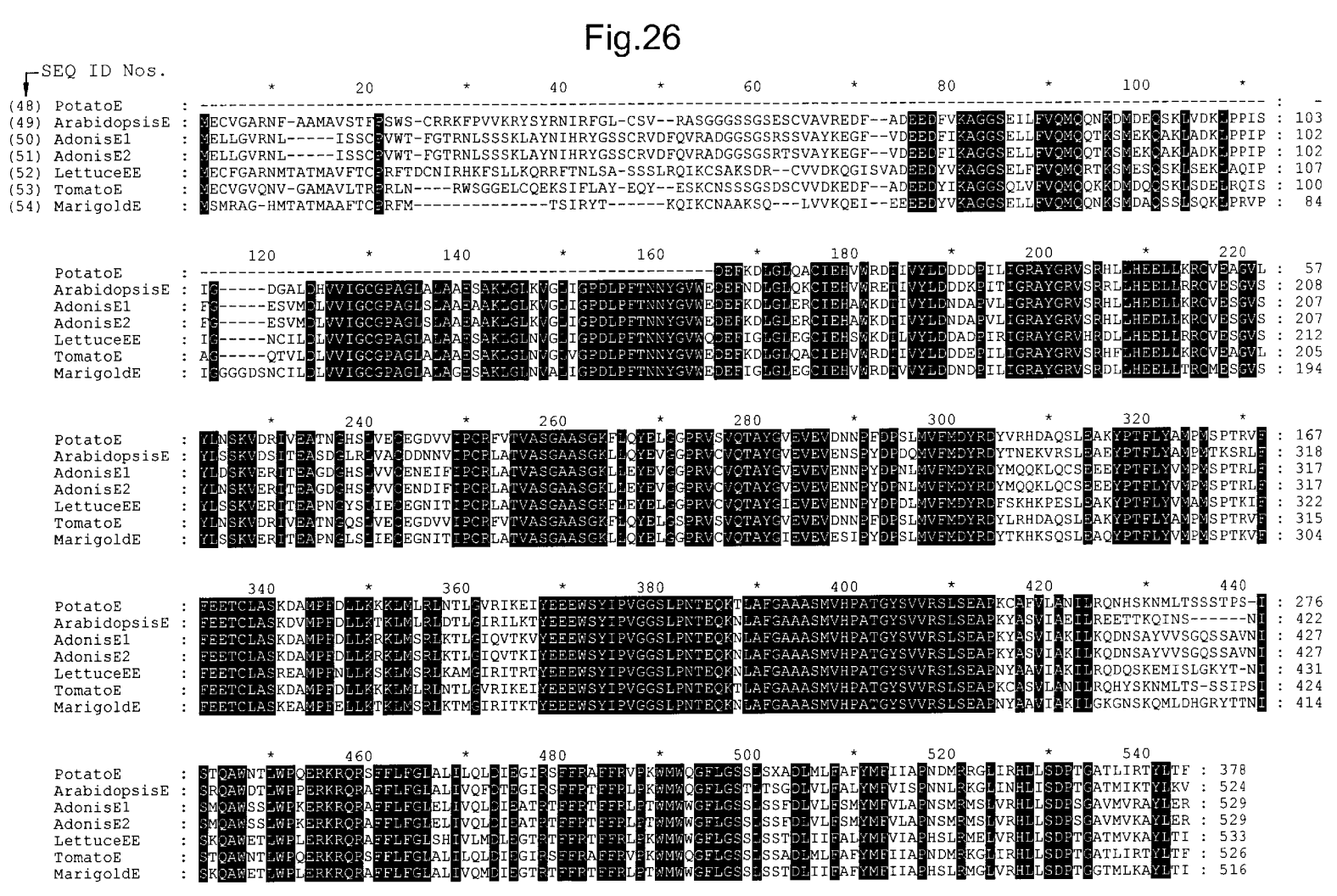

FIG. 26 shows a sequence alignment of the plant ∈-cyclases from FIG. 25 (SEQ ID NOS 48–54, respectively, in order of appearance). Those sequences outlined in black denote identical sequences among the ∈-cyclases.

Figure 27:
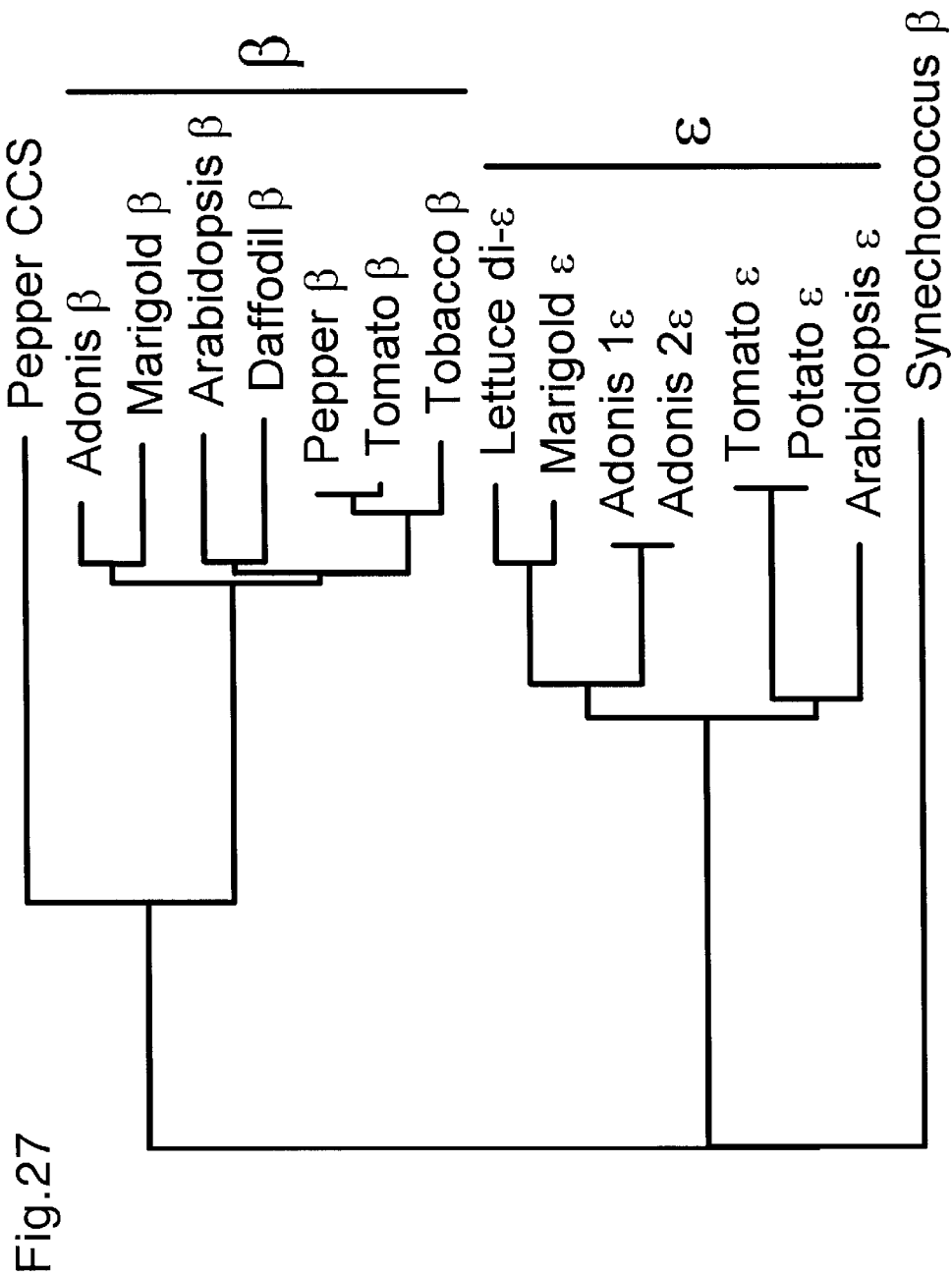

FIG. 27 is a dendogram or "tree" illustrating the degree of amino acid sequence similarity for various lycopene β- and ∈-cyclases (SEQ ID NOs. 48–61 and FIG. 27.

FIG. 28 shows a comparison between Arabidopsis ∈-cyclase (SEQ ID NO: 49) and lettuce ∈-cyclase (SEQ ID NO: 52) predicted amino acid sequences.

DESCRIPTION OF THE PREFERRED EMBODIMENTS

The present invention includes an isolated and/or purified nucleic acid sequence which encodes for a protein having lycopene ∈-cyclase, IPP isomerase or β-carotene hydroxylase enzyme activity and having the amino acid sequence of SEQ ID NOS:2, 4, 14–21, 23 or 25–27. Nucleic acids encoding lycopene ∈-cyclase, β-carotene hydroxylase and IPP isomerases have been isolated from several genetically distant sources.

The present inventors have isolated nucleic acids encoding the enzyme IPP isomerase, which catalyzes the reversible conversion of isopentenyl pyrophosphate (IPP) to dimethylallyl pyrophosphate (DMAPP). IPP isomerase cDNAs were isolated from the plants *A. thaliana*, *Tagetes erecta* (marigold), *Adonis palaestina* (pheasant's eye), *Lactuca sativa* (romaine lettuce) and from the green algae *H. pluvialis* and *Chlamydomonas reinhardtii*. Alignments of the amino acid sequences predicted by some of these cDNAs are shown in FIGS. 12 and 22. Plasmids containing some of these cDNAs were deposited with the American Type Culture Collection, 12301 Parklawn Drive, Rockville Md. 20852 on Mar. 4, 1996 under ATCC accession numbers 98000 (pHP05—*H. pluvialis*); 98001 (pMDP1—marigold); 98002 (pATDP7—*A. thaliana*) and 98004 (pHP04—*H. pluvialis*).

The present inventors have also isolated nucleic acids encoding the enzyme β-carotene hydroxylase, which is responsible for hydroxylating the β-endgroup in carotenoids. The nucleic acid of the present invention is shown in SEQ ID NO:3 and FIG. 5. The full length cDNA product hydroxylates both end groups of β-carotene as do products of cDNAs which encode proteins truncated by up to 50 amino acids from the N-terminus. Products of genes which encode proteins truncated between about 60–110 amino acids from the N-terminus preferentially hydroxylate only one ring. A plasmid containing this gene was deposited with the American Type Culture Collection, 12301 Parklawn Drive, Rockville Md. 20852 on Mar. 4, 1996 under ATCC accession number 98003 (pATOHB—*A. thaliana*).

The present inventors have also isolated nucleic acids encoding the enzyme lycopene ∈-cyclase, which is responsible for the formation of ∈-endgroups in carotenoids. The *A. thaliane* ∈-cyclase adds an ∈ ring to only one end of the symmetrical lycopene while the related β-cyclase adds a ring at both ends. The *A. thaliana* cDNA of the present invention is shown in FIG. 4 and SEQ ID NO:1. A plasmid containing this gene was deposited with the American Type Culture Collection, 12301 Parklawn Drive, Rockville Md. 20852 on Mar. 4, 1996 under ATCC accession number 98005 (pATeps—*A. thaliana*).

In addition, lycopene ∈-cyclases have been identified in lettuce and in *Adonis palaestina* (cDNA #5) which encode enzymes that convert lycopene to the bicyclic ∈-carotene (∈,∈-carotene). An additional cDNA from *Adonis palaestina* (cDNA #3) encodes a lycopene ∈-cyclase which converts lycopene into δ-carotene (∈,Ψ-carotene) and differs from the lycopene ∈-cyclase which forms bicyclic ∈-carotene (∈,∈-carotene) by only 5 amino acids. One or more of these amino acids may be modified by alteration of the nucleotide sequence in the #5 cDNA to obtain an enzyme which forms the bicyclic ∈,∈-carotene. The sequences of the *Adonis palaestina* and *Arabidopsis thaliana* ∈-cyclases have about 70% nucleotide identity and about 72% amino acid identity.

Initial experiments by the inventors with chimeric genes indicated that the part of the ∈-cyclase which is responsible for adding 2 ∈ rings to form ∈,∈-carotene is the carboxy terminal portion of the gene. The lettuce ∈-cyclase adds two ∈ rings to form ∈,∈-carotene. A DNA encoding a partial potato ∈-cyclase (missing its amino terminal portion), when combined with an amino terminal region from the lettuce ∈-cyclase gene, produces a monocyclic δ-carotene (∈,Ψ-carotene). With the discovery of the differences between the *Adonis palaestina* clone #3 and clone #5, the specific amino acids responsible for the addition of an extra ∈ ring have been identified (FIG. 24). Specifically, amino acid 55 is Thr in clone #3 and Ser in clone #5, amino acid 210 is Asn in clone #3 and Asp in clone #5, amino acid 231 is Asp in clone #3 and Glu in clone #5, amino acid 352 is Ile in clone #3 and Val in clone #5, and amino acid 524 is Lys in clone #3 and Arg in clone #5. It can be appreciated that these changes are quite conservative, as only one change, at amino acid 210, changes the charge of the protein.

Thus, it is clear that the nucleic acids of the invention encoding the enzymes as presently disclosed may be altered to increase a particularly desirable property of the enzyme, to change a property of the enzyme, or to diminish an undesirable property of the enzyme. Such modifications can be by deletion, substitution, or insertion of one or more amino acids, and can be performed by routine enzymatic manipulation of the nucleic acid encoding the enzyme (such as by restriction enzyme digestion, removal of nucleotides by mung bean nuclease or Bal31, insertion of nucleotides by Klenow fragment, and by religation of the ends), by site-directed mutagenesis, or may be accidental, such as by low fidelity PCR or those obtained through mutations in hosts that are producers of the enzymes. These techniques as well as other suitable techniques are well known in the art.

Mutations can be made in the nucleic acids of the invention such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids: Amino acids with nonpolar R groups: Alanine, Valine, Leucine, Isoleucine, Proline, Phenylalanine, Tryptophan and Methionine. Amino acids with uncharged polar R groups: Glycine, Serine, Threonine, Cysteine, Tyrosine, Asparagine and Glutamine. Amino acids with charged polar R groups (negatively charged at Ph 6.0): Aspartic acid and Glutamic acid. Basic amino acids (positively charged at pH 6.0): Lysine, Arginine and Histidine.

Another grouping may be those amino acids with phenyl groups: Phenylalanine, Tryptophan and Tyrosine.

Another grouping may be according to molecular weight (i.e., size of R groups).

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Amino acid substitutions may also be introduced to substitute an amino acid with a particularly preferable property. For example, a Cys may be introduced to provide a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

It is clear that certain modifications of SEQ ID NOS:2, 4, 14–21, 23 or 25–27 can take place without destroying the activity of the enzyme. It is noted especially that truncated versions of the nucleic acids of the invention are functional. For example, several amino acids (from 1 to about 120) can be deleted from the N-terminus of the lycopene ∈-cyclases of the invention, and a functional protein can still be produced. This fact is made especially clear from FIG. 25, which shows a sequence alignment of several plant ∈-cyclases. As can be seen from FIG. 25, there is an enormous amount of sequence disparity between amino acid sequences 2 to about 50–70 (depending on the particular sequence, since gaps are present). There is less, but also a substantial amount of, sequence dissimilarity between about 50–70 to about 90–120 (depending on the particular sequence). Thereafter, the sequences are fairly conserved, except for small pockets of dissimilarity between about 275–295 to about 285–305 (depending on the particular sequence), and between about 395–415 to about 410–430 (depending on the particular sequence).

The present inventors have found that the amount of the 5' region present in the nucleic acids of the invention can alter the activity of the enzyme. Instead of diminishing activity, truncating the 5' region of the nucleic acids of the invention may result in an enzyme with a different specificity. Thus, the present invention relates to nucleic acids and enzymes encoded thereby which are truncated to within 0–50, preferably 0–25, codons of the 5' initiation codon of their prokaryotic counterparts as determined by alignment maps as discussed below.

For example, when the cDNA encoding *A. thaliana* β-carotene hydroxylase was truncated, the resulting enzyme catalyzed the formation of βcryptoxanthin as the major product and zeaxanthin as minor product; in contrast to its normal production of zeaxanthin.

The present invention is intended to include those nucleic acid and amino acid sequences in which substitutions, deletions, additions or other modifications have taken place, as compared to SEQ ID NOS:2, 4, 14–21, 23 or 25–27, without destroying the activity of the enzyme. Preferably, the substitutions, deletions, additions or other modifications take place at the 5' end, or any other of those positions which already show dissimilarity between any of the presently disclosed amino acid sequences (see also FIG. 25) or other amino acid sequences which are known in the art and which encode the same enzyme (i.e., lycopene ∈-cyclase, IPP isomerase or β-carotene hydroxylase).

In each case, nucleic acid and amino acid sequence similarity and identity is measured using sequence analysis software, for example, the Sequence Analysis, Gap, or BestFit software packages of the Genetics Computer Group (University of Wisconsin Biotechnology Center, 1710 University Avenue, Madison, Wis. 53705), MEGAlign (DNAStar, Inc., 1228 S. Park St., Madison, Wis. 53715), or MacVector (Oxford Molecular Group, 2105 S. Bascom Avenue, Suite 200, Campbell, Calif. 95008). Such software uses algorithms to match similar sequences by assigning degrees of identity to various substitutions, deletions, and other modifications, and includes detailed instructions as to useful parameters, etc., such that those of routine skill in the art can easily compare sequence similarities and identities. An example of a useful algorithm in this regard is the algorithm of Needleman and Wunsch, which is used in the Gap program discussed above. This program finds the alignment of two complete sequences that maximizes the number of matches and minimizes the number of gaps. Another useful algorithm is the algorithm of Smith and Waterman, which is used in the BestFit program discussed above. This program creates an optimal alignment of the best segment of similarity between two sequences. Optimal alignments are found by inserting gaps to maximize the number of matches using the local homology algorithm of Smith and Waterman.

Conservative (i.e. similar) substitutions typically include substitutions within the following groups: glycine and alanine; valine, isoleucine and leucine; aspartic acid, glutamic acid, asparagine and glutamine; serine and threonine; lysine and arginine; and phenylalanine and tyrosine. Substitutions may also be made on the basis of conserved hydrophobicity or hydrophilicity (see Kyte and Doolittle, *J. Mol. Biol.* 157: 105–132 (1982)), or on the basis of the ability to assume similar polypeptide secondary structure (see Chou and Fasman, *Adv. Enzymol.* 47: 45–148 (1978)).

If comparison is made between nucleotide sequences, preferably the length of comparison sequences is at least 50 nucleotides, more preferably at least 60 nucleotides, at least 75 nucleotides or at least 100 nucleotides. It is most preferred if comparison is made between the nucleic acid sequences encoding the enzyme coding regions necessary for enzyme activity. If comparison is made between amino acid sequences, preferably the length of comparison is at least 20 amino acids, more preferably at least 30 amino acids, at least 40 amino acids or at least 50 amino acids. It is most preferred if comparison is made between the amino acid sequences in the enzyme coding regions necessary for enzyme activity.

It should be appreciated that also within the scope of the present invention are nucleic acid sequences encoding lycopene ∈-cyclases, IPP isomerases and β-carotene hydroxylases which code for enzymes having the same amino acid sequence as SEQ ID NOS:2, 4, 14–21, 23 or 25–27, but which are degenerate to the nucleic acids specifically disclosed herein.

The amino acid residues described herein are preferred to be in the "L" isomeric form. However, residues in the "D" isomeric form can be substituted for any L-amino acid residue, as long as the desired functional property of immunoglobulin-binding is retained by the polypeptide.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I–III [Ausubel, R. M., ed. (1994)]; "Cell Biology: A Laboratory Handbook" Volumes I–III [J. E. Celis, ed. (1994))]; "Current Protocols in Immunology" Volumes I–III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

The present invention also includes vectors. Suitable vectors according to the present invention comprise a nucleic acid of the invention encoding an enzyme involved in carotenoid biosynthesis or metabolism and a suitable promoter for the host, and can be constructed using techniques well known in the art (for example Sambrook et al., *Molecular Cloning A Laboratory Manual,* Cold Spring Harbor Laboratory, Cold Spring Harbor, N.Y., 1989; Ausubel et al., *Current Protocols in Molecular Biology,* Greene Publishing and Wiley Interscience, New York, 1991). Suitable vectors for eukaryotic expression in plants are described in Frey et al., Plant J. (1995) 8(5):693 and Misawa et al, 1994a; incorporated herein by reference. Suitable vectors for prokaryotic expression include pACYC 184, pUC 119, and pBR322 (available from New England BioLabs, Bevery, Mass.) and pTrcHis (Invitrogen) and pET28 (Novagen) and derivatives thereof. The vectors of the present invention can additionally contain regulatory elements such as promoters, repressors, selectable markers such as antibiotic resistance genes, etc.

The nucleic acids encoding the carotenoid enzymes as described above, when cloned into a suitable expression vector, can be used to overexpress these enzymes in a plant expression system or to inhibit the expression of these enzymes. For example, a vector containing the gene encoding lycopene ∈-cyclase can be used to increase the amount of α-carotene and carotenoids derived from α-carotene (such as lutein and α-cryptoxanthin) in an organism and thereby alter the nutritional value, pharmacology and visual appearance value of the organism.

Therefore, the present invention includes a method of producing or enhancing the production of a carotenoid in a host cell, relative to an untransformed host cell, the method comprising inserting into the host cell a vector comprising a heterologous nucleic acid sequence which encodes for a protein having lycopene ∈-cyclase, IPP isomerase or β-carotene hydroxylase enzyme activity, wherein the heterologous nucleic acid sequence is operably linked to a promoter; and expressing the heterologous nucleic acid sequence to produce the protein.

The present invention also includes a method of modifying the production of carotenoids in a host cell, the method comprising inserting into the host cell a vector comprising a heterologous nucleic acid sequence which produces an RNA and/or encodes for a protein which modifies lycopene ∈-cyclase, IPP isomerase or β-carotene hydroxylase enzyme activity, relative to an untransformed host cell, wherein the heterologous nucleic acid sequence is operably linked to a promoter; and expressing the heterologous nucleic acid sequence in the host cell to modify the production of the carotenoids in the host cell, relative to the untransformed host cell.

The term "modifying the production" means that the amount of carotenoids produced in the host cell can be enhanced, reduced, or left the same, as compared to the untransformed host cell. In accordance with one embodiment of the present invention, the make-up of the carotenoids (i.e., the specific carotenoids produced) is changed vis a vis each other, and this change in make-up may result in either a net gain, net loss, or no net change in the total amount of carotenoids produced in the cell. In accordance with another embodiment of the present invention, the production or the biochemical activity of the carotenoids (or the enzymes which catalyze their formation) is enhanced by the insertion of an enzyme-encoding nucleic acid of the invention. In yet another embodiment of the invention, the production or the biochemical activity of the carotenoids (or the enzymes which catalyze their formation) may be reduced or inhibited by a number of different approaches available to those skilled in the art, including but not limited to such methodologies or approaches as anti-sense (e.g., Gray et al (1992) Plant Mol. Biol. 19:69–87), ribozymes (e.g., Wegener et al (1994) Mol. Gen. Genet. 245:465–470), co-suppression (e.g., Fray and Grierson (1993) Plant Mol. Biol. 22:589–602), targeted disruption of the gene (e.g., Schaefer et al. (1997) Plant J. 11:1195–1206), intracellular antibodies (e.g., Rondon and Marasco (1997) Ann. Rev. Microbiol. 51:257–283) or whatever other approaches rely on the knowledge or availability of the nucleic acid or amino acid sequences of the invention and/or portions thereof, to thereby reduce accumulation of carotenoids with ∈ rings and compounds derived from them (for ∈-cyclase inhibition), or carotenoids with hydroxylated β rings and compounds derived from them (for β-hydroxylase inhibition), or, in the case if IPP isomerase, accumulation of any isoprenoid compound.

Preferably, at least a portion of the nucleic acid sequences used in the methods, vectors and host cells of the invention codes for an enzyme having an amino acid sequence which is at least 85% identical, preferably at least 90%, at least 95% or completely identical to SEQ ID NOS:2, 4, 14–21, 23 or 25–27. Sequence identity is determined as noted above. Preferably, sequence additions, deletions or other modifications are made as indicated above, so as to not affect the function of the particular enzyme.

In a preferred embodiment, vectors are manufactured which contain a DNA encoding a eukaryotic IPP isomerase upstream of a DNA encoding a second eukaryotic carotenoid enzyme. The inventors have discovered that inclusion of an IPP isomerase gene increases the supply of substrate for the carotenoid pathway; thereby enhancing the production of carotenoid endproducts, as compared to a host cell which is not transformed with such a vector. This is apparent from the much deeper pigmentation in carotenoid-accumulating colonies of $E.$ $coli$ which also contain one of the aforementioned IPP isomerase genes when compared to colonies that lack this additional IPP isomerase gene. Similarly, a vector comprising an IPP isomerase gene can be used to enhance production of any secondary metabolite of dimethylallyl pyrophosphate and/or isopentenyl pyrophosphate (such as isoprenoids, steroids, carotenoids, etc.). The term "isoprenoid" is intended to mean any member of the class of naturally occurring compounds whose carbon skeletons are composed, in part or entirely, of isopentyl $C_5$ units. Preferably, the carbon skeleton is of an essential oil, a fragrance, a rubber, a carotenoid, or a therapeutic compound, such as paclitaxel.

A vector containing the cDNA encoding a lycopene ∈-cyclase of the invention, preferably the lettuce lycopene ∈-cyclase or Adonis ∈-cyclase #5, can be used to increase the amount of bicyclic ∈-carotene in an organism and thereby alter the nutritional value, pharmacology and visual appearance value of the organism. In addition, the transformed organism can be used in the formulation of therapeutic agents, for example in the treatment of cancer (see Mayne et al (1996) FASEB J. 10:690–701; Tsushima et al (1995) Biol. Pharm. Bull. 18:227–233).

An antisense strand of a nucleic acid of the invention can be inserted into a vector. For example, the lycopene ∈-cyclase gene can be inserted into a vector and incorporated into the genomic DNA of a host, thereby inhibiting the synthesis of ∈,βcarotenoids (lutein and α-carotene) and enhancing the synthesis of β, β-carotenoids (zeaxanthin and β-carotene).

The present invention also relates to novel enzymes which are encoded by the amino acid sequences of the invention, or portions thereof.

The present invention also relates to novel enzymes which can transform known carotenoids into novel or uncommon products. Currently ∈-carotene (see FIG. 2) and γ-carotene are commonly produced only in minor amounts. As described below, an enzyme can be produced which transforms lycopene to γ-carotene and lycopene to ∈-carotene. With these products in hand, bulk synthesis of other carotenoids derived from them are possible. For example, ∈-carotene can be hydroxylated to form lactucaxanthin, an isomer of lutein (one ∈ and one β ring) and zeaxanthin (two β rings) where both endgroups are, instead, ∈ rings.

In addition to novel enzymes produced by truncating the 5' region of known enzymes, as discussed above, novel enzymes which can participate in the formation of unusual carotenoids can be formed by replacing portions of one gene with an analogous sequence from a structurally related gene. For example, βcyclase and ∈-cyclase are structurally related (see FIG. 13). By replacing a portion of β-lycopene cyclase with the analogous portion of ∈-cyclase, an enzyme which produces γ-carotene will be produced (one β endgroup). Further, by replacing a portion of the lycopene ∈-cyclase with the analogous portion of β-cyclase, an enzyme which produces ∈-carotene will be produced (with some exceptions, such as the lettuce ∈-cyclase, plant ∈-cyclases normally produce a compound with one ∈-endgroup, δ-carotene). Similarly, β-hydroxylase could be modified to produce enzymes of novel function by creation of hybrids with ∈-hydroxylase.

Host systems according to the present invention can comprise any organism that already produces carotenoids or which has been genetically modified to produce carotenoids. The IPP isomerase genes are more broadly applicable for enhancing production of any product dependent on DMAPP and/or IPP as a precursor.

Organisms which already produce carotenoids include plants, algae, some yeasts, fungi and cyanobacteria and other photosynthetic bacteria. Transformation of these hosts with vectors according to the present invention can be done using standard techniques such as those described in Misawa et al., (1990) supra; Hundle et al., (1993) supra; Hundle et al., (1991) supra; Misawa et al., (1991) supra; Sandmann et al., supra; and Schnurr et al., supra.

Transgenic organisms can be constructed which include the nucleic acid sequences of the present invention (Bird et al, 1991; Bramley et al, 1992; Misawa et al, 1994a; Misawa et al, 1994b; Cunningham et al, 1993). The incorporation of these sequences can allow the controlling of carotenoid biosynthesis, content, or composition in the host cell. These transgenic systems can be constructed to incorporate sequences which allow for the overexpression of the nucleic acids of the present invention. Transgenic systems can also be constructed containing antisense expression of the nucleic acid sequences of the present invention. Such antisense expression would result in the accumulation of the substrates of the substrates of the enzyme encoded by the sense strand.

A method for screening for eukaryotic genes which encode enzymes involved in carotenoid biosynthesis comprises transforming a prokaryotic host with a nucleic acid which may contain a eukaryotic or prokaryotic carotenoid biosynthetic gene; culturing said transformed host to obtain colonies; and screening for colonies exhibiting a different color than colonies of the untransformed host.

Suitable hosts include *E. coli*, cyanobacteria such as Synechococcus and Synechocystis, alga and plant cells. *E. coli* are preferred.

In a preferred embodiment, the above "color complementation" screening protocol can be enhanced by using mutants which are either (1) deficient in at least one carotenoid biosynthetic gene or (2) overexpress at least one carotenoid biosynthetic gene. In either case, such mutants will accumulate carotenoid precursors.

Prokaryotic and eukaryotic DNA or cDNA libraries can be screened in total for the presence of genes of carotenoid biosynthesis, metabolism and degradation. Preferred organisms to be screened include photosynthetic organisms.

*E. coli* can be transformed with these eukaryotic cDNA libraries using conventional methods such as those described in Sambrook et al, 1989 and according to protocols described by the vendors of the cloning vectors.

For example, the cDNA libraries in bacteriophage vectors such as lambdaZAP (Stratagene) or lambda ZIPLOX (Gibco BRL) can be excised en masse and used to transform *E.coli*.

Transformed *E. coli* can be cultured using conventional techniques. The culture broth preferably contains antibiotics to select and maintain plasmids. Suitable antibiotics include penicillin, ampicillin, chloramphenicol, etc. Culturing is typically conducted at 15–40° C., preferably at room temperature or slightly above (18–28° C.), for 12 hours to 7 days.

Cultures are plated and the plates are screened visually for colonies with a different color than the colonies of the host *E. coli* transformed with the empty plasmid cloning vector. For example, *E. coli* transformed with the plasmid, pAC-BETA (described below), produce yellow colonies that accumulate β-carotene. After transformation with a cDNA library, colonies which contain a different hue than those formed by *E. coli*/pAC-BETA would be expected to contain enzymes which modify the structure or accumulation of β-carotene. Similar *E. coli* strains can be engineered which accumulate earlier products in carotenoid biosynthesis, such as lycopene, γ-carotene, etc.

Having generally described this invention, a further understanding can be obtained by reference to certain specific examples which are provided herein for purposes of illustration only and are not intended to be limiting unless otherwise specified.

EXAMPLE

I. Isolation of β-carotene hydroxylase

Plasmid Construction

An 8.6 kb BglII fragment containing the carotenoid biosynthetic genes of *Erwinia herbicola* was first cloned in the BamHI site of plasmid vector pACYC 184 (chloramphenicol resistant), and then a 1.1 kb BamHI fragment containing the *E. herbicola* β-carotene hydroxylase (CrtZ) was deleted. *E.coli* strains containing the resulting plasmid, pAC-BETA, accumulate β-carotene and form yellow colonies (Cunningham et al., 1994).

A full length cDNA encoding IPP isomerase of *Haematococcus pluvialis* (HP04) was first excised with BamHI and KpnI from pBluescript SK-, and then ligated into the corresponding sites of the pTrcHisA vector with high-level expression from the trc promoter (Invitrogen, Inc.). A fragment containing the IPP isomerase and trc promoter was subsequently excised with EcoRV and KpnI, treated with the Klenow fragment of DNA polymerase to produce blunt ends, and ligated in the Klenow-treated HindIII site of pAC-BETA. *E. coli* cells transformed with this new plasmid pAC-BETA-04 form orange colonies on LB plates (vs. yellow for those containing pAC-BETA) and cultures accumulate substantially more β-carotene (ca. two fold) than those that contain pAC-BETA.

Screening of an Arabidopsis cDNA Library

Several λ cDNA expression libraries of Arabidopsis were obtained from the Arabidopsis Biological Resource Center (Ohio State University, Columbus, Ohio.) (Kieber et al., 1993). The λ cDNA libraries were excised in vivo using Stratagene's ExAssist SOLR system to produce a phagemid cDNA library wherein each phagemid contained also a gene conferring resistance to the antibiotic ampicillin.

*E.coli* strain DH10BZIP was chosen as the host cell for the screening and pigment production, although we have also used TOP 10F' and XL1-Blue for this purpose. DH10B cells were transformed with plasmid pAC-BETA-04 and were plated on LB agar plates containing chloramphenicol at 50 µg/ml (from United States Biochemical Corporation). The phagemid Arabidopsis cDNA library was then introduced into DH10B cells already containing pAC-BETA-04. Transformed cells containing both pAC-BETA-04 and Arabidopsis cDNA library phagemids were selected on chloramphenicol plus ampicillin (150 µg/ml) agar plates. Maximum color development occurred after 3 to 7 days incubation at room temperature, and the rare bright yellow colonies were selected from a background of many thousands of orange colonies on each agar plate. Selected colonies were inoculated into 3 ml liquid LB medium containing ampicillin and chloramphenicol, and cultures were incubated at room temperature for 1–2 days, with shaking. Cells were then harvested by centrifugation and extracted with acetone in microfuge tubes. After centrifugation, the pigmented extract was spotted onto silica gel thin-layer chromatography (TLC) plates, and developed with a hexane:ether (1:1, by volume) mobile phases. β-carotene hydroxylase-encoding cDNAs were identified based on the appearance of a yellow pigment that co-migrated with zeaxanthin on the TLC plates.

Subcloning and Sequencing

The plasmid containing the β-carotene hydroxylase cDNA was recovered and analyzed by standard procedures (Sambrook et al., 1989). The Arabidopsis β-carotene hydroxylase was sequenced completely on both strands on an automatic sequencer (Applied Biosystems, Model 373A, Version 2.0.1S). The cDNA insert of 0.95 kb also was excised and ligated into the a pTrcHis vector. A BglII restriction site within the cDNA was used to remove that portion of the cDNA that encodes the predicted polypeptide N terminal sequence region that is not also found in bacterial β-carotene hydroxylases (FIG. 6). A BglII-XhoI fragment was directionally cloned in BamHI-XhoI digested TrcHis vectors.

Pigment Analysis

A single colony was used to inoculate 50 ml of LB containing ampicillin and chloramphenicol in a 250-ml flask. Cultures were incubated at 28° C. for 36 hours with gentle shaking, and then harvested at 5000 rpm in an SS-34 rotor. The cells were washed once with distilled $H_2O$ and resuspended with 0.5 ml of water. The extraction procedures and HPLC were essentially as described previously (Cunningham et al, 1994).

II. Isolation and biochemical analysis of an Arabidopsis lycopene ∈-cyclase

Plasmid Construction

Construction of plasmids pAC-LYC, pAC-NEUR, and pAC-ZETA is described in Cunningham et al., (1994). In brief, the appropriate carotenoid biosynthetic genes from *Erwinia herbicola, Rhodobacter capsulatus,* and *Synechococcus sp.* strain PCC7942 were cloned in the plasmid vector pACYC184 (New England BioLabs, Beverly, Mass.). Cultures of *E. coli* containing the plasmids pAC-ZETA, pAC-NEUR, and pAC-LYC, accumulate ζ-carotene, neurosporene, and lycopene, respectively. The plasmid pAC-ZETA was constructed as follows: an 8.6-kb BglII fragment containing the carotenoid biosynthetic genes of *E. herbicola* (GenBank M87280; Hundle et al., 1991) was obtained after partial digestion of plasmid pPL376 (Perry et al., 1986; Tuveson et al., 1986) and cloned in the BamHI site of pACYC184 to give the plasmid pAC-EHER. Deletion of adjacent 0.8- and 1.1-kb BamHI-BamHI fragments (deletion Z in Cunningham et al., 1994), and of a 1.1 kB SalI—SalI fragment (deletion X) served to remove most of the coding regions for the *E. herbicola* β-carotene hydroxylase (crtZ gene) and zeaxanthin glucosyltransferase (crtX gene), respectively. The resulting plasmid, pAC-BETA, retains functional genes for geranylgeranyl pyrophosphate synthase (crtE), phytoene synthase (crtB), phytoene desaturase (crtI), and lycopene cyclase (crtY). Cells of *E. coli* containing this plasmid form yellow colonies and accumulate βcarotene. A plasmid containing both the lycopene ∈-and βcyclase cDNAs of *A. thaliana* was constructed by excising the ∈-cyclase in clone y2 as a PvuI-PvuII fragment and ligating this piece in the SnaBI site of a plasmid (pSPORT 1 from GIBCO-BRL) that already contained the β-cyclase (Cunningham et al., 1996).

Organisms and Growth Conditions

*E. coli* strains TOP10 and TOP10 F' (obtained from Invitrogen Corporation, San Diego, Calif.) and XL1-Blue (Stratagene) were grown in Luria-Bertani (LB) medium (Sambrook et al., 1989) at 37° C. in darkness on a platform shaker at 225 cycles per min. Media components were from Difco (yeast extract and tryptone) or Sigma (NaCl). Ampicillin at 150 µg/mL and/or chloramphenicol at 50 µg/mL (both from United States Biochemical Corporation) were used, as appropriate, for selection and maintenance of plasmids.

Mass Excision and Color Complementation Screening of an A. thaliana cDNA Library A size-fractionated 1–2 kB cDNA library of *A. thaliana* in lambda ZAPII (Kieber et al., 1993) was obtained from the Arabidopsis Biological Resource Center at The Ohio State University (stock number CD4-14). Other size fractionated libraries were also obtained (stock numbers CD4-13, CD4-15, and CD4-16). An aliquot of each library was treated to cause a mass excision of the cDNAs and thereby produce a phagemid library according to the instructions provided by the supplier of the cloning vector (Stratagene; *E. coli* strain XL1-Blue and the helper phage R408 were used). The titre of the excised phagemid was determined and the library was introduced into a lycopene-accumulating strain of *E. coli* TOP10 F' (this strain contained the plasmid pAC-LYC) by incubation of the phagemid with the *E. coli* cells for 15 min at 37° C. Cells had been grown overnight at 30° C. in LB medium supplemented with 2% (w/v) maltose and 10 mM $MgSO_4$ (final concentration), and harvested in 1.5 ml microfuge tubes at a setting of 3 on an Eppendorf microfuge (5415C) for 10 min. The pellets were resuspended in 10 mM $MgSO_4$ to a volume equal to one-half that of the initial culture volume. Transformants were spread on large (150 mm diameter) LB agar petri plates containing antibiotics to provide for selection of cDNA clones (ampicillin) and maintenance of pAC-LYC (chloramphenicol). Approximately 10,000 colony forming units were spread on each plate. Petri plates were incubated at 37 C. for 16 hr and then at room temperature for 2 to 7 days to allow maximum color development. Plates were screened visually with the aid of an illuminated 3× magnifier and a low power stage-dissecting microscope for the rare, pale pinkish-yellow to deep-yellow colonies that could be observed in the background of pink colonies. A colony color of yellow or pinkish-yellow was taken as presumptive evidence of a cyclization activity. These yellow colonies were collected with sterile toothpicks and used to inoculate 3 ml of LB medium in culture tubes with overnight growth at 37° C. and shaking at 225 cycles/min. Cultures were split into two aliquots in microfuge tubes and harvested by centrifugation at a setting of 5 in an Eppendorf 5415C microfuge. After discarding the liquid, one pellet was frozen for later purification of plasmid DNA. To the second pellet was added 1.5 ml EtOH, and the pellet was resuspended by vortex mixing, and extraction was allowed to proceed in the dark for 15–30 min with occasional remixing. Insoluble materials were pelleted by centrifugation at maximum speed for 10 min in a microfuge. Absorption spectra of the supernatant fluids were recorded from 350–550 nm with a Perkin Elmer lambda six spectrophotometer.

Analysis of Isolated Clones

Eight of the yellow colonies contained β-carotene indicating that a single gene product catalyzes both cyclizations required to form the two β endgroups of the symmetrical β-carotene from the symmetrical precursor lycopene. One of the yellow colonies contained a pigment with the spectrum characteristic of δ-carotene, a monocyclic carotenoid with a single ∈ endgroup. Unlike the β cyclase, this ∈-cyclase appears unable to carry out a second cyclization at the other end of the molecule.

The observation that ∈-cyclase is unable to form two cyclic ∈-endgroups (e.g. the bicyclic ∈-carotene) illuminates the mechanism by which plants can coordinate and control the flow of substrate into carotenoids derived from β-carotene versus those derived from α-carotene and also can prevent the formation of carotenoids with two ∈ endgroups.

The availability of the *A. thaliana* gene encoding the ∈-cyclase enables the directed manipulation of plant and algal species for modification of carotenoid content and composition. Through inactivation of the ∈-cyclase, whether at the gene level by deletion of the gene or by insertional inactivation or by reduction of the amount of enzyme formed (by such as antisense technology), one may increase the formation of β-carotene and other pigments derived from it. Since vitamin A is derived only from carotenoids with β endgroups, an enhancement of the production of β-carotene versus α-carotene may enhance nutritional value of crop plants. Reduction of carotenoids with ∈-endgroups may also be of value in modifying the color properties of crop plants and specific tissues of these plants. Alternatively, where production of α-carotene, or pigments such as lutein that are derived from α-carotene, is desirable, whether for the color properties, nutritional value or other reason, one may overexpress the ∈-cyclase or express it in specific tissues. Wherever agronomic value of a crop is related to pigmentation provided by carotenoid pigments the directed manipulation of expression of the ∈-cyclase gene and/or production of the enzyme may be of commercial value.

The predicted amino acid sequence of the *A. thaliana* ∈-cyclase enzyme was determined. A comparison of the amino acid sequences of the β- and ∈-cyclase enzymes of *Arabidopsis thaliana* (FIG. 13) as predicted by the DNA sequence of the respective cDNAs (FIG. 4 for the ∈-cyclase cDNA sequence), indicates that these two enzymes have many regions of sequence similarity, but they are only about 37% identical overall at the amino acid level. The degree of sequence identity at the DNA base level, only about 50%, is sufficiently low such that we and others have been unable to detect this gene by hybridization using the β cyclase as a probe in DNA gel blot experiments.

REFERENCES

Each reference cited in this application and/or listed below is hereby incorporated by reference.

Bird et al, 1991 Biotechnology 9, 635–639.

Bishop et al., (1995) FEBS Lett. 367, 158–162.

Bramley, P. M. (1985) Adv. Lipid Res. 21, 243–279.

Bramley, P. M. (1992) Plant J. 2, 343–349.

Britton, G. (1988). Biosynthesis of carotenoids. In Plant Pigments, T. W. Goodwin, ed. (London: Academic Press), pp. 133–182.

Britton, G. (1979) Z. Naturforsch. Section C. Biosci. 34, 979–985.

Britton, G. (1995) UV/Visible spectroscopy. In Carotenoids, Vol. IB: Spectroscopy, G. Britton, S. Liaaen-Jensen, H. P. Pfander, eds. (Basel: Birkhauser Verlag), pp. 13–62.

Bouvier et al., (1994) Plant J. 6, 45–54.

Cunningham et al., (1985) Photochem. Photobiol. 42: 295–307.

Cunningham et al., (1993) FEBS Lett. 328, 130–138.

Cunningham et al., (1994) Plant Cell 6, 1107–1121.

Cunningham et al., (1996) Plant Cell 8, 1613–1626.

Davies, B. H. (1976). Carotenoids. In Chemistry and Biochemistry of Plant Pigments, Vol. 2, T. W. Goodwin, ed (New York: Academic Press), pp. 38–165.

Del Sal et al., (1988). Nucl. Acids Res. 16, 9878.

Demmig-Adams & Adams, (1992) Ann. Rev. Plant Physiol. Mol. Biol. 43, 599–626.

Enzell & Back, (1995) Mass spectrometry. In Carotenoids, Vol. IB: Spectroscopy, G. Britton, S. Liaaen-Jensen, H. P. Pfander, eds. (Basel: Birkhauser Verlag), pp. 261–320.

Frank & Cogdell (1993) Photochemistry and function of carotenoids in photosynthesis. In Carotenoids in Photosynthesis. A. Young and G. Britton, eds. (London: Chapman and Hall). pp. 253–326.

Goodwin, T. W. (1980). The Biochemistry of the Carotenoids. 2nd ed, Vol. 1 (London:

Chapman and Hall.

Horvath et al., (1972) Phytochem. 11, 183–187.

Hugueney et al., (1995) Plant J. 8, 417–424.

Hundle et al., (1991) Photochem. Photobiol. 54, 89–93.

Jensen & Jensen, (1971) Methods Enzymol. 23, 586–602.

Kargl & Quackenbush, (1960) Archives Biochem. Biophys. 88, 59–63.

Kargl et al., (1960) Proc. Am. Hort. Soc. 75, 574–578.

Kieber et al., (1993) Cell 72, 427–441.

Koyama, Y. (1991) J. Photochem. Photobiol., B, 9, 265–80.

Krinsky, N. I. (1987) Medical uses of carotenoids. In Carotenoids, N. I. Krinsky, M. M. Mathews-Roth, and R. F. Taylor, eds. (New York: Plenum), pp. 195–206.

Kyte & Doolittle, (1982) J. Mol. Biol. 157, 105–132.

LaRossa & Schloss, (1984) J. Biol. Chem. 259, 8753–8757.

Misawa et al., (1994a) Plant J. 6, 481–489.

Misawa et al., (1994b) J. Biochem, Tokyo, 116, 980–985.

Norris et al., (1995) Plant Cell 7, 2139–2149.

Pecker et al., (1996) Submitted to Plant Mol. Biol.
Perry et al., (1986) J. Bacteriol. 168, 607–612.
Persson & Argos, (1994) J. Mol. Biol. 237, 182–192.
Plumley & Schmidt, (1987) Proc. Nat. Acad. Sci. USA 83, 146–150.
Plumley & Schmidt, (1995) Plant Cell 7, 689–704.
Rossmann et al., (1974) Nature 250, 194–199.
Rock & Zeevaart (1991) Proc. Nat. Acad. Sci. USA 88, 7496–7499.
Rost et al., (1995) Protein Science 4, 521–533.
Sambrook et al., (1989) Molecular Cloning: A Laboratory Manual, 2nd edition (Cold Spring Harbor, N.Y.: Cold Spring Harbor Laboratory Press).
Sancar, A. (1994) Biochemistry 33, 2–9.
Sander & Schneider, (1991) Proteins 9, 56–68.
Sandmann, G. (1994) Eur. J. Biochem. 223, 7–24.
Scolnik & Bartley, (1995) Plant Physiol. 108, 1342.
Siefermann-Harms, D. (1987) Physiol. Plant. 69, 561–568.
Spurgeon & Porter, (1980). Biosynthesis of carotenoids. In Biochemistry of Isoprenoid Compounds, J. W. Porter, and S. L. Spurgeon, eds. (New York: Wiley), pp. 1–122.
Tomes, M. L. (1963) Bot. Gaz. 124, 180–185.
Tomes, M. L. (1967) Genetics 56, 227–232.
Tuveson et al., (1986) J. Bacteriol. 170, 4675–4680.
Van Beeumen et al., (1991) J. Biol. Chem. 266, 12921–12931.
Weedon & Moss, (1995) Structure and Nomenclature. In Carotenoids, Vol. IB: Spectroscopy, G. Britton, S. Liaaen-Jensen, H. P. Pfander, eds. (Basel: Birkhauser Verlag), pp. 27–70.
Wierenga et al., (1986) J. Mol. Biol. 187, 101–107.
Zechmeister, L. (1962) Cis-Trans Isomeric Carotenoids, Vitamins A and Arylpolyenes. Springer-Verlag, Vienna.

Having now fully described the invention, it will be apparent to one of ordinary skill in the art that many changes and modifications can be made thereto without departing from the spirit or scope of the invention as set forth herein.

We claim:

1. A method of producing or altering the production of at least one carotenoid in a host cell, relative to an untransformed host cell, the method comprising:
   a) inserting into the host cell a vector comprising a heterologous plant nucleic acid sequence which encodes SEQ ID NO:2, wherein said heterologous plant nucleic acid sequence is operably linked to a promoter; and
   b) expressing the heterologous plant nucleic acid sequence to produce, enhance, reduce, or otherwise affect the production of carotenoids in the host cell.

2. The method of claim 1, wherein the host cell is selected from the group consisting of a bacterial cell, an algal cell, a yeast cell and a plant cell.

3. The method of claim 1, wherein the host cell is a photosynthetic cell.

Figure 2:
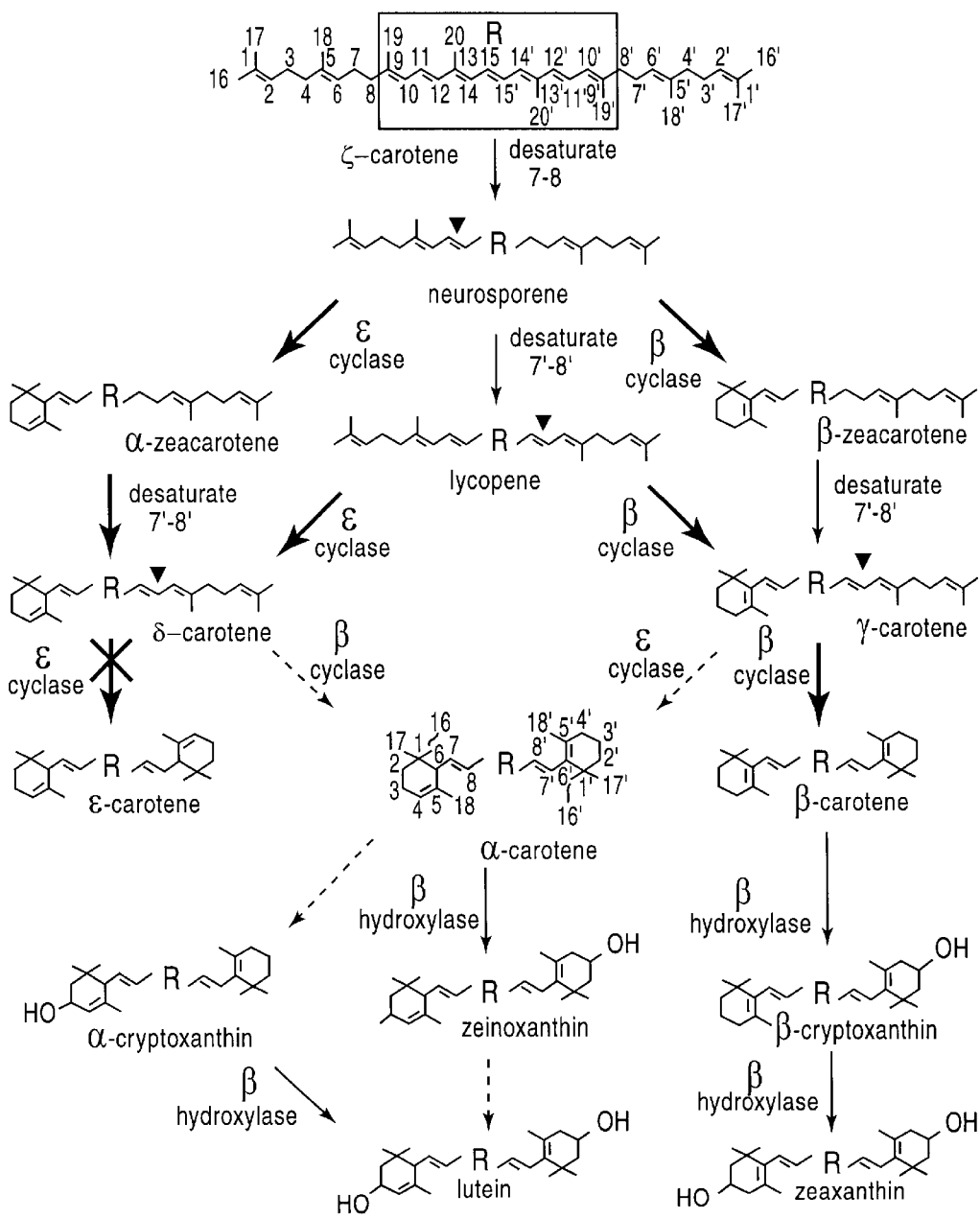
FIG. 2 depicts possible routes of synthesis of cyclic carotenoids and common plant and algal xanthophylls (oxycarotenolds) from neurosporene. Demonstrated activities of the β- and ∈-cyclase enzymes of A. thaliana are indicated by bold arrows labelled with βor ∈ respectively. A bar below the arrow leading to ∈-carotene indicates that the enzymatic activity was examined but no product was detected. The steps marked by an arrow with a dotted line have not been specifically examined. Conventional numbering of the carbon atoms is given for neurosporene and α-carotene. Inverted triangles (▼) mark positions of the double bonds introduced as a consequence of the desaturation reactions.
Figure 3:
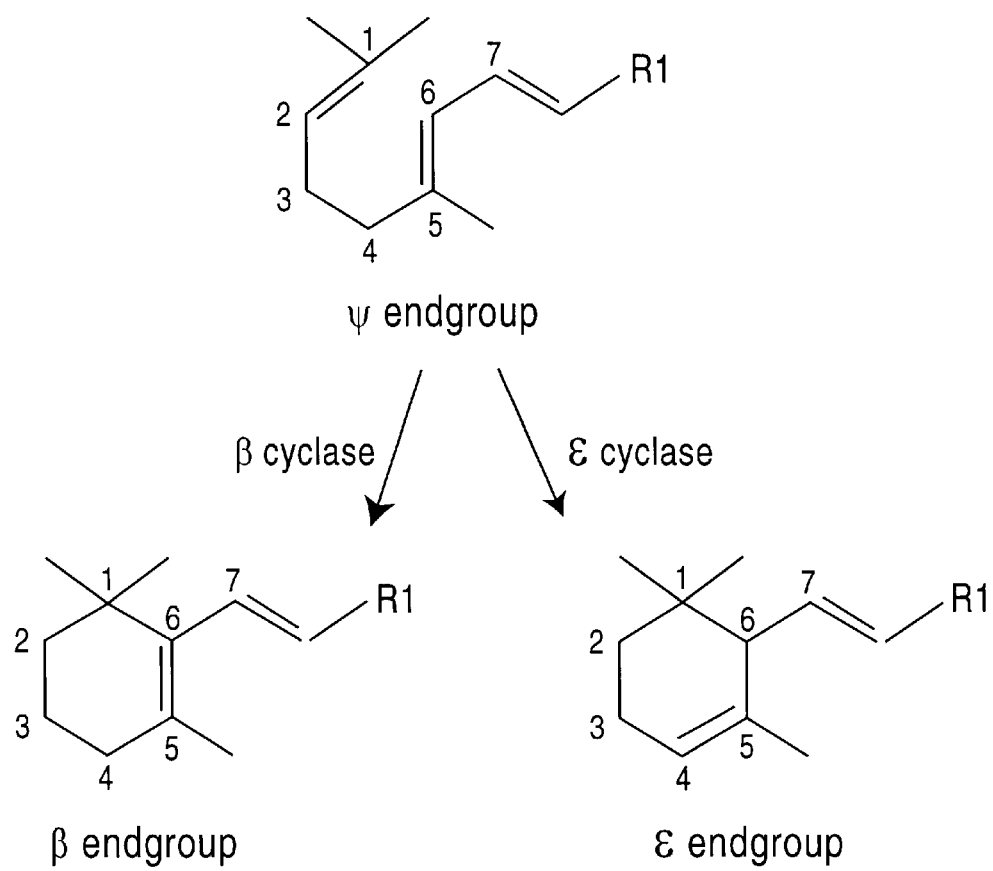
FIG. 3 depicts the carotene endgroups which are found in plants.

4. A method of producing or altering the production of at least one carotenoid in a host cell, relative to an untransformed host cell, the method comprising:
   a) inserting into the host cell a vector comprising a heterologous plant nucleic acid sequence which encodes an amino acid sequence that is at least 85% identical to SEQ ID NO:23 or 26, wherein said heterologous plant nucleic acid sequence is operably linked to a promoter; and
   b) expressing the heterologous plant nucleic acid sequence to produce, enhance, reduce, or otherwise affect the production of carotenoids in the host cell, wherein said heterologous plant nucleic acid sequence encodes a protein having ∈-cyclase activity as depicted in FIG. 2.

5. The method of claim 4, wherein the heterologous plant nucleic acid sequence has a sequence which encodes SEQ ID NO:23 or 26.

6. The method of claim 4, wherein the host cell is selected from the group consisting of a bacterial cell, an algal cell, a yeast cell and a plant cell.

7. The method of claim 4, wherein the host cell is a photosynthetic cell.

8. A method of producing or altering the production of at least one carotenoid in a host cell, relative to an untransformed host cell, the method comprising:
   a) inserting into the host cell a vector comprising a heterologous plant nucleic acid sequence which encodes SEQ ID NO:25, wherein said heterologous plant nucleic acid sequence is operably linked to a promoter; and
   b) expressing the heterologous plant nucleic acid sequence to produce, enhance, reduce, or otherwise affect the production of carotenoids in the host cell.

9. The method of claim 8, wherein the host cell is selected from the group consisting of a bacterial cell, an algal cell, a yeast cell and a plant cell.

10. The method of claim 8, wherein the host cell is a photosynthetic cell.

* * * * *